United States Patent [19]

Hamashima

[11] Patent Number: 4,912,224

[45] Date of Patent: Mar. 27, 1990

[54] CARBOXYALKENAMIDOCEPHALOSPORINS

[75] Inventor: Yoshio Hamashima, Kyoto, Japan

[73] Assignee: Shionogi & Co., Ltd., Osaka, Japan

[21] Appl. No.: 132,882

[22] Filed: Dec. 9, 1987

Related U.S. Application Data

[60] Division of Ser. No. 831,435, Feb. 20, 1986, Pat. No. 4,748,170, which is a division of Ser. No. 711,017, Mar. 12, 1985, Pat. No. 4,634,697, Continuation-in-part of Ser. No. 656,731, Oct. 1, 1984, abandoned.

[30] Foreign Application Priority Data

Oct. 4, 1983 [JP] Japan ................................. 58-186601
Feb. 3, 1984 [JP] Japan ................................. 59-18563
May 18, 1984 [JP] Japan ................................. 59-100890

[51] Int. Cl.[4] ..................................... G07D 333/04
[52] U.S. Cl. ............................. 548/127; 548/139; 548/128; 548/135; 548/138; 548/194; 548/195
[58] Field of Search ............... 540/215, 221, 222, 225, 540/227, 228, 120; 548/196, 127, 128, 194, 195, 135, 138, 139; 514/203, 206, 207

[56] References Cited

U.S. PATENT DOCUMENTS 3,994,888 11/1976 Kukolja ........................... 260/243 C
4,014,869  3/1977 Gregory et al. ...................... 544/16
4,416,880 11/1983 Boberg et al. ...................... 424/246
4,500,716  2/1985 Kinast ................................ 544/28
4,634,697  1/1987 Hamashima ......................... 540/222

FOREIGN PATENT DOCUMENTS

42/10996  6/1967 Japan.
  966131   8/1964 United Kingdom.
 2045749  11/1980 United Kingdom.
 2076801A 12/1981 United Kingdom.

OTHER PUBLICATIONS

Adams et al., J. Org. Chem., vol. 37, No. 24 (1972) 3906–13.
Noland et al., J. Org. Chem., vol. 45 (1980) 4573–4582.
Kawahara et al., Heterocycles, vol. 14, No. 1 (1980) 15–18.
Visser et al., J. Chem. Soc. Chem. Commun. (1982) 669.
Medici et al., J. Chem. Soc. Chem. Commun. (1980) 1077.

Primary Examiner—William R. Dixon, Jr.
Assistant Examiner—Miriam Sohn
Attorney, Agent, or Firm—Wenderoth, Lind & Ponack

[57] ABSTRACT

An antibacterial 7beta-(carboxyalkenoyl)amino-3-cephem-4-carboxylic acid represented by the following formula:

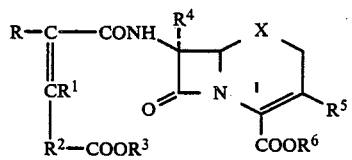

(wherein
R is aryl or a heterocyclic group;
$R^1$ is hydrogen or halogen;
$R^2$ is a single bond, alkylene, or thiaalkylene;
$R^3$ is a hydrogen atom or carboxy modifying group;
$R^4$ is hydrogen or methoxy;
$R^5$ is hydrogen or a 3-substituent of cephalosporins;
$R^6$ is a hydrogen atom or carboxy modifying group; and
X is oxygen, sulfur, or sulfinyl)

a pharmaceutical composition containing the same, and a method for treating a bacterial infection with the same.

8 Claims, No Drawings

CARBOXYALKENAMIDOCEPHALOSPORINS

This application is a division of application Ser. No. 831,435, filed Feb. 20, 1986, (now U.S. Pat. No. 4,748,170) which application is a division of application Ser. No. 711,017, filed Mar. 12, 1985 (now U.S. Pat. No. 4,634,697), which application is in turn, a continuation-in-part of application Ser. No. 656,731, filed Oct. 1, 1984 (now abandoned).

This invention relates to antibacterial 7beta-(carboxyalkenoylamino)-3-cephem-4-carboxylic acids represented by the following formula:

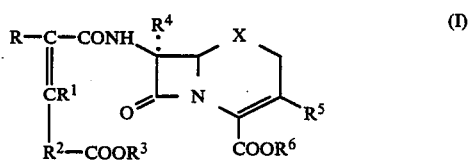

(wherein
R is aryl or a heterocyclic group;
$R^1$ is hydrogen or halogen;
$R^2$ is a single bond, alkylene, or thiaalkylene;
$R^3$ is a hydrogen atom or carboxy modifying group;
$R^4$ is hydrogen or methoxy;
$R^5$ is hydrogen or a 3-substituent of cephalosporins;
$R^6$ is hydrogen atom or carboxy modifying group; and
X is oxygen, sulfur, or sulfinyl)

The following explains the variable groups of the formula (I):

R as aryl is optionally substituted phenyl. R as a heterocyclic group is an optionally substituted 5 or 6 membered monocyclic ring group containing 1 to 4 hetero atoms selected from oxygen, nitrogen, and sulfur. Representative rings are pyrryl, furyl, thienyl, pyrazolyl, imidazolyl, oxazolyl, isoxazolyl, thiazolyl, isothiazolyl, triazolyl, oxadiazolyl, thiadiazolyl, tetrazolyl, thiatriazolyl, pyridyl, pyrimidyl, pyrazinyl, triazinyl, and the like. Here, the said substituents include, among other conventional ones, alkyl, substituted alkyl, carboxy, protected carboxy, amino, protected amino, hydroxy, protected hydroxy, halogen, sulfamoyl, and the like. Among the protecting groups in the protected amino, preferably are 7 to 20 C optionally substituted aralkyl (e.g., benzyl, benzhydryl, trityl, methoxybenzyl, dimethoxybenzyl, nitrobenzyl, methylbenzyl, dimethylbenzyl), 1 to 8 C optionally substituted alkyl (e.g., trichloromethyl, trichloroethyl, trifluoromethyl, tetrahydropyranyl), substituted phenylthio, 1 to 8 C substituted alkylidene, 7 to 14 C substituted aralkylidene, 5 to 8 C substituted cycloalkylidene, acyl [e.g., 1 to 8 C optionally substituted alkanoyl (e.g., formyl, acetyl, chloroacetyl, trifluoroacetyl), 2 to 12 C optionally substituted lower alkoxycarbonyl (in which the alkyl part is methyl, ethyl, propyl, cyclopropylethyl, isopropyl, butyl, pentyl, hexyl, trichloroethyl, pyridylmethyl, cyclopentyl, cyclohexyl, quinolylmethyl, or the like), 8 to 15 C optionally substituted aralkoxycarbonyl (in which the aralkyl part is benzyl, diphenylmethyl, nitrobenzyl, or the like), succinyl, phthaloyl], trialkylsilyl, alkoxydialkylsilyl, trialkylstannyl, and the like.

Preferably R is one selected from phenyl, furyl, thienyl, oxazolyl, isoxazolyl, optionally protected aminoisoxazolyl, thiazolyl, optionally protected aminothiazolyl, thiadiazolyl, and aminothiadiazolyl. An optionally protected aminothiazolyl is more preferable.

$R^1$ as halogen is fluorine or chlorine, especially chlorine. Preferably $R^1$ is hydrogen.

The alkylene part in $R^2$ is lower alkylene, preferably 1 to 3 C alkylene, especially methylene.

$R^5$ as a substituent of cephalosporins can be, among others, hydroxy, alkanoyloxy, halogen, alkoxy, alkylthio, alkenylthio, alkyl (e.g., methyl), alkenyl (e.g., vinyl, cyanovinyl, trifluoropropenyl), substituted methyl, or the like which are well known 3-substituents of cephalosporins. Here, the substituent in the said substituted methyl can be pyridinio, substituted pyridinio, halogen, hydroxy, alkoxy, acyloxy (e.g., acetoxy, carbamoyloxy), alkylthio, haloalkylthio, cyanoalkylthio, heterocyclic thio (e.g., triazolylthio, methyltetrazolylthio, thiadiazolylthio optionally substituted by amino, aminomethyl, alkoxy, or methyl), triazolyl, tetrazolyl, or the like. The alkyl part is preferably methyl. Preferably $R^5$ is hydrogen, vinyl, carbamoyloxymethyl, tetrazolylthiomethyl, or thiadiazolylthiomethyl.

$R^3$ or $R^6$ as a carboxy-modifying group is preferably an ester forming group or salt forming atom or group each useful as a carboxy-protecting group or one for a medical derivative.

Preferably X is sulfur.

The said carboxy-protecting group is known in penicillin and cephalosporin fields as it can be introduced and removed without adverse effect on other parts of the molecule. Representative are an inorganic salt (e.g., lithium, sodium, potassium, magnesium, calcium, aluminum, or ammonium salt), organic base salt, for example, alkylamine salt (e.g., ethylamine, diethylamine, triethylamine, piperidine, morpholine, N-methylmorpholine salt), aromatic amine salt (e.g., aniline, dimethylaniline salt), aromatic base salt (e.g., pyridine, picoline, lutidine, nicotinamide, quinoline salt), optionally substituted 1 to 8 C alkyl ester (e.g., methyl, methoxymethyl, ethoxymethyl, ethyl, methoxyethyl, trichloroethyl, iodoethyl, propyl, isopropyl, ethoxyethyl, methylthioethyl, methanesulfonylethyl, methanesulfonylmethyl, butyl, isobutyl, t-butyl, hexyl ester), 7 to 15 C aralkyl ester (e.g., benzyl, methylbenzyl, dimethylbenzyl, methoxybenzyl, ethoxybenzyl, nitrobenzyl, aminobenzyl, phenethyl, diphenylmethyl, trityl, phthalidyl, phenacyl, di-t-butyl-hydroxybenzyl ester), 6 to 12 C aryl ester (e.g., phenyl, tolyl, diisopropylphenyl, xylyl, trichlorophenyl, indanyl ester), 3 to 12 C silyl ester (e.g., trimethylsilyl, t-butyldimethylsilyl, dimethylmethoxysilyl ester), 3 to 12 C stannyl ester (e.g., trimethylstannyl ester), 1 to 12 C N-hydroxyamino ester (ester with e.g., acetone oxim, acetophenone oxim, acetalaoxim, N-hydroxysuccinimide, N-hydroxyphthalimide), 2 to 7 C alkenyl ester (e.g., vinyl, propenyl, allyl ester), and the like. Anhydrides with carbonic or carboxylic acid, reactive amides, and the like are equivalent caboxy-protecting group. Said protecting part may further be substituted.

Preferably $R^3$ and $R^6$ as carboxy protecting groups are hydrogen, sodium, potassium, methyl, t-butyl, phenyl, indanyl, benzyl, cyanobenzyl, halobenzyl, methylbenzyl, nitrobenzyl, phenylbenzyl, or the like.

The protecting group is absent in objective products. So, its structure has in itself no specific means, as far as the group serves well for the protection and thus it can be replaced by a wide variety of equivalent groups.

Especially useful carboxy derivatives are medically available ones including light metal salts and pharmaceutically acceptable esters. The preferred light metals are those forming physiologically acceptable ions and belonging to the 1st to 3rd group, 2nd to 4th periods of the Periodical Table. Lithium, sodium, potassium, magnesium, calcium, aluminum, and the like are preferable. The pharmacological esters show antibacterial potency on administering orally or parenterally and including well known 3 to 12 C 1-substituted alkyl esters, for example, alkanoyloxyalkyl esters (e.g., acetoxymethyl, acetoxyethyl, propionyloxyethyl, pivaloyloxymethyl, pivaloyloxyethyl, tetrahydrofuryl, tetrahydropyranyl ester), 3 to 8 C alkoxyformyloxyalkyl esters (e.g., ethoxycarbonyloxyethyl ester), 7 to 15 C substituted aralkyl esters (e.g., phenacyl, phthalidyl ester), 6 to 12 C substituted aryl esters (e.g., phenyl, xylyl, indanyl ester), and 2-alkenyl esters (e.g., allyl, 2-oxo-1,3-dioxclenylmethyl ester).

Both of the geometric isomers at the double bond in the 7-side chain are antibacterials. Among them, those having the R and $R^1$ in the cis position are more potent antibacterials. The other geometric isomers (trans) are useful also as an intermediate for preparing the corresponding cis isomer.

Some of the representative Compounds (I) of this invention are listed below. These should not be taken as an exhaustive listing of the compounds of this invention.

7beta-[2-(2-aminothiazol-4-yl)-4-carboxy-2-butenoylamino]-3-cephem-4-carboxylic acid,
7beta-[2-(2-aminothiazol-4-yl)-4-carboxy-2-butenoylamino]-3-methyl-3-cephem-4-carboxylic acid,
7beta-[2-(2-aminothiazol-4-yl)-4-carboxy-2-butenoylamino]-3-vinyl-3-cephem-4-carboxylic acid,
7beta-[2-(2-aminothiazol-4-yl)-4-carboxy-2-butenoylamino]3-trifluoropropenyl-3-cephem-4-carboxylic acid,
7beta-[2-(2-aminothiazol-4-yl)-4-carboxy-2-butenoylamino]-3-acetoxymethyl-3-cephem-4-carboxylic acid,
7beta-[2-(2-aminothiazol-4-yl)-4-carboxy-2-butenoylamino]-3-carbamoyloxymethyl-3-cephem-4-carboxylic acid,
7beta-[2-(2-aminothiazol-4-yl)-4-carboxy-2-butenoylamino]-3-methoxymethyl-3-cephem-4-carboxylic acid,
7beta-[2-(2-aminothiazol-4-yl)-4-carboxy-2-butenoylamino]-3-methylthiomethyl-3-cephem-4-carboxylic acid,
7beta-[2-(2-aminothiazol-4-yl)-4-carboxy-2-butenoylamino]-3-cyanomethylthiomethyl-3-cephem-4-carboxylic acid,
7beta-[2-(2-aminothiazol-4-yl)-4-carboxy-2-butenoylamino]-3-pyridiniomethyl-3-cephem-4-caroboxylate,
7beta-[2-(2-aminothiazol-4-yl)-4-carboxy-2-butenoylamino]-3-triazolylthiomethyl-3-cephem-4-carboxylic acid,
7beta-[2-(2-aminothiazol-4-yl)-4-carboxy-2-butenoylamino]-3-thiadiazolylthiomethyl-3-cephem-4-carboxylic acid,
7beta-[2-(2-aminothiazol-4-yl)-4-carboxy-2-butenoylamino]-3-methyltetrazolylthiomethyl-3-cephem-4-carboxylic acid,
7beta-[2-(2-aminothiazol-4-yl)-4-carboxy-2-butenoylamino]-3-methoxy-3-cephem-4-carboxylic acid,
7beta-[2-(2-aminothiazol-4-yl)-4-carboxy-2-butenoylamino]-3-chloro-3-cephem-4-carboxylic acid,
7beta-[2-(2-aminothiazol-4-yl)-4-carboxy-2-butenoylamino]-3-fluoroethylthio-3-cephem-4-carboxylic acid,
7beta-[2-(2-aminothiazol-4-yl)-4-carboxy-2-butenoylamino]-3-trifluoroethylthio-3-cephem-4-carboxylic acid,
7beta-[2-(2-aminothiazol-4-yl)-5-carboxy-2-pentenoylamino]-3-cephem-4-carboxylic acid,
7beta-[2-(2-aminothiazol-4-yl)-6-carboxy-2-hexenoylamino]-3-cephem-4-carboxylic acid,
7beta-[2-(2-aminothiazol-4-yl)-4-carboxy-2-pentenoylamino]-3-cephem-4-carboxylic acid,
7beta-[2-(2-aminothiazol-4-yl)-4-carboxy-4-methyl-2-pentenoylamino]-3-cephem-4-carboxylic acid, and
7beta-[2-(2-aminothiazol-4-yl)-4-carboxy-3-chloro-2-butencylamino]-3-cephem-4-carboxylic acid.

Some compounds closely related to Compounds (I) are disclosed in Japanese patent publication Kokoku 10,996/1967, Kokai 57-93982, and Belgian Pat. Nos. 816,408 and 888,389. These are not superior to Compounds (I) in their antibacterial activity, enteral or parenteral absorbability, excretion, or the like characteristics.

Compounds (I) are antibacterials against aerobic Grampositive bacteria (e.g., *Bacillus cereus, Bacillus subtilis, Corynebacterium diphtheriae, Staphylococcus aureus, Staphylococcus epidermidis, Streptococcus pneumoniae, Streptococcus pyogenes, Streptococcus viridans,* enterococci) and Gramnegative bacteria (e.g., *Citrobacter diversus, Citrobacter freundii, Enterobacter aerogenes, Enterobacter cloacae, Escherichia coli, Haemophilus influenzae, Klebsiella pneumoniae, Neisseria gonorrhoeae, Neisseria meningitidis, Proteus mirabilis, Proteus morganii, Proteus vulgaris, Providencia rettgeri, Providencia stuartii, Pseudomonas aeruginos, Salmonella paratyphi, Salmonella typhi, Serratia marcescens, Shigella sonnei, Yersinia enterocolitica*), including anaerobic bacteria (e.g., *Bacteroides fragilis, Clostridium difficile, Clostridium perfringens, Eubacterium lentum, Fusobacterium nucleatum, Propionibacterium* spp, peptostreptococci, *Veillonella* spp.).

Especially, high anti-Gram-negative potency, high absorption, excretion, distribution, and the like are remarkable. As a medicine for preventing or treating a bacterial infection, Compound (I) is administered orally, parenterally, or topically at a daily dose of 10 micrograms to 6 grams, if required formulating with conventional additives or coacting substances, e.g., other antibacterials.

They are useful as bacteriocidal, bacteriostatic, disinfecting, or antiperishable agents and useful for treating of preventing human, veterinary, or poultry infections caused by sensitive Gram-positive bacteria or Gram-negative bacteria, including anaerobic bacteria. Further, they are useful as bacterial growth inhibitors on human, animal, plant, or perishable subjects, human or animal growth promoting additives in foodstuff, or as an agents for testing sensitivity of bacteria to the antibacterial (I).

Protected compounds (I) are also useful as starting materials for synthesizing other antibacterials (I).

This invention also provides a method for treating or preventing human or veterinary bacterial infections (e.g., abscess, bronchitis, dermatitis, ear infections, empyema, enteritis, gastroenteritis, nasopharyngitis, osteomyelitis, pneumonitis, pneumonia, pustulosis, pyelonephritis, respiratory tract infections, rhinitis, septicemia, tonsillitis, ulceration, urinary tract infections, wound and soft tissue infections) caused by sensitive bacteria by administering an effective amount of Compound (I) at a typical daily dose of 10 micrograms to 1 gram externally, 0.2 to 5 grams intravenously, or 0.1 to 2 grams orally at an interval of 3 to 12 hours depending on the infecting bacteria and condition of the patient, if required formulating with a conventional additive.

Compound (I) as carboxylic acid or its light metal salt can be injected or infused intravenously, intramuscularly or subctaneously (as e.g., injection, pellet), or given orally (as oral preparations, e.g., capsule, dry syrup, emulsion, granules, powder, solution, suspension, tablet, troche), if required in admixture with an excipient (e.g., emulsifying agent). A pharmacological ester can be given intravenously, intramuscularly, subctaneously, orally, externally, or topically (as e.g., ear, nasal, or ocular drug, ointment, inhalant, injection, pap preparation, spray, suppository).

When R is 2-amino-4-thiazolyl, $R^2$ is methylene, $R^1$, $R^3$, $R^4$, and $R^6$ are hydrogens, and $R^5$ is hydrogen, methyl, methoxymethyl, carbamoyloxymethyl, methylthiomethyl, cyanomethylthiomethyl, vinyl, fluoropropenyl, methoxy, chlorine, fluoroethylthio, or trifluoroethylthio, Compound (I) is absorbed orally as well as subcutaneously. Its pharmaceutically acceptable esters are also absorbed through the digestive organs.

Further, this invention provides an antibacterial pharmaceutical composition containing Compound (I) in various enteral or parenteral dosage forms solely or in admixture with carriers or coacting substances. The compositions may contain 0.01 to 99% of Compound (I) dissolved, dispersed, or suspended in solid or liquid pharmaceutical carriers.

The compositions may be solid preparations (e.g., capsule, dry syrup, granule, pellet, pill, powder, suppository, troche, tablet) or liquid preparations (e.g., dispersion, elixir, emulsion, inhalant, injection, ointment, suspension, syrup, solution from ampoule or vial containing crystals, lyophilized material, or powder). They can be flavored or colored, and capsules, granules, and tablets may be coated. They can be in a unit dosage form.

The carriers are harmless to both the Compound (I) and patients. Representative examples of such carriers are, among others, for solids, binders (e.g., acacia, carboxymethylcellulose, gelatin, glucose, polyvinylpyrrolidone, sodium alginate, sorbitol, starch, syrup, tragacanth), bulking agents (e.g., bentonite, calcium carbonate, calcium phosphate, glycine, kaolin, lactose, polycarboxymethylene, salt, sorbitol, starch, sugar, talc), diluents (e.g., calcium carbonate, kaolin, lactose, starch, sucrose), disintegrators (e.g., agar, carbonates, sodium laurylsulfate, starch), lubricants (e.g., boric acid, cacao oil, magnesium stearate, paraffin, polyethylene glycol, silica, sodium benzoate, stearic acid, talc), and wetting agents (e.g., hydroxypropyl cellulose); for solutions, solvents (e.g., alcohol, buffer, methyl cleate, peanut oil, sesame oil, water), emulsifying agents (e.g., acacia, lethicin, sorbitan monooleate), suspending agents (e.g., aluminum stearate gel, carboxymethyl cellulose, gelatin, glucose, hydrogenated fats, hydroxyethylcellulose, methyl cellulose, sorbitol, sugar syrup), buffers, dispersing agents, and solubilizing agents; and for both, preservatives (e.g., methyl or ethyl p-hydroxybenzoate, sorbic acid), absorption promoters (e.g., glycerin mono- or di-octanoate), antioxidants, aromatic substaces, analgesics, edible coloring agents, stabilizing agents, and the like.

All of above pharmaceutical preparations can be prepared in conventional manner.

This invention also provides Carboxyalkenoic acid (10) useful as an intermediate for preparing the said Compound (I)

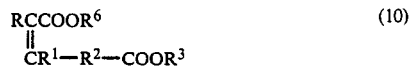

(wherein R, and $R^1$ to $R^6$ are as defined for Compound (I).

In the formula above, examples of the preferred R are phenyl, thienyl, aminoisoxazolyl, thiadiazolyl, aminothiadiazolyl, and aminothiazolyl, said amino can be protected with benzyloxycarbonyl, methylbenzyloxycarbonyl, t-butoxycarbonyl, methoxyethoxymethyl, formyl, chloroacetyl, benzylidene, dimethylaminomethylidene, or the like; preferably $R^1$ is hydrogen; preferably $R^2$ is 1 to 3 C optionally branched alkylene, especially methylene; and examples of preferred $R^3$ and $R^6$ are the same or different groups selected from hydrogen, methyl, ethyl, t-butyl, trichloroethyl, benzyl, methylbenzyl, diphenylmethyl, trityl, and the like.

Compounds of this invention can be synthesized, for example, by the following methods:

(1) Salt formation

Compound (I) having carboxy on the cephem nucleus at position 4 or in the 7-substituent can form a light metal salt (I) by reacting with a base or by an exchange reaction with the corresponding light metal salt of other carboxylic acid. The procedure can be that conventional in the art, e.g., by neutralizing the free acid (with a base, e.g., light metal hydroxide, carbonate, or hydrogen carbonate) and evaporating the solvent, or by treating with light metal lower carboxylate in a polar organic solvent (e.g., alcohol, ketone, ester) and then adding a sparingly dissolving less polar solvent to separate the salt. The solvent may be removed by filtering.

(2) Deprotection of carboxy-protecting groups etc,

A protected-carboxy in Compound (I) can conventionally be deprotected, for example, as follows:

(a) A highly reactive ester of anhydride as a carboxy-protecting group can be deprotected by contacting in an aqueous solvent with an acid, base, buffer solution, or ion exchange resin. When its reactivity is insufficient, one can increase it in a conventional manner to deprotect more easily (e.g., by activating of a trichloroethyl ester with metal and acid; p-nitrobenzyl ester with hydrogen and catalyst (e.g., palladium, nickel), dithionate, or metal and acid; and phenacyl ester with irradiation).

(b) An aralkyl ester can be deprotected by a conventional catalytic reduction with hydrogen in the presence of a catalyst (e.g., platinum, palladium, nickel).

(c) An aralkyl, cyclopropylmethyl, sulfonylethyl, or the like ester can be deprotected by solvolyzing [with a mineral acid, Lewis acid (e.g., aluminium chloride, tin chloride, titanium tetrachloride), sulfonic acid (e.g., methanesulfonic acid, trifluoromethanesulfonic acid), strong carboxylic acid (trifluoroacetic acid), or the like], if required in the presence of a cation scavenger.

An amino-protecting group in Compound (I) can conventionally be deprotected, for example, as follows: substituted alkyl (e.g., tetrahydropyranyl), aralkyl group (e.g., trityl), alkylidene, aralkylidene, alkanoyl (e.g. formyl), trialkylsilyl, trialkylstannyl, or the like can be deprotected with an aqueous or nonaqueous acid; an alkoxyformyl (e.g., t-butoxycarbonyl), aralkoxyformyl (e.g., benzyloxycarbonyl, methylbenzyloxycarbonyl), aralkyl (e.g., trityl), or the like can be deprotected with a Lewis acid in the presence of an acid scavenger; haloalkoxylcarbonyl (e.g., trichloroethyl, iodoethoxycarbonyl), aralkoxycarbonyl (e.g., benzyloxycarbonyl), or the like can be deprotected by reduction; and phenylthio or acyl (e.g., alkanoyl, succinyl, phthaloyl) can be deprotected with a base.

Deprotection of other protecting groups for hydroxy or the like functional groups in Compound (I) can be carried out according to methods well known in the field of penicillin and cephalosporin chemistry as described in various scientific and patent publications.

(3) Amidation

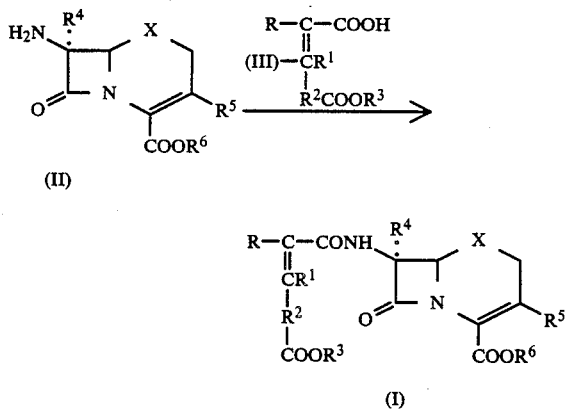

A conventional reaction of Amine (II) or its reactive derivative with Carboxylic acid (III) or its reactive derivative gives Compound (I) or its derivatives.

The reactive derivative of Amine (II) is that having 7-amino activated by silyl (e.g., trimethylsilyl, methoxydimethylsilyl, t-butyldimethylsilyl), stannyl (e.g., trimethylstannyl), alkylene (as a part of enamino of the amino with e.g., aldehyde, acetone, acetylacetone, acetoacetate, acetoacetonitrile, acetoacetanilide, cyclopentanedione, acetylbutyrolactone), alkylidene (e.g., 1-haloalkylidene, 1-haloaralkylidene, 1-alkoxyalkylidene, 1-alkoxyaralkylidene, 1-alkoxy-1-phenoxyalkylidene, alkylidene, aralkylidene), acid (e.g., mineral acid, carboxylic acid, sulfonic acid as a salt of the amino), easily removable acyl (e.g., alkanoyl), or the like, or that protected at other functions of the molecule.

Free acid (III) is reacted in the presence of condensing reagent [carbodiimide (e.g., N,N'-diethylcarbodiimide, N,N'-dicyclohexylcarbodiimide), carbonyl compound (e.g., carbonyl diimidazole), isoxazolinium salt, acylamino compound (e.g., 2-ethoxy-1-ethoxycarbonyl-1,2-dihydroquinoline), etc.].

The reactive derivative of Carboxylic acid (III) can be an acid anhydride, e.g., symmetric anhydride or mixed anhydride [with mineral acid (e.g., phosphoric acid, sulfuric acid, hydrohalogenic acid, carbonic half ester), organic acid (e.g., alkanoic acid, aralkanoic acid, sulfonic acid), intramolecular anhydride (e.g., ketene, isocyanate), etc.]. acid halide, reactive ester [enol ester (e.g., vinyl ester, isopropenyl ester), aryl ester (e.g., phenyl ester, halophenyl ester, nitrophenyl ester), heterocyclic ester (e.g., pyridyl ester, benzotriazolylester), an ester with N-hydroxy compound, diacylhydroxylamine ester (e.g. N-hydroxysuccinimide ester, N-hydroxyphthalimide ester), thioester (e.g., aralkyl thiol ester, heterocyclic thiol ester) or the like], or reactive amide [aromatic amide (amide with e.g., imidazole, triazole, 2-ethoxy-1,2-dihydroquinoline), diacylanilide]. The acid scavenger to be used with the said derivative is, for example, inorganic base (e.g., oxide, hydroxide, carbonate, hydrogen carbonate, of alkali metal or alkaline earth metal, etc.), organic base (e.g., tertiary amine, aromatic base), oxirane, (e.g., alkylene oxide, aralkylene oxide), pyridinium salt (e.g., tripyridiniumtriazine trichloride), adsorbent (e.g., Celite), or the like.

(4) Introduction of 3function

Compound (I) having 3-nucleophile substituted-methyl can be prepared by reacting an analog of Compound (I) having a leaving group-substituted methyl at the 3-position on the cephem ring with a heterocyclic thiol, aromatic base, or its reactive derivatives. Here, the leaving group can be, among others, halogen, sulfonyloxy, alkanoyloxy, dihaloalkanoyloxy, trihaloacetoxy, or the like. The said reactive derivative of thiol can be, among others, alkali metal salt, ammonium salt, carboxylate ester, or the like. The reaction can be carried out well in a dry or wet solvent at 0° C. to 60° C. This reaction can be promoted with a dehydrating reagent, phosphoryl chloride compound, rhodanate, or the like.

Compound (I) having 3-acyloxymethyl (e.g., alkanoyloxymethyl, carbamoyloxymethyl) can be made from the corresponding 4-protected carboxy-3-hydroxymethyl-3-cephem derivative by the action of an acylating reagent for introducing the corresponding acyl group.

Compound (I) having no carbon linked to the 3 position can be made from the corresponding 3-hydroxy-3-cephem or its oxo form, for example, by activating the 3-hydroxy (e.g., acylating or halogenating), and then substituting it with a nucleophilic reagent to give a 3-nucleophile substituted compound; a basic or thermal elimination reaction of the corresponding 3-(hydroxy, acyloxy, or halo) cepham compounds or a reduction of 3-(acyloxy or halo)-3-cephem compounds to give a 3-hydrogen-3-cephem compound; or the like conventional 3-modification.

(5) Isomerization at the 7-side chain double bond

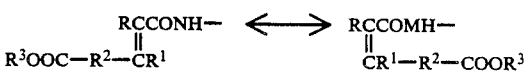

The said geometric isomers are interconvertible by isomerization. This reaction is preferably carried out in a protic solvent by the action of acid, base, or light. The acid can be a mineral acid (e.g., hydrochloric acid, sulfuric acid, phosphoric acid), carboxylic acid (e.g., formic acid, trifluoroacetic acid), sulfonic acid (e.g., methanesulfonic acid, benzenesulfonic acid), or the like. The base can be inorganic base (e.g., sodium hydroxide, sodium hydrogen carbonate, potassium carbonate), organic base (e.g., triethylamine, potassium t-butoxide), or the like.

Compound (I) wherein $R^2$ is 1 to 3 C alkylene easily isomerizes under various conditions.

In a typical condition, Compound (I) as free carboxylic acid is dissolved in water at pH 8, acidified to pH 0 to 1, kept at 0° C. to 100° C. for 1 to 10 hours to obtain an epimic mixture. Thermally stable isomer is in trans form. Usual separation (e.g., crystallization, precipitation, high precision liquid chromatography, adsorption and elution) gives the geometric isomers in a pure form.

(6) Other synthetic methods (a) Sulfoxide formation:—Cephem compound (I) is conventionally oxidized with an oxidizing reagent (e.g., hydrogen peroxide, percarboxylic acid, iodobenzene dichloride) in an inert solvent at 0° to 60° C. for 0.2 to 5 hours to give the corresponding Cephem-1-oxide (I).

(b) Sulfoxide reduction:—Cephem-1-oxide compound (I) is reduced conventionally with a trivalent phosphorus compound, lower valent metal compound, hydrogen iodide, or the like in an inert solvent at 0° to 80° C. for 0.1 to 10 hours giving the corresponding Cephem compound (I).

(c) Double bond migration:—The 2-double bond of the corresponding 2-cephem compound is conventionally migrated with base at 0° to 80° C. for 1 to 10 hours to give 3-Cephem compound (I).

(d) Ring closure:—Compound (I) may be synthesized by a conventional ring closure reaction forming a heterocyclic R group in a manner analogous to those described above under the section of (7) Synthesis of the side chain acids.

(7) Synthesis of the side chain fragment acids

The 7side chain acids are novel compounds prepared by Wittig type reaction of Formylacetate (IV) or its enol or acetal with Alkylidenetriarylphosphorane (V) by heating, e.g., at 30° C. to 120° C. for 1 to 10 hours, to give Nonconjugated ester (VI) the double bond of which migrates to give Conjugate ester (VII):

Representative synthesis of the side chain carboxylic acids are given under the section of Preparations.

(8) Reaction Conditions

The said reaction (1) to (7) can usually be carried out at $-60°$ C. to 120° C., preferably at $-20°$ C. to 80° C. for 10 minutes to 10 hours depending on the type of reaction. These are done in a solvent. Other conventional conditions (e.g., stirring, shaking, inert gas sealing, drying) may be used.

Examples of typical reaction solvents are hydrocarbons (e.g., pentane, hexane, octane, benzene, toluene, xylene), halohydrocarbons (e.g., dichloromethane, chloroform, carbon tetrachloride, dichloroethane, trichloroethane, chlorobenzene), ethers (e.g., diethyl ether, methyl isobutyl ether, dioxane, tetrahydrofuran), ketones (e.g., acetone, methyl ethyl ketone, cyclohexanone), esters (e.g., ethyl acetate, isobutyl acetate, methyl benzoate), nitrohydrocarbons (e.g., nitromethane, nitrobenzene), nitriles (e.g., acetonitrile, benzonitrile), amides (e.g., formamide, acetamide, dimethylformamide, dimethylacetamide, hexamethylphosphorotriamide), sulfoxides (e.g., dimethyl sulfoxide), carboxylic acids (e.g., formic acid, acetic acid, propionic acid), organic bases (e.g., diethylamine, triethylamine, pyridine, picoline, collidine, quinoline), alcohols (e.g., methanol, ethanol, propanol, hexanol, octanol, benzyl alcohol), water, and other industrial solvents and mixtures thereof.

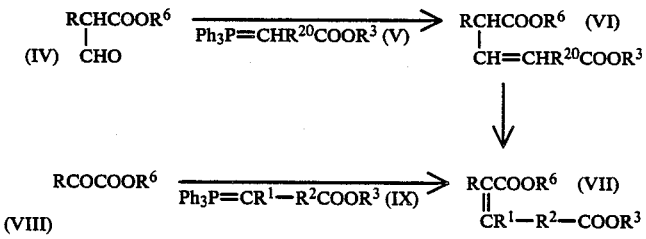

(wherein and $R^{20}$ is alkylene or a single bond) or of Oxalate (VIII) with Alkylidenetriarylphosphorane (IX), e.g., at 30° C. to 120° C. for 1 to 10 hours to give Conjugate ester (VII).

alternatively, it is produced by a ring closure of Haloacetylcarboxylic acid (X) with optionally N-protected thiourea (XI) in alcohol at 30° C. to 90° C. for 1 to 5 hours giving Aminothiazole ester (XII):

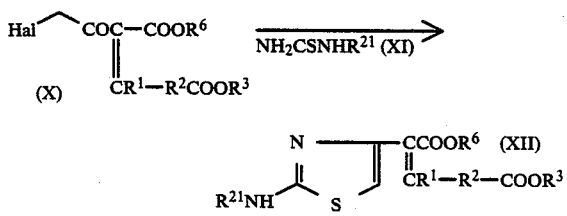

(wherein $R^{21}$ is hydrogen or amino protecting group).

When $R^3$ and/or $R^6$ of Conjugated acid (VII) or (XII) is a carboxy protecting group, it may be deprotected conventionally by treating with acid, base, Lewis acid and cation scavenger, hydrogen and catalyst, or the like to give the corresponding free acid, preferably in an inert solvent at $-60°$ C. to 100° C. for 1/6 to 10 hours.

(9) Work up

The products can be obtained from a reaction mixture by removing contaminants (e.g., solvents, unreacted starting materials, by-products) by a conventional method (e.g., extracting, evaporating, washing, concentrating, precipitating, filtrating, drying), and isolating the product by a usual work up (e.g., adsorbing, eluting, distilling, precipitating, separating, chromatographing), or a combination of said procedures.

(10) Oral availability

Some compounds (I) having methylene as $R^2$ are absorbed well through the digestive organs and are available as oral cephalosporins. Especially efficient are those having 2-aminothiazol-4-yl as R, hydrogen as $R^3$ and $R^6$, and hydrogen, vinyl, cyanovinyl, trifluoropropenyl, acetoxymethyl, carbamoyloxymethyl, or thiadiazolylthiomethyl as $R^5$ and salts of these. It is to be noted that compounds (I) having a single bond, dimethylene, or trimethylene as $R^2$ or that having no carboxylic 7beta-side chain are practically unabsorbed enterally. A compound having amino in R can form a salt by mixing with an acid, e.g., mineral acid (e.g. HCl), carboxylic acid (TFA).

EXAMPLES

Following examples illustrate the embodiments of this invention.

In the Examples, "part" shows part by weight and "equivalent" shows molar equivalent of the beta-lactam starting material. Symbols "cis" and "trans" show relative position of amido and carboxylic substitutents attaching to the side chain double bond. Physicochemical constants of the products are summarized in Tables in which IR shows cm$^{-1}$ value, NHR shows δ-value, and J value shows coupling constants in Hz scale. In NMR of a geometric isomer mixture, signals splitting into two or more are shown by chemical shifts separating with comma and splitting number and "X" before multiplicity mark.

Usually the reaction mixture is, if required after adding a solvent (e.g., water, acid, dichloromethane), washed, dried, and concentrated, and the product is separated. All concentrating are done in reduced pressure.

(Abbreviations) AOM=acetoxymethyl; BH=diphenylmethyl; Bu=butyl; BOC=t-butoxycarbonyl; Bzl=benzyl; Cbz=benzyloxycarbonyl; circle in a hetero ring of the structural formula=the ring is aromatic; exo=3,4-double bond position isomer in the 7-side chain acyl; Me=methyl; MEM=methoxyethoxmethyl; Ph=phenyl; PMB=p-methoxybenzyl; PNB=p-nitrobenzyl; and POM=pivaloyloxymethyl.

EXAMPLE 1

(Sodium Salt)

(1) A solution of carboxylic acid (1) in Table 2 (1 g) in aqueous 0.5% sodium hydrogen carbonate (6 ml) adjusted to pH 7 with hydrochloric acid is washed with ethyl acetate, desalted, and poured into a 10 ml vial. This is lyophilized conventionally to give the corresponding sodium salt (2) as powder.

(2) Similarly, to a suspension of carboxylic acid (I) (1 g) of Table 2 in water is added aqueous sodium carbonate to make a solution of pH 6.5. The solution is desalted and poured into 10 ml vials, and lyophilized to give a sodium salt preparation same to above.

(3) The sodium salt (1 g) produced under sterile condition is dissolved in sterile water (4 g) and is given twice a day orally or intravenously to a patient suffering from *Staphylococcus aureus* infection for treating said disease.

(4) Each one of the carboxylic acids on Table 2 are dissolved in aqueous sodium hydrogen carbonate and assayed as the sodium salts for MIC by the standard method of Japan Society of Chemotherapy to give values of 3.1 to 0.2 microgram/ml against *Streptococcus pyogenes* C-203 and 0.8 to 0.025 microgram/ml against *Escherichia coli* H.

EXAMPLE 2

(Amidation)

A 7-beta-amino compound (2) (1 equivalent) is treated with carboxylic acid corresponding to the 7-beta-side chain (3) or its reactive derivative to give amide (1), for a method as exemplified below:

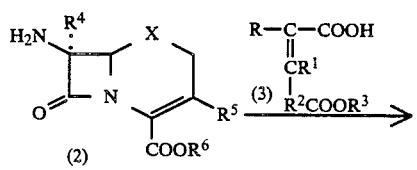

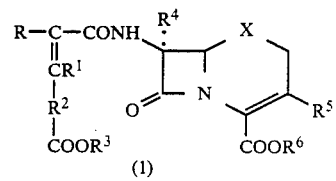

(1) In a mixture of dichloromethane (10 volumes), 2-ethoxy-1-ethoxycarbonyl-1,2-dihydroquinoline (1.1 equivalents), N,N'-dicyclohexylcarbodiimide (1.1 equivalents), pyridine (1.5 equivalents), and carboxylic acid (3) (1.1 equivalents), stirred for 1 to 6 hours at 0° C. to room temperature.

(2) In a mixture of ethyl acetate (10 volumes), di-2-pyridyl disulfide (1.1 equivalents), triphenylphosphine (1.1 equivalents), and carboxylic acid (3) (1.1 equivalents), stirred for 2 to 6 hours at 10° to 50° C.

(3) In a mixture of dichloromethane (3 volumes), 1,3,5-tripyridiniumtriazine trichloride (4 equivalents), and carboxylic acid (3) (1.1 equivalents), stirred for 1 to 5 hours at −10° to 10° C.

(4) In a mixture of carbon tetrachloride (30 volumes), 4-methylmorpholine (1.5 equivalents), trisdiethylaminophosphine (1.1 equivalents) and carboxylic acid (3) (1.1 equivalents), kept at −20° to 10° C. for 1 to 5 hours.

(5) In a mixture of chloroform (10 volumes) and dimethoxyethane (10 volumes), triethylamine (1.5 moles), and a mixed anhydride of carboxylic acid (3) and isobutoxyformic acid, stirred at a temperature between −5° to 10° C. over a 30 minutes and 6 hours time.

(6) In a mixture of ethyl acetate (10 volumes), 1,2-dichloroethane (10 volumes), 4-methylmorpholine (1.5 equivalents), and the symmetric anhydride of carboxylic acid (3) (1.1 equivalents), refluxed for 10 minutes to 2 hours.

(7) In a mixture of dichloromethane (10 volumes), pyridine (1.5 equivalents), and mixed anhydride of carboxylic acid (3) and methanesulfonic acid (1.1 equivalents), stirred for 1 to 3 hours at between −70° C. and room temperature.

(8) In a mixture of ethyl acetate (10 volumes), pyridine (1.5 equivalents) and a mixed anhydride of diethyl hydrogen phosphate and carboxylic acid (3) (1.5 equivalents), stirred at 0° C. to 10° C. for 1 to 5 hours.

(9) In a mixture of ethyl acetate (10 volumes), dichloromethane (10 volumes), N-methylmorpholine (1 equivalent), and mixed anhydride of carboxylic acid (3) and dichlorophosphoric acid (1.1 equivalents), stirred for 1 to 3 hours at 0° C. to room temperature.

(10) In a mixture of lutidine (1.5 equivalents), dichloromethane (10 volumes), and the mixed anhydride (1.1 to 2 equivalents) of carboxylic acid (3) and monochlorophospheoric acid dimethylamide, stirred for 1 to 4 hours at 0° to 30° C.

(11) In a mixture of dichloromethane (5 volumes), trifluoroacetic anhydride (1.5 equivalents), pyridine (3 equivalents), and carboxylic acid (3) (1.5 equivalents), stirred for 1 to 5 hours at 0° C. to room temperature.

(12) In a mixture of dichloromethane (10 volumes), bromide of diethyl hydrogen phosphate (1.2 equivalents), 4-methylmorpholine (2.5 equivalents), and carboxylic acid (3) (1.2 equivalents), stirred for 1 to 3 hours at 0° C. to room temperature.

(13) Amine (2) having carboxy at position 4 of the cephem ring is dissolved in aqueous (10 volumes) sodium hydrogen carbonate (2.5 equivalents). Carboxylic acid (3) chloride (1.1 equivalents) is dropwise added thereto. The mixture is kept at −5° C. to room temperature for 30 minutes to 2 hours.

(14) Amine (2) having carboxy at position 4 of the cephem ring is treated with trimethylsilyl chloride and triethylamine (1.2 equivalents each), and then treated with pyridine (4 equivalents) and carboxylic acid (3) chloride (1.1 equivalents) at −30° C. for between 30 minutes and 2 hours, and then the resulting silyl ester is hydrolyzed with acid.

(15) In a solution of picoline (4 equivalents) and carboxylic acid (3) chloride (1.2 equivalents) in dichloromethane (20 volume) stirred at 0° C. to −30° C. over 30 minutes and 2 hours.

(16) In a mixture of dimethylformamide (2 volumes) and ethyl acetate (10 volumes), stirred with triethylamine (1.1 equivalents) and carboxylic acid (3) chloride (1.1 equivalents) at 0° C. to 20° C. for between 30 minutes and 3 hours.

(17) In a mixture of dichloromethane (30 volumes), cyanuric chloride (1.1 equivalents), pyridine (4 equivalents), and carboxylic acid (3) (1.1 equivalents), stirred for 5 minutes to 2 hours at −30° C. to 10° C.

(18) In a mixture of dichloromethane (3 volumes), phosphorus oxychloride (1.1 equivalents), triethylamine (1.5 equivalents), and carboxylic acid (3) (1.1 equivalents), stirred for 20 minutes to 2 hours at −10° C. to 10° C.

(19) Amine (2) is treated with trimethylsilyl chloride and an acid scavenger to obtain the corresponding N-trimethylsilyl compound, and this is treated with phosphorus oxychloride (1.5 equivalents), carboxylic acid (3) (1.2 equivalents), and dimethylaniline (4 equivalents) in dichloromethane (5 parts) for 30 minutes to 2 hours at 0° C. to room temperature.

(20) in a mixture of dichloromethane (8 volumes), thionylchloride (1.5 equivalents), pyridine (2.5 equivalents), and carboxylic acid (3) (1.1 equivalents), stirred for 1 to 5 hours at −30° to 0° C.

(21) In a mixture of chloroform (3 volumes), toluene (1 volume), picoline (2 equivalents), oxalyl chloride (1 equivalent), and carboxylic acid (3) (1.1 equivalents), stirred for 10 minutes to 2 hours at −50° C. to 10° C.

(22) In a mixture of dichloromethane (20 volumes), pyridine (3 equivalents), and benzotriazolyl ester of carboxylic acid (3) (3 equivalents), stirred for 5 to 30 hours at 10° to 50° C.

(23) In a mixture of dichloromethane (20 volumes), 2-ethoxy-1-ethoxycarbonyl-1,2-dihydroquinoline (2.5 equivalents) and carboxylic acid (3) (2 equivalents), stirred at room temperature for 1 to 15 hours.

(24) In a mixture of dioxane (10 volumes) and phthalimido ester of carboxylic acid (3) (2 equivalents), stirred for 2 to 8 hours at 10° to 50° C.

(25) In a mixture of methyl isobutyl ketone (10 volumes) and succinimido ester of carboxylic acid (3) (1.5 equivalents), stirred for 2 to 9 at 0° to 40° C.

(26) In a mixture of carbonyldiimidazole (1.1 equivalents), tetrahydrofuran (10 volumes), dimethylacetamide (5 volumes), and carboxylic acid (3) (1.1 equivalents), stirred for 1 to 5 hours at 0° C. to room temperature.

(27) In a mixture of dimethylformamide (5 volumes), dimethylaniline (1.3 equivalents), carboxylic acid (3), and the Vilsmeyer reagent made from dimethylformamide (1.1 equivalents), stirred at room temperature for 1 to 5 hours.

(28) In a mixture of dichloromethane (10 volumes), dimethylformamide (5 volumes), N,N'-dicyclohexylcarbodiimide (1.1 equivalents), picoline (1.2 equivalents), and carboxylic acid (3) (1.1 equivalents), reacted for 2 hours to 24 hours.

(29) To a solution of 7-amino-3-(1-methyl-5-tetrazolyl)-thiomethyl-3-cephem-4-carboxylic acid diphenylmethyl ester in dichloromethane (50 parts) containing 2-(2-benzyloxycarbonamido-4-thiazolyl)-4-benzyloxycarbonyl-2-butenoic acid (1 equivalent) is added N,N'-dicyclohexylcarbodiimide (1 equivalent). After stirring for 2 hours at room temperature, the mixture is concentrated. The residue is triturated in ethyl acetate, filtered to remove solid, and purified by column chromatography to give 7-[2-(2-benzyloxycarbonylamino-4-thiazolyl)-4-benzyloxycarbonyl-2-butenoylamino]-3-(1-methyl-5-tetrazolyl)thiomethyl-3-cephem-4-carboxylic acid diphenylmethyl ester. Yield: 90%

(30) To a solution of 7-amino-3-pyridiniomethyl-3-cephem-4-carboxylic acid chloride hydrochloride in a mixture of water (10 parts) and dioxane (15 parts) are added at 0° C. sodium hydrogen carbonate (2 equivalents), 2-(2-benzyloxycarbonylamino-4-thiazolyl)-4-benzyloxycarbonyl-2-butenoic acid (1.2 equivalents), 1-hydroxybenzotriazole (1.2 equivalents), N,N'-dicyclohexylcarbodiimide (1.2 equivalents), and dioxane (5 parts) at 0° C. After stirring at 0° C. for 3.5 hours, the mixture is acidified with 1N-hydrochloric acid (5 parts) and filtered. The filtrate and acetone (50 parts) washing of the solid are combined, purified by silica gel chromatography, and lyophilized to give 7-[2-(2-benzyloxycarbonylamino-4-thiazolyl)-4-benzyloxycarbonyl-2-butenoylamino]-3-pyridiniummethyl-3-cephem-4-carboxylate. Yield: 50.8%.

EXAMPLE 3

(Carboxy-Deprotection)

(1) A solution of a t-butyl, p-methoxypenzyl, or diphenylmethyl ester of Table 1 in a mixture of dichloromethane (0.3 to 3 parts), trifluoroacetic acid (0.3 to 3 parts), and anisole (0.5 to 5 parts) is stirred for 10 minutes to 3 hours at between −10° and 40° C. The solution is concentrated to remove the solvent and reagent. The residue is washed with benzene or ether to give the corresponding acid in 70 to 90% yield.

(2) To a solution of a t-butyl, benzyl, p-methylbenzyl, p-methoxybenzyl, or diphenymethyl ester listed on Table 1 in a mixture of dichloromethane (5 to 9 parts) and anisole (2 to 8 parts) is added aluminum chloride, tin tetrachloride, or titanium tetrachloride (3 to 12 equivalents) at between −10° and 10° C., and the mixture is stirred for 1 to 24 hours. The mixture is washed with diluted hydrochloric acid and water, dried and concentrated to give the corresponding free acid in 80 to 95% yield. t-Butoxycarbonylamino, N-t-butoxycarbonyl-N-methoxyethoxymethylamino, or benzyloxycarbonylamino group when present, is deprotected to give amino group.

(3) To a solution of a t-butyl, benzyl, p-methylbenzyl, p-methoxybenzyl, or dipehnylmethyl ester listed on Table 1 are added 90% formic acid (5 to 6 parts) and anisole (2 3 parts). The mixture is stirred at 50° to 60° C. for 1 to 4 hours to give the corresponding carboxylic acid in 40 to 50% yield.

(4) To a solution of a p-nitrobenzyl ester of Table 1 in dichloromethane (60 parts) are added acetic acid (10 parts) and zinc powder (2 parts). After stirring for 2 hours at 0° C., the mixture is filtered to remove solid, diluted with water, and extracted with dichloromethane. The extract solution is washed with water and extracted with aqueous sodium hydrogen carbonate. The aqueous layer is washed with hydrochloric acid to pH 2, and extracted with dichloromethane. This organic layer is washed with water, dried, and vacuum concentrated to give the corresponding free acid in 60 to 80% yield.

(5) The same ester can be deesterified by shaking with hydrogen in the presence of the same amount of 5% palladium charcoal in dioxane at room temperature for 2 hours.

(6) To a solution of 7-[2-(2-benzyloxycarbonylamino-4-thiazolyl)-4-benzyloxycarbonyl-2-butenoylamino]-3-(1-methyl-5-tetrazolyl)thiomethyl-3-cephem-4-carboxylic acid diphenylmethyl ester in anisole (12 parts) is added aluminum chloride (9 equivalents). After stirring for 4 hours at 0° C., the mixture is neutralized with aqueous 5% sodium hydrogen carbonate, filtered to remove solid, and washed with ethyl acetate. Aqueous layer is acidified with hydrochloric acid, washed with ethyl acetate, and passed through a column of HP 20 or SP 207 (synthetic adsorbent produced by Mitsubishi Chemical K. K.). Adsorbed material is eluted with 80% methanol to afford 7-[2-(2-amino-4-thiazolyl)-4-carboxy-2-butenoylamino]-3-(1-methyl-5-tetrazolyl)thiomethyl-3-cephem-4-carboxylic acid. Yield: 65%.

(7) To a suspension of 7-[2-(2-benzyloxycarbonylamino-4-thiazolyl)-4-benzyloxycarbonyl-2-butenoylamino]-3-pyridinium-methyl-3-cephem-4-carboxylic acid in anisole (2 parts) is added a solution of aluminum chloride (9 equivalents) in anisole (2 parts) at 0° C. After stirring for 3.5 hours, the mixture is acidified with 10% hydrochloric acid and washed with ethyl acetate. Aqueous layer is passed through a column of Diaion HP-20. Adsorbed material is eluted with aqueous 5% acetone and the eluate lyophilized to give 7-[2-(2-amino-4-thiazolyl)-3-carboxymethylacrylamido]-3-pyridiniomethyl-3-cephem-4-carboxylic acid. Yield: 55%.

(8) In a manner similar to that of above (1) to (7), a free carboxy compound of Table 2 are prepared from the corresponding carboxy-protected compound of Table 1.

(9) To a solution of diphenylmethyl 7beta-[2-(2-carbobenzoxyaminothiazol-4-yl)-4-allyloxycarbonyl-2-butenoylamino]-3-cephem-4-carboxylate (3.75 g) (5 mM) in dichloromethane (30 ml) are added 2-ethylhexanoate (1.5 molar equivalents), triphenylphosphine (0.5 equivalents), and tetrakistriphenylphosphine-palladium complex (125 mg). After stirring for 1 hour at 25° C., the mixture is dilute with ether to separate diphenylmethyl 7beta-[2-(2-carbobenzoxyaminothiazol-4yl)-4-sodiooxycarbonyl-2-butenoylamino]-3-cephem-4-carboxylate in 94% yield. This is suspended in water (10 parts) and acidified with aqueous 4% phosphoric acid to separate diphenylmethyl 7beta-[2-(2-carbobenzoxyaminothiazol-4-yl)-4-carboxy-2-butenoylamino]-3-cephem-4-carboxylate.

EXAMPLE 4

(Amino Deprotection)

(1) A solution of a t-butoxycarbonylamino compound listed on Table 1 in a mixture of dichloromethane (0.3 to 3 parts), trifluoroacetic acid (0.3 to 3 parts), and anisole (0.5 to 5 parts) is stirred for 10 minutes to 3 hours at between −10° and 40° C. The solution is concentrated to remove the solvent and reagent. The residue is washed with benzene to give the corresponding amino compound listed on Table 1 or 2 in 70 to 80% yield.

(2) To a solution of a t-butoxycarbonylamino, benzyloxycarbonylamino, methylbenzyloxycarbonylamino, methoxyethoxymethylamino, or tritylamino compound listed on Table 1 (1 part) in a mixture of dichloromethane (5 to 9 parts) and anizole (2to 8 parts) is added aluminum chloride, tin tetrachloride, or ticanium tetrachloride (3 to 12 equivalents) at between −10° and 10° C., and the mixture is stirred for 1 to 24 hours. The mixture is extracted with diluted hydrochloric acid and water, the aqueous layer is passed through a column of HP-20 absorbent to give the corresponding free amino compound listed on Table 1 or 2 in 60 to 80% yield. A t-butyl, benzyl, p-methylbenzyl, p-methoxybenzyl, or diphenylmethyl ester group when present, is deprotected to give free carboxy.

(3) To a solution of a chloroacetamido compound of Table 1 in a mixture of tetrahydrofuran (15 parts) and methanol (15 parts) are added thiourea or N-methyldithiocarbamate (4 equivalents) and sodium acetate (2 equivalents). after one night at room temperature, the mixture is concentrated, diluted with ethyl acetate, washed with saline, dried, and concentrated. The residue is chromatographed to give the corresponding amino compound.

(4) To a solution of a formamido, Schiff base, silylamino, or tritylamino compound listed on Table 1 in formic acid, acetic acid, or ethanol (10 parts) is added 1 to 3N-hydrochloric acid (0.1 to 3 parts), and the mixture is stirred for 1 to 3 hours at room temperature. The reaction mixture is concentrated, diluted with dichloromethane, washed with aqueous sodium hydrogen carbonate and water, dried and concentrated. The residue is purified in a conventional manner to give the corresponding free amino compound listed on Table 1 or 2.

(5) To a solution of a benzyloxycarbonylamino compound listed on Table 1 in a mixture of ethanol and ethyl acetate (30 parts: 1:1) is added 5% palladium charcoal (0.5 parts), and the mixture is shaken under hydrogen until the starting material is consumed. The reaction mixture is filtered to remove solid and concentrated to give the corresponding amino compound listed on Table 1 or 2.

EXAMPLE 5

(Esterification)

($R^3$ and/or $R^6$ =diphenylmethyl)

(1) To a solution of compound (I) in which $R^3$ and/or $R^6$ is hydrogen in a mixture of dichloromethane and methanol (10 weights each) is added diphenyldiazomethane (2 equivalents). After stirring for 1 hour, the mixture is washed with hydrochloric acid and water, dried, and concentrated. The residue is crystallized from ethyl acetate to give the corresponding diphenylmethyl ester.

($R^3$ and/or $R^6$ =POM)

(2) To a solution of compound (I) wherein $R^3$ and/or $R^6$ is potassium in N,N-dimethylformamide (2 to 5 parts) is added iodomethyl pivalate (1 to 2 equivalents) under ice-salt cooling. After 15 minutes to 2 hour's stirring, the mixture is diluted with ethyl acetate, washed with ice water and aqueous sodium hydrogen carbonate, dried, and concentrated in vacuum. The residue is recrystallized from ethyl acetate to give the pivaloyloxymethyl ester of the carboxylic acid of Table 3.

(3) The potassium salt of above section (2) is replaced by sodium salt to give the same products under the same condition.

(4) The pivaloyloxymethyl ester of above section (2) (250 mg), corn starch (150 mg), and magnesium stearate (5 mg) are mixed, granulated, and encapsulated in a conventional manner. This capsule (2 to 3 capsules) are given orally to treat a patient suffering from infection caused by sensitive *E. coli*. ($R^3$ and/or $R^6$=ACN).

(5) In place of iodomethyl pivalate of above (2), iodomethyl acetate is used under the same reaction condition to give the corresponding acetoxymethyl ester of Table 3.

EXAMPLE 6

(Introduction of 3-substituents)

($R^5$=H)

(1) To a solution of a compound listed on Table 1 and having methanesulfonyloxy or chlorine as $R^5$ in dichloromethane (13 parts) are added acetic acid (10 part) and zinc powder (2.5 parts) and the mixture is heated at 50° C. for 5 hours. The reaction mixture is filtered to remove solid, diluted with ethyl acetate, washed with diluted hydrochloric acid, water, aqueous sodium hydrogen carbonate, and water, dried, and concentrated. The residue is purified by silica gel chromatography eluting with a mixture of benzene and ethyl acetate to give the corresponding compound listed on Table 1 or 2 having hydrogen as $R^5$ in 50 to 80% yield.

(2) Above reaction (1) is carried out at room temperature for 5 to 10 hours in the presence of a diluent isopropanol (4 parts) to give the same product in 40 to 60% yield.

(3) To a solution of 7beta-[2-(2-benzyloxycarbonylaminothiazol-4-yl)-4-benzyloxycarbonylbut-2-enoylamino]-3-hydroxycepham-4-carboxylic acid diphenylmethyl ester sulfoxide in dichloromethane (13 parts) are added pyridine (6 equivalents) and acetic anhydride (6 equivalents). After 13 hours' stirring at 0° C., the mixture is mixed with triethylamine (3 equivalents) and stirred for 24 hours. The reaction mixture is washed with water, aqueous sodium hydrogen carbonate, and water, dried, and concentrated to give 7beta-[2-(2-benzyloxycarbonylaminothiazol-4-yl)-4-benzyloxycarbonyl-2-butenoylamino]-3-cephem-4-carboxylic acid dipehnylmethyl ester sulfoxide in 40 to 60% yield.

($R^5$=cyanomethylthiomethyl)

(4) In the manner as given in Preparation B-4 a compound having bromomethyl as $R^5$ is treated with sodium cyanomethyl mercaptide at −65° C. to 70° C. for 2 hours to give the corresponding compound listed on Table 1 having cyanomethylthiomethyl as $R^5$ in 50 to 60% yield.

EXAMPLE 7

(Sulfoxide Reduction)

In a manner similar to that of Preparation B-4 (2) using the same ratio of the reagent and solvents, the corresponding sulfoxide is reduced to give the cephem (sulfide) compounds of Table 1.

EXAMPLE 8

(Double Bond Migration)

A solution of 7beta-[2-(2-t-butoxycarbonylaminothiazole-4-yl)-4-benzyloxycarbonyl-2-butenoylamino]-3-chloro-2-cephem-4-carboxylic acid diphenylmethyl ester is reduced according to the method of Example 6 (1) to induce concomitant double bond migration affording 7beta-[2-(2-aminothiazolyl-4-yl)-4-carboxy-2-butenoylamino]-3-cephem-4-carboxylic acid diphenylmethyl ester in 53% yield.

EXAMPLE 9

(Amine Salt)

To a solution of an amino compound listed on Table 2 in diluted hydrochloric acid is added acetonitrile. The precipitated material is collected by filtration to give the corresponding hydrochloric acid addition salt in good yield.

PREPARATION A (Preparation of Carboxylic Acids

Preparation A-1

2-(2-Benzyloxycarbonylaminothiazol-4-yl)-4-benzyloxycarbonyl-2-butenoic acid (3)

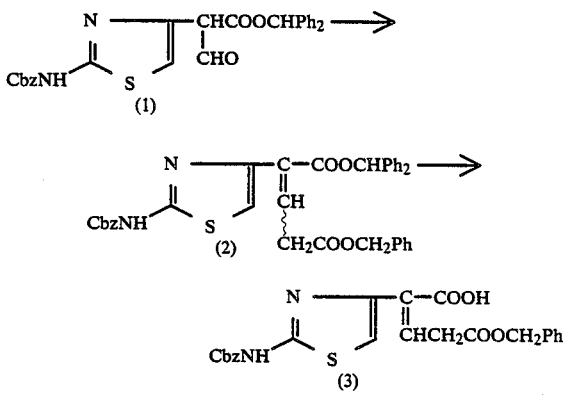

(1) A solution of formylacetate (1) and benzyloxycarbonylmethylidenetriphenylphosphorane (1.3 equivalents) in dioxane or toluene (8 parts) is stirred for 1 to 6 hours at 80° to 120° C. After cooling, the mixture is concentrated, and the residue is purified by silica gel chromatography to give propenedicarboxylate (2). Yield: 85%. This is a mixture of 34% cis and 53% trans geometric isomers which can be separated after repeated chromatography.

IR (CHCl₃) ν: 3410, 1730 cm⁻¹ (trans).
IR (CHCl₃) ν: 3400, 1730 cm⁻¹ (cis).

(2) To a solution of this produce (2) in dichloromethane (10 parts) are added anisole (2 parts) and trifluoroacetic acid (2 parts). After stirring for 2 hours, the reaction mixture is concentrated, and the residue washed with a mixture of ether and hexane to give monobenzyl ester of the dicarboxylic acid (3). Yield: 89%. These geometric isomers can be separated by chromatographs.

NMR (CDCl₃—CD₃OD): δ3.51 (d, J=7 Hz, 2H), 5.13 (s, 2H), 5.26 (s, 2H), 7.06 (s, 1H), 7.0–7.5 (m, 11H) (trans).

NMR (CDCl₃—CD₃OD): δ3.73 (d, J=7 Hz, 2H), 5.13 (s, 2H), 7.10 (s, 1H), 7.0–7.5 (m, 11H) (cis).

In a manner similar to that of Preparation A-1, a butenoic acid diester listed on Table 4 is prepared from the corresponding formylacetate using the same ratios of reactants and solvents at the same temperature for the same reaction time. The obtained ester is, if required, totally or partially deesterified using a conventional reagent, e.g., sodium hydroxide for alkyl esters and a Lewis acid (e.g., aluminum, titanium, or tin halide) for t-alkyl or aralkyl esters, to give free acids.

Preparation A-2

2-(2-Benzyloxycarbonylaminothiazol-4-yl)-3-benzyloxycarbonyl-2-propenoic acid (3).

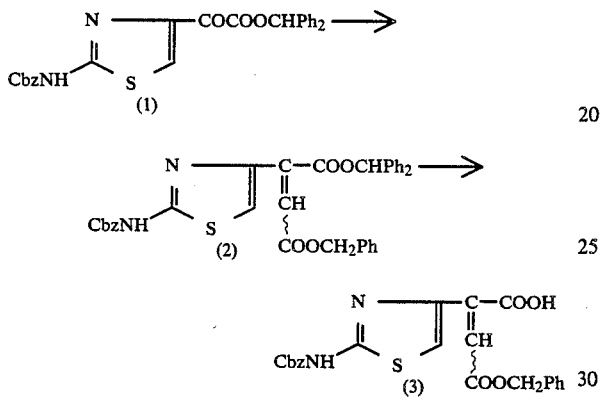

(1) A solution of 2-oxoacetate (1) and benzyloxycarbonylmethylidenetriphenylphosphorane (1.25 equivalents) in toluene or dioxane (10 parts) is refluxed for 1 to 3 hours. The mixture is concentrated and the residue purified by silica gel chromatography to give diester (2). Yield: 95%.

NMR (CDCl$_3$)$\delta$: 5.12 (s, 4H), 7.00 (s, 1H), 7.07 (s, 1H), 7.1–7.5 (m, 21H).

This product is a mixture of cis-trans isomers at the double bond.

(2) The produce (2) is dissolved in dichloromethane (7 parts) and mixed with trifluoroacetic acid (1 part) and anisole (1 part). After stirring for 7 hours at 0° C., the mixture is concentrated and triturated in a mixture of ether and hexane and then in a mixture of ether and methanol to give monoester (3), trans isomer. Yield: 83%.

IR (Mujol)$\nu$: 1730, 1710, 1695 cm$^{-1}$.

NMR (CDCl$_3$+CD$_3$OD)$\delta$: 5.17 (s, 2H), 5.27 (s, 2H), 7.07 (s, 1H), 7.2–7.5 (m, 11H) ppm.

(3) This trans isomer (3) is dissolved in tetrahydrofuran (10 parts) and mixed with phosphorus pentachloride (1.12 equivalents). After stirring for 2 hours at 0° C., the mixture is neutralized with aqueous 5% sodium hydrogen carbonate (80 ml) and stirred at room temperature. Separated crystals are collected by filtration, washed with ethyl acetate and water, suspended in water, acidified with hydrochloric acid, and extracted with ethyl acetate. The extract is washed with water, dried, and concentrated. The residue is crystallized from a mixture of ether and hexane to give monoester (3), cis isomer. Yield: 47%. mp. 144°–146° C.

IR (CHCl$_3$)$\nu$: 3410, 1720 cm$^{-1}$.

NMR (CDCl$_3$+CD$_3$OD)$\delta$: 5.18 (s, 2H), 5.23 (s, 2H), 6.62 (s, 1H), 7.15 (s, 1H), 7.32 (s, 5H), 7.35 (s, 5H) ppm.

Preparation A-3

2-(2-Benzyloxycarbonylaminothiazol-4-yl)-5-benzyloxycarbonyl-2-pentenoic acid (5)

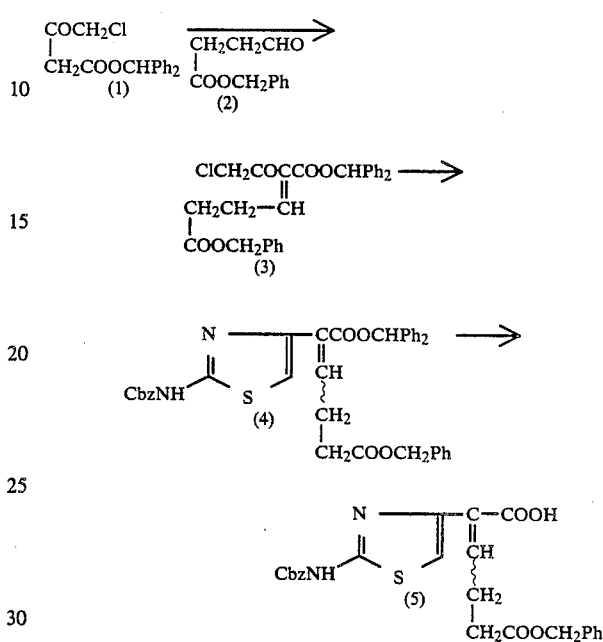

(1) A mixture of 4-chloroacetoacetic acid benzhydryl ester (1) (6.95 g), aldehyde (2) (3.9 g), benzene (35 ml), piperidine (0.79 ml), and acetic acid (0.24 mg) is heated at 50° C. for 3 hours. The mixture is washed with water, aqueous saturated sodium hydrogen carbonate, water, 0.5N-hydrochloric acid, and water, dried over magnesium sulfate, and concentrated. The residue is subjected to silica gel chromatography (eluting with benzene) to give a mixture of cis and trans (1:1) isomers of the product (3) (5.7 g).

(2) To a solution of this produce (3) in ethanol (30 ml) is added thiourea (1.1 g). After heating at 50° C. for 2 hours, the mixture is washed with aqueous saturated sodium hydrogen carbonate and concentrated. The residue is dissolved in dichloromethane (20 ml) and mixed with pyridine (0.536 ml) and benzyl chloroformate (0.757 ml) at 0° C. After 1.5 hours' stirring at 0° C., the mixture is washed with water, dried over magnesium sulfate, and concentrated. The residue is purified by silica gel chromatography (eluting with benzene-ethyl acetate (20:1) mixture) to give aminothiazole ester (4), cis isomer (467 mg) and trans isomer (600 mg).

(cis isomer)=IR (CHCl$_3$)$\nu$: 3400, 1720, 1540, 1440, 1385, 1280, 1160 cm$^{-1}$.

(trans isomer)=IR (CHCl$_3$)$\nu$: 3400, 1720, 1540, 1440, 1385, 1280, 1160 cm$^{-1}$.

(3) To the isomers of aminothiazole ester (4) respectively are added dichloromethane, anisole (1 part), and trifluoroacetic acid (2 parts). After 2 hours stirring at 0° C., the mixture gives each isomer of the corresponding dicarboxylic acid monobenzyl ester (5).

Preparation A-4

2-(2-Benzyloxycarbonylaminothiazol-4-yl)-6-benzyloxycarbonyl-2-hexenoic acid (5)

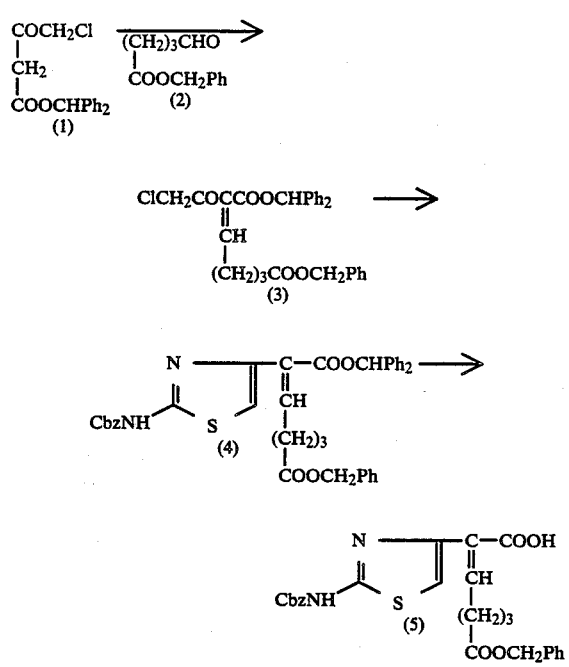

(1) A solution of ester (1) (7 g), aldehyde (2) (4.8 g), piperidine (0.15 ml), and acetic acid (0.3 ml) in benzene (40 ml) is heated at 50° C. for 3 hours. The mixture is washed with water, aqueous saturated sodium hydrogen carbonate, 0.5 N hydrochloric acid, and water, dried over magnesium sulfate, and concentrated.

(2) Resulting residue (3) (6.5 g) is dissolved in ethanol (35 ml), mixed with thiourea, and heated at 50° C. for 2 hours. The mixture is washed with aqueous saturated sodium hydrogen carbonate and concentrated. The residue is dissolved in dichloromethane (20 ml), mixed with pyridine (0.754 ml) and benzyl chloroformate (1 ml), and stirred at 0° C. for 1.5 hours. The reaction mixture is washed with water, dried, and concentrated. The residue is separated by silica gel chromatography (eluting with benzene-ethyl acetate (20:1) mixture) to give thiazole ester (4) [trans isomer (470 mg) and trans-cis (1:1) mixture (1.17 gl)].

(trans-Thiazole ester (4)): IR (CHCl₃)ν: 3400, 3000, 1720, 1540, 1440, 1370, 1280, 1150 cm⁻¹.

(cis-Thiazole ester (4)): IR (CHCl₃)ν: 3400, 3000, 1720 1540, 1440, 1370, 1280, 1150 cm⁻¹.

(3) Thiazole ester (4) (470 mg) as produced above (1) is dissolved in dichloromethane (15 ml), mixed with anisole (0.611 ml) and trifluoroacetic acid (1.22 ml), and stirred at 0° C. for 2 hours. After concentrating to dryness, the mixture is triturated in a mixture of ether and hexane (1:1) to give thiazolecarboxylic acid (5) 336 mg).

Preparation A-5

2-(5-Benzyloxycarbonylamino-1,2,4-thiadiazol-3-yl)-4-benzyloxycarbonyl-2-butenoic acid (7)

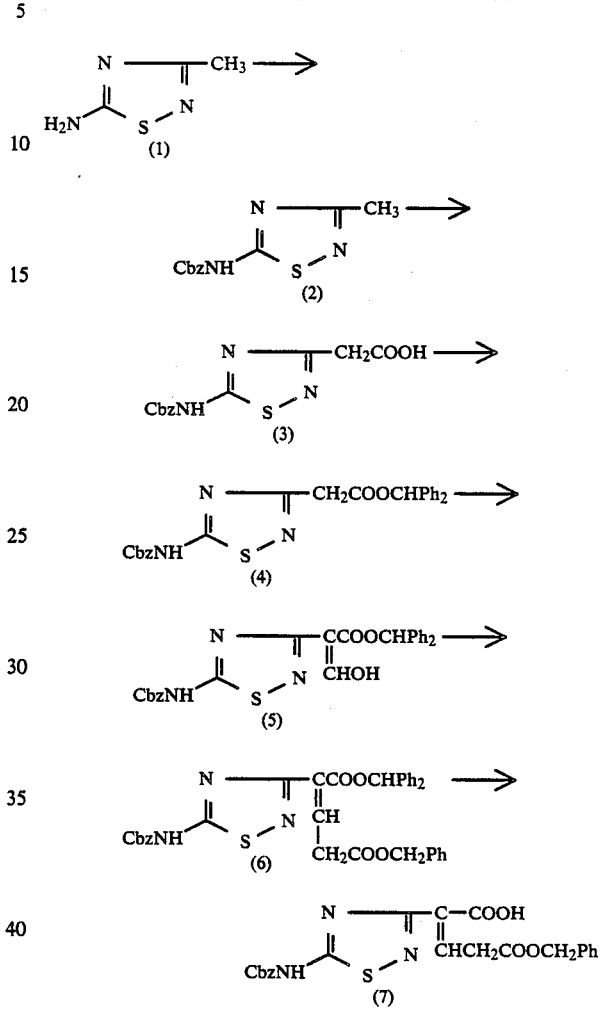

(1) Amine (1) (6 g) is amidated with benzyl chloroformate (1.2 equivalents) in dichloromethane (120 ml) containing pyridine (2.5 equivalents) at 0° C. for 2 hours to give carbamate (2) (11.2 g). mp. 157°–158° C. Yield: 94.6%.

(2) To a solution of diisobutylamine (25.2 ml) in tetrahydrofuran (125 ml) cooled at −30° C. to −5° C. is added 1.6 N n-butyllithium hexane solution (112.3 ml) over 21 minutes period. After 1 hour 20 minutes' stirring at 0° C., the mixture is mixed with a solution of carbamate (2) (11.2 g) in tetrahydrofuran (150 ml) at −68° C. to −64° C. over 1 hour 20 minutes, and stirred at the same temperature for 3 hours. This is quenched with dry ice (200 g) and warmed gradually up to −5° C. The reaction mixture is diluted with water (150 ml), washed with ethyl acetate, acidified with 2N-hydrochloric acid to pH 2, and extracted with dichloromethane. The extract solution is washed with water, dried, concentrated, and diluted with ether to afford acetic acid (3) (6.33 g). mp. 172°–173° C.

(3) To a solution of acetic acid (3) (7 g) in methanol (200 ml) is added diphenyldiazomethane until none of the acetic acid (3) is detectable. The mixture is concentrated to give Ester (4). mp. 144°–146° C.

(4) To a solution of ester (4) (4.1 g) and diphenylmethyl formate (3.03 g) in tetrahydrofuran (41 ml) cooled at 0° C. is added 60% sodium hydride (1.1 g). After 2 hours 20 minutes stirring at 60° C., the mixture is diluted with water, acidified with 2N-hydrochloric acid, and extracted with ethyl acetate. The extract is washed with water, dried, and concentrated to give aldehyde (5) (2.76 g). Yield: 63.5%.

IR (CHCl$_3$)$\nu$: 3140, 1720, 1610, 1540, 1280, 1080 cm$^{-1}$.

(5) A solution of aldehyde (5) (781 mg) and benzyloxycarbonylmethylidenephosphorane (985 mg) in dioxane (17 ml) is refluxed for 3 hours. The mixture is concentrated to give acrylate (6) (631 mg). Yield: 63.5%. A cis/trans (4:6) mixture.

IR (CHCl$_3$)$\nu$: 3150, 1730, 1545, 1280 cm$^{-1}$.

(6) To a solution of acrylate (6) (309 mg) in dichloromethane (4.5 ml) are added anisole (0.3 ml) and trifluoroacetic acid (0.6 ml). After 1 hour's stirring at room temperature, the mixture is diluted with hexane to give half ester (7) (171 mg). Yield: 75.7%. This is a cis/trans (1:6.45) mixture.

IR (CHCl$_3$)$\nu$: 1730, 1621, 1540, 1280 cm$^{-1}$.

Preparation A-6

2-(2-Benzyloxycarbonylaminothiaxol-4-yl)-3-chloro-3-benzyloxycarbonyl-2-propenoic acid (3)

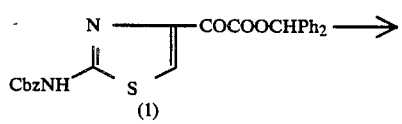

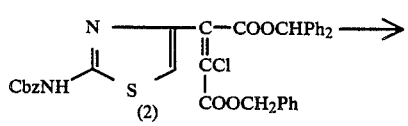

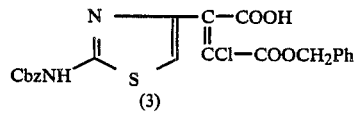

(1) A solution of ketone (1) (472 mg) and benzyloxycarbonylchloromethylenetriphenylphosphorane (467 mg) in benzene (5 ml) is heated at 60° C. for 30 minutes and concentrated. The residue is crystallized from a mixture of ether and pentane to give chloroethylene (2) (393 mg). Yield: 61%.

(2) A solution of chloroethylene (2) (270 mg) in a mixture of anisole (2 parts) and trifluoroacetic acid (1 part) is let stand for 15 minutes and concentrated to give half ester (3) (190 mg). Yield: 95%.

Preparation A-7

2-(2-Benzyloxycarbonylaminothiazol-4-yl)-3-benzyloxycarbonylmethylthio-3-chloro-2-propenoic acid (4)

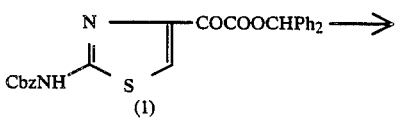

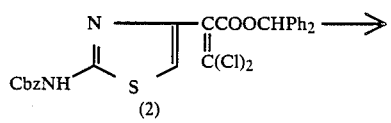

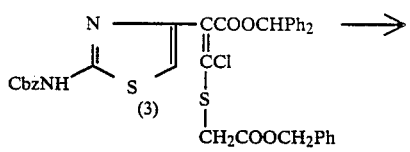

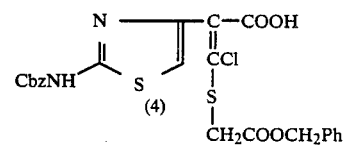

(1) Ketone (1) and dichloromethylidenetriphenylphosphorane are reacted in a manner as described in Japanese Patent Application Kokai 57-67581 to give dichloroethylene (2).

(2) To an ice cold solution of dichloroethylene (2) (395 mg) in N,N-dimethylformamide (3 ml) are added benzyl thioglycolate (200 mg) and triethylamine (153 mg) under nitrogen. After stirring for 45 minutes, the mixture is diluted in ethyl acetate, washed with water, dried, and concentrated. The residue is purified by chromatography to give thioether (3) (326 mg). Yield: 64%.

(3) A solution of thioether (3) in a mixture of trifluoroacetic acid (2 parts) and anisole (2 parts) is let stand for 30 minutes and concentrated to give half ester (4). Yield: 88%.

Preparation A-8

2-(2-Benzyloxycarbonylaminothiazol-4-yl)-3-chloro-6-benzyloxycarbonyl-2-hexenoic acid (4)

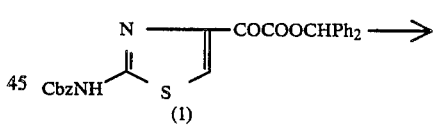

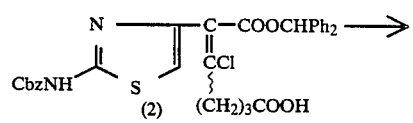

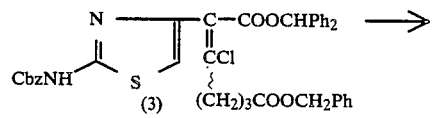

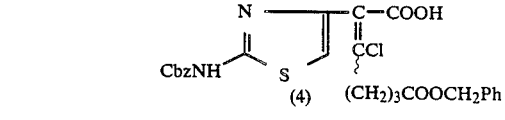

(1) To a suspension of (4-carboxybutyl)triphenylphosphonium bromide (887 mg) in tetrahydrofuran (3.5 ml) is added 1M-lithium bistrimethylsilylamide (4.2 ml). After 15 minutes' stirring at room temperature, this solution is dropwise added to a suspension of iodobenzenedichloride (605 mg) in tetrahydrofuran at −78° C. After 10 minutes at −78° C., lithium bistrimethylsilylamide (2.2 ml) is added to the mixture. To this solution is added a solution of ketoester (1) (378 mg) in tetrahydrofuran (2 ml). The mixture is stirred at −78° C. for 10 minutes and at room temperature for 1 hour, diluted with diluted hydrochloric acid, and extracted with ethyl acetate. The extract solution is dried and concentrated. The residue is purified by silica gel chromatography (eluting with dichloromethane and ethyl acetate (1:1) mixture) to give vinylcarboxylic acid (2) (250 mg).

IR (CHCl$_3$) $\nu$: 1715, 1540 cm$^{-1}$.

(2) Esterification of vinylcarboxylic acid (2) (353 mg) with oxalyl chloride and benzyl alcohol in the presence of pyridine in a conventional manner gives vinyl ester (3) (305 mg).

NMR (CDCl$_3$) δ:1.85–3.00 (m, 6H), 5.07 (s, 2H), 5.25 (s, 2H), 6.48 (s, 1H), 7.05 (s, 1H), 7.10–7.55 (m, 20H) ppm.

(3) Stirring a mixture of vinyl ester (3) (275 mg), trifluoroacetic acid (0.5 ml), and anisole (1 ml) for 15 minutes at room temperature gives half ester (4) (95 mg).

NMR (CDCl$_3$+CD$_3$OD) δ: 1.80–3.00 (m, 6H), 5.09 (s, 2H), 5.26 (s, 2H), 6.85 (s, 1H), 7.05–8.00 (m, 10H) ppm.

Preparation A-9

2-[2-(N-Methoxyethoxymethyl-N-benzyloxycarbonylamino)triazol-4-yl]-3-chloro-5-benzyloxycarbonyl-2-pentenoic acid (6)

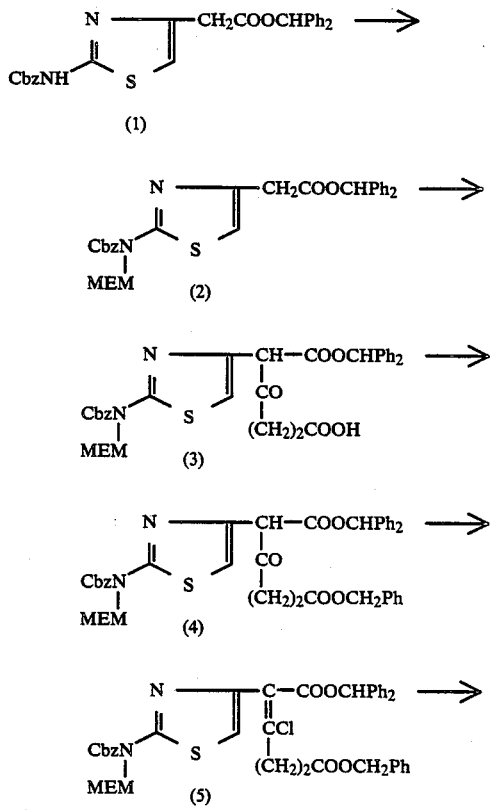

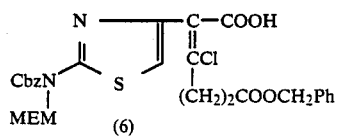

(1) To a solution of aminoester (1) (115 mg) in N,N-dimethylformamide (1 ml) are added potassium carbonate (45 mg) and methoxyethoxymethyl chloride (0.043 ml). After stirring at room temperature for 1.5 hours, the mixture is diluted with iced hydrochloric acid and extracted with ethyl acetate. The extract is washed with water, dried, and concentrated. The residue is purified by silica gel chromatography to give methoxyethoxymethylamino ester (2).

Yield: 74%.

NMR (CDCl$_3$) δ: 3.25 (s, 3H), 3.77 (s, 2H), 5.28 (s, 2H), 5.55 (s, 2H), 6.68 (s, 1H) ppm.

(2) To a solution of 0.3M-lithium bistrimethylsilylamide in tetrahydrofuran (1.4 ml) is added a solution of methoxyethoxymethylamino ester (2) (100 mg) in tetrahydro-furan (1 ml) at −78° C. under nitrogen. After stirring for 15 minutes, a solution of succinic anhydride (22 mg) in tetrahydrofuran (0.5 ml) is added to the solution. After 50 minutes' stirring at −78° C., the reaction mixture is acidified with 4N-hydrochloric acid (0.5 ml) and extracted with dichloromethane. The extract is washed with water, dried, and concentrated. The residue is purified by silica gel chromatography to give ketoester (3) (64%) and amino ester (1) (24 %).

NMR (CDCl$_3$) δ: 3.27 (s, 3H), 5.32 (s, 2H), 5.50, 5.65 (2×s, 2H), 9.4 (brs, 1H) ppm.

(3) To a solution of keto ester (3) (541 mg) in benzene (5 ml) is added a 0.485M-solution (1.81 ml) of sodium methoxide in methanol. After stirring for 5 minutes, the mixture is concentrated. The residue is dissolved in N,N-dimethylformamide (5 ml), mixed with benzyl bromide (0.149 ml), stirred for 5.5 hours at room temperature, let stand overnight, and subjected to usual work-up and silica gel chromatography to afford ketodiester (4). Yield: 33%.

NMR (CDCl$_3$) δ: 3.26 (s, 3H), 5.05 (s, 2H), 5.32 (s, 2H), 5.55, 5.63 (2×s, 2H) ppm.

(4) to a solution of triphenylphosphine (284 mg) in tetrahydrofuran (4 ml) cooled at −15° C. are added a 0.85 M solution of chlorine in carbon tetrachloride (1.27 ml), triethylamine (0.152 ml), and a solution of ketodiester (4) (160 mg) in tetrahydrofuran (2 ml). The mixture is warmed to room temperature, stirred for 6.5 hours, subjected to usual work-up, and silica gel chromatography to give chlorodiester (5). Yield: 67%.

This product is a mixture of cis and trans (1:1) geometric isomers.

IR (CHCl$_3$) $\nu$: 1740 cm$^{-1}$.

(5) To an ice cold solution of chlorodiester (5) (109 mg) in anisole (1 ml) is added trifluoroacetic acid (0.3 ml). After stirring at room temperature for 1 hour, the mixture is concentrated, and the residue is purified by silica gel chromatography to give chloromonoester (6) trifluoroacetate salt 112 mg). This product is a mixture of cis and trans (1:1) geometric isomers.

IR (CHCl$_3$) $\nu$: 3350, 1720, 1680 cm$^{-1}$.

Preparation A-10

2-(5-Benzyloxycarbonylamino-1,2,4-thiadiazol-3-yl)-3-benzyloxycarbonyl-2-propenoic acid (4)

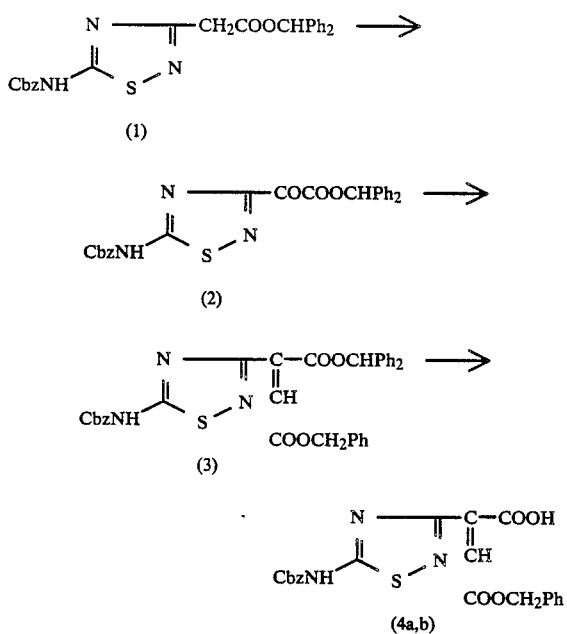

(1) To a solution of ester (1) (1.012 g) in dioxane (10 ml) is added selenium dioxide (0.66 g). After stirring for 2 hours at 100° C., the mixture is filtered. The filtrate is concentrated. The residue is dissolved in ether and purified by silica gel chromatography (eluting with a hexane-acetone (3:2) mixture) to give ketoester (2) (1.025 g). Yield: 98.3%.

IR (Nujol) ν: 3380, 1720, 1240, 1085 cm⁻¹.

(2) A solution of ketoester (2) (1.025 g) and triphenylphosphoranilideneacetic acid benzyl ester (1.06 g) in dioxane (20 ml) is stirred at 100° C. for 2 hours and concentrated. The residue is purified by silica gel chromatography (eluting with acetone-hexane (3:1 to 3:2) mixture) to give diester (3) (1.24 g). Yield: 93%. mp. 173°–174° C.

(3) To a solution of diester (3) (348 mg) in dichloromethane (4.7 ml) are added anisole (0.35 ml) and trifluoroacetic acid (0.76 ml). After stirring for 1 hour at room temperature, the mixture is concentrated and washed with ether to give cis-monoester (4a) (147 mg). Yield: 58.3%. mp. 201°–202° C. The washing is concentrated, washed with hexane, and crystallized from a mixture of ether and hexane to give trans-monoester (4b) (98 mg). Yield: 38.9%. mp. 155°–156° C.

Preparation A-11

2-(2-t-Butoxycarbonylaminothiazol-4-yl)-4-methyl-4-benzyloxycarbonyl-2-pentenoic acid (3)

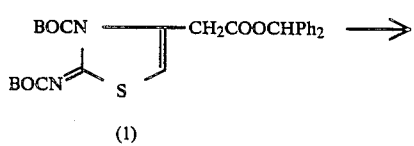

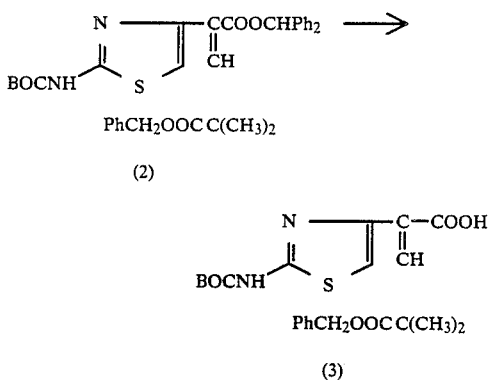

To a solution of acetate (1) (628 mg) in tetrahydrofuran (16 ml) cooling at −50° C. is added potassium t-butoxide (282 mg). After stirring for 5 minutes, the mixture is mixed with benzyl 2-formyl-2,2-dimethylacetate (0.32 ml), stirred for 20 minutes, warmed to room temperature in 5 minutes, neutralized with 10% hydrochloric acid, and extracted with ethyl acetate. The extract is washed with saline, dried, and concentrated. The residue is dissolved in benzene (10 ml), mixed with DBU (0.36 ml), stirred at room temperature for 4 hours, neutralized with 10% hydrochloric acid, washed with water, dried, concentrated, dissolved in benzene (10 ml), mixed with aqueous sodium sulfite (250 mg) solution (10 ml), and stirred for 24 hours. Benzene layer is washed with water, dried, concentrated, and purified by silica gel chromatography to give diester (2), cis isomer (431 mg: 59% yield) and trans isomer (158 mg; yield: 22%).

IR (CHCl₃) ν: 3410, 1725 cm⁻¹(cis isomer).
IR (CHCl₃) ν: 3400, 1720 cm⁻¹(trans isomer).

(2) To a solution of diester (2), cis isomer (431 mg), in dichloromethane (8 ml) is added a mixture of anisole (1.2 ml) and trifluoroacetic acid (1.2 ml). After stirring at 0° C. for 3 hours, the mixture is concentrated and purified by silica gel chromatography to give cis-isomer of monoester (3) (242 mg). Yield: 77%. mp 158°–160° C. (decomp. recrystallized from benzene).

(3) To a solution of diester (2), trans isomer (237 mg), in dichloromethane (4 ml) is added a mixture of anisole (0.6 ml) and trifluoroacetic acid (0.6 ml). After stirring at 0° C. for 3.5 hours, the mixture is concentrated and purified by silica gel chromatography to give trans-isomer of monoester (3) (98 mg). Yield: 57%. mp. 175°–177° C. (decomp., recrystallized from benzene).

Preparation A-12

2-(2-t-Butoxycarbonylaminothiazol-4-yl)-3-t-butoxycarbonylmethoxy-2-propenoic acid (7)

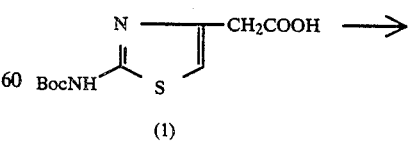

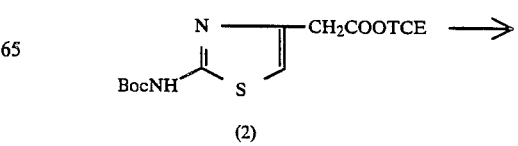

-continued

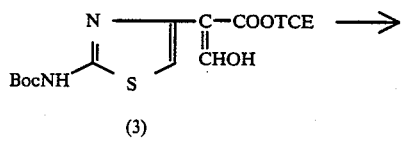

(3)

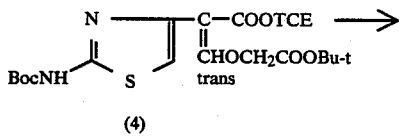

(4)

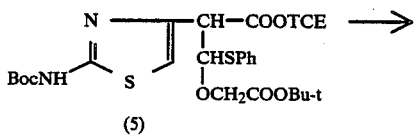

(5)

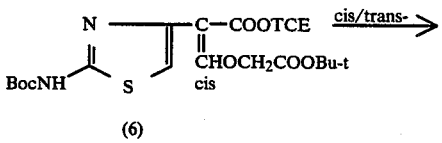

(6)

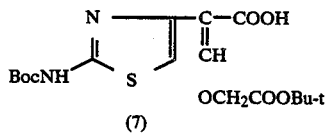

(7)

(1) To a suspension of acetic acid (1) (11 g) in dichloromethane (120 ml) is added triethylamine (90 ml). The mixture is cooled at −78° C., mixed with 2,2,2-trichloroethyl chloroformate (4.87 ml) and N,N-dimethylaminopyridine (432 mg), stirred at 0° C. for 10 minutes and at room temperature for 2 hours, diluted with ethyl acetate, washed with water, dried, and concentrated. The residue is purified by 10% aqueous silica gel chromatography (eluting with a benzene-ethyl acetate (9:1) mixture) to give trichloroethyl ester (2) (9.10 g). Yield: 66%.

IR (CHCl$_3$) ν: 3400. 1760, 1720, 1150 cm$^{-1}$.

(2) To a suspension of sodium hydride (2.88 g) in tetrahydrofuran (80 ml) is dropwise added a solution of trichloroethyl ester (2) (9.10 ) and 2,2,2-trichloroethyl formate (6.21 g) in tetrahydrofuran (34 ml). After stirring at room temperature for 2 hours, the mixture is diluted with ethyl acetate, acidified with acetic acid (5.3 ml), washed with watr, dried, and concentrated. The residue is crystallized from petroleum ether to give formylester (3) (4.49g). Yield: 46%.

IR (CHCl$_3$) ν: 3420. 1735, 1620 cm$^{-1}$.

(3) To an ice cold solution of formylester (3) (4.49 g) in N,N-dimethylformamide (40 ml) is added 60% sodium hydride (426 mg). The mixture is stirred until gas evolution ceases, mixed with t-butylbromoacetate (3.15 g), kept at room temperature overnight, diluted with ethyl acetate, washed with saline, dried, concentrated, and purified by silica gel chromatography (eluting with a benzene-ethyl acetate (19:1 to 2:1 ) mixture) to give diester (4) (3.03 g). Yield: 53%.

IR (CHCl$_3$) ν: 3400, 1723, 1630, 1150, 1120 cm$^{-1}$.

(4) To a solution of diester (4) (3.03 g) in tetrahydrofuran (30 ml) are added benzenethiol (0.70 ml) and triethylamine (0.79 ml). The mixture is stirred at room temperature for 3.5 hours, concentrated, and purified by silica gel chromatography (eluting with benzene-ethyl acetate (9:1 to 8:2) mixture) to give phenylthiopropionate (5) (3.36 g). Yield: 92%.

The product is 7:3 mixture of the two geometric isomers.

IR (CHCl$_3$) ν: 3400, 1750, 1725, 1155, 1120 cm$^{-1}$.

(5) To a solution of phenylthiopropionate (5) (3.15 g) in dichloromethane (35 ml) cooled at −40° C. is added m-chloroperbenzoic acid (80%, 1.07 g). The mixture is stirred at −40° C. for 10 minutes and at room temperature for 10 minutes, diluted with ethyl acetate, stirred with aqueous 2% sodium hydrogen sulfite, and stirred at room temperature for 5 minutes.

The organic layer is taken, washed with aqueous 5% sodium hydrogen carbonate and saturated saline, dried, concentrated, dissolved in benzene (150 ml), and refluxed for 5 minutes. The mixture is washed with aqueous 5% sodium hydrogen carbonate and saturated saline, dried, concentrated, and purified by silica gel chromatography (eluting with a benzene-ethyl acetate (9:1 to 1:1) mixture) to give diester (6) (1.13 g). Yield: 45%.

IR (CHCl$_3$) ν: 3420, 1730, 1620, 1540, 1153, 1140 cm$^{-1}$.

(6) To a solution of diester (6) (0.80 g) in acetic acid (8 ml) is added zinc powder (2.0 g). After stirring at room temperature for 1 hour, the mixture is diluted with dichloromethane, mixed with 2N-hydrochloric acid, stirred for 10 minutes at room temperature, filtered to remove solid, and the organic layer is taken. This is washed with water, dried, and concentrated to give Z-isomer of monoester (7) (605 mg). Yield: 100%.

IR (CHCl$_3$) ν: 3400, 3550–2500, 1725, 1620, 1150 cm$^{31\ 1}$.

E-isomer of monoester (7) (750 mg) is recovered from the mother liquor. Yield: 30%.

IR (KBr) ν: 3420, 1742, 1710, 1610, 1130 cm$^{-1}$.

Preparation A-13

2-(2-Benzyloxycarbonylaminothiazol-4-yl)-4-benzyloxycarbonylpentenoic acid (3)

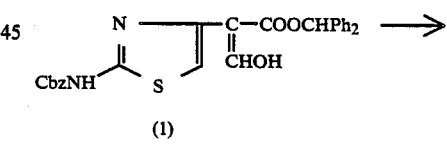

(1)

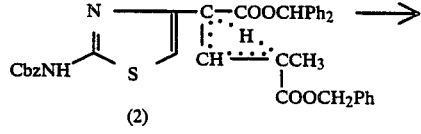

(2)

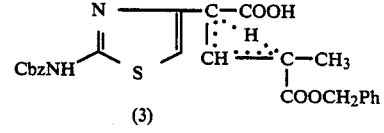

(3)

(1) A solution of hydroxymethylene (1) (1.46 g) in benzyloxycarbonylethylidenetriphenylphosphorane (2.5 g) in toluene (20 ml) is stirred at 80° C. for 19 hours and at 110° C. for 4 hours, and then concentrated. The residue is purified by silica gel chromatography to give diester (2) (0.808 g). Yield: 43%.

NMR (CDCl$_3$) δ: 1.15 (d, J=7 Hz, 1.5H), 1.71 (s, 1.5H), 4.90 (d, J=9 Hz, 0.5H), ppm.

(2) To a solution of diester (2) in dichloromethane (20 ml) are added anisole (3 ml) and trifluoroacetic acid (3 ml). After stirring at room temperature for 3 hours, the mixture is concentrated and triturated in a mixture of hexane and ether to give monoester (3) (508 mg). Yield: 85%.

IR (CHCl$_3$) ν: 3400, 1725 cm$^{-1}$.

Preparation A-14

2-(Thiazol-4-yl)-4-benzyloxycarbonyl-2-butenoic acid (3)

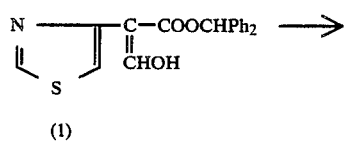

(1)

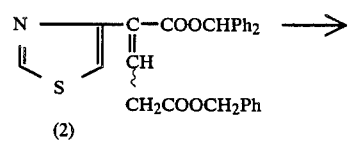

(2)

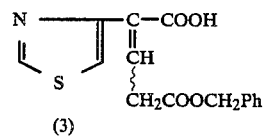

(3)

(1) To a solution of formylester (1) (11.5 g) in benzene (220 ml) is added benzyloxycarbonylmethylidenephosphorane (19.5 g). After refluxing for 7 to 10 hours, the mixture is concentrated to a half to a third volume and purified by silica gel chromatography (eluting with a benzene-ethyl acetate (30:1) mixture) to give diester (2) (15.5 g). Yield 97%. The product is a mixture of cis and trans geometric isomers.

IR (CHCl): 1720 cm. (2) To a solution of diester (2) (15.0 g) in dichloromethane (150 ml) is added trifluoroacetic acid (32 ml) at 0° C. After stirring at room temperature for 1.5 hours, the mixture is concentrated. The residue is stirred in hexane, diluted with ethyl acetate, and extracted with saturated aqueous sodium hydrogen carbonate. The extract is acidified with 10% hydrochloric acid to pH 3 to 4 and extracted with ethyl acetate. The extract is dried, concentrated, and triturated in a mixture of ether and hexane (1:1) to give monoester (3). Yield: 55%. This product is a mixture of cis and trans (1:1) geometric isomers.

NMR (CDCl$_3$-CD$_3$OD) δ: 3.53, 3.76 (d, J=8 Hz, 2H), 5.13, 5.15 (2×s, 2H), 7.23, 7.38 (2×t, J=8 Hz, 1H), 7.35 (s, 5H), 7.57, 7.61 (d, J=2 Hz, 1H), 8.79, 8.82 (d, J=2 Hz, 1H) ppm.

Preparation A-15

2-(3-t-Butoxycarbonylamino-5-isoxazolyl)-4-benzyloxycarbonyl-2-butenoic acid (7)

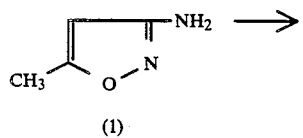

(1)

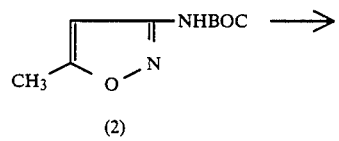

(2)

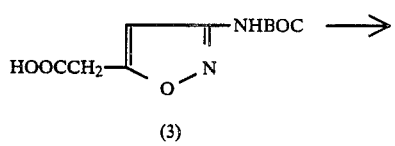

(3)

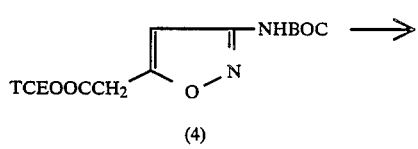

(4)

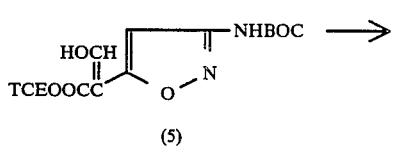

(5)

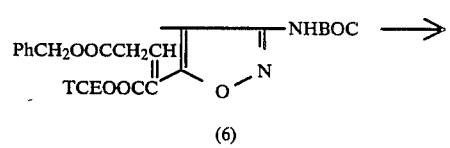

(6)

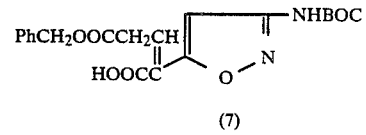

(7)

(1) A solution of 3-amino-5-methylisoxazole (1) (56 g) in di-t-butylpyrocarbonate is stirred at 105°–110° C. for 17 hours. The mixture is concentrated and diluted with ether and water. The organic layer is taken, washed with water, diluted hydrochloric acid, water, and saline, dried, and concentrated. The residue is washed with petroleum ether to give t-butoxycarbonylamine (2) (75 g). mp 108°–109° C.

(2) To a solution of diisopropylamine (23.4 ml) under nitrogen in tetrahydrofuran (90 ml) cooled at −20° C. is added n-butyllithium (1.6N-hexane solution 125 ml). After stirring for 15 minutes, the mixture is cooled to −78° C., mixed with a solution of t-butoxycarbonylamine (2) (8.3 g) in tetrahydrofuran (40 ml) over 2 minutes period, stirred for 1 hour, quenched with dry-ice (20 g), and concentrated. The residue is dissolved in water, washed with ether, acidified with hydrochloric acid under ice cooling, and extracted with ethyl acetate. The extract is washed with water, dried, and concentrated. The residue is washed with ether to give acetic acid (3) (4.35 g). mp 173°–174° C. (decomp.).

(3) To a solution of acetic acid (3) in dichloromethane (200 ml) is added triethylamine (8.63 ml) at 0° C. This is cooled to −78° C., mixed with trichloroethyl chloroformate (13.1 g) and 4-dimethylaminopyridine (0.76 g), and stirred for 15 minutes. The mixture is warmed to room temperature, kept overnight, concentrated, diluted with water, and extracted with ethyl acetate. The extract is washed with diluted hydrochloric acid, aqueous sodium hydrogen carbonate, water, and saline, concentrated, and purified by silica gel chromatography (eluting with benzene-ethyl acetate (3:1) mixture) to give trichloroethylester (4) (19 g). mp 146°–147° C.

(4) To a suspension of 60% sodium hydride 6.72 g) in tetrahydrofuran (220 ml) at −30° to −10° C. is added a solution of Trichloroethylester (4) and trichloroethyl formate (14.4 ml) in tetrahydrofuran (100 ml) over a 40 minutes period. After 1.5 hour's stirring, the mixture is poured into iced hydrochloric acid and extracted with ethyl acetate. The extract is washed with water and saline, dried, concentrated, and washed with petroleum ether to give hydroxymethylidene compound (5) (17.45 g). mp >210° C.

(5) A solution of hydroxymethylidene compound (5) (8.06 g) and benzyloxycarbonylmethylidenetriphenylphosphorane (11.1 g) in dioxan (350 ml) is stirred at 55° C. for 9 hours. The mixture is concentrated, dissolved in water and ethyl acetate, washed with diluted hydrochloric acid, aqueous sodium hydrogen carbonate, water, and saline, dried, concentrated, and purified by silica gel chromatography (eluting with a mixture of benzene and ethyl acetate (1:0 to 15:1) to give diester (6) (6.35 g).

IR (CHCl$_3$) $\nu$: 3410, 2950, 1735, 1607, 1585 cm$^{-1}$.

(6) To a solution of diester (6) (1.85 g) in dichloromethane (20 ml) is added zinc (5 g) and acetic acid (20 ml) at 0° C. After 40 minutes stirring, the mixture is poured into dichloromethane and diluted hydrochloric acid, filtered to remove solid, and extracted with dichloromethane. The extract is washed with water and saline, dried, concentrated, and purified by silica gel chromatography (eluting with a benzene-ethyl acetate (3:1) mixture) go give monocarboxylic acid (7) (0.25 g).

IR (KBr) $\nu$: 3400, 3250, 2960, 1736, 1618 cm$^{-1}$.

Preparation A-16

2-Phenyl-4-benzyloxycarbonyl-2-butenoic acid (3)

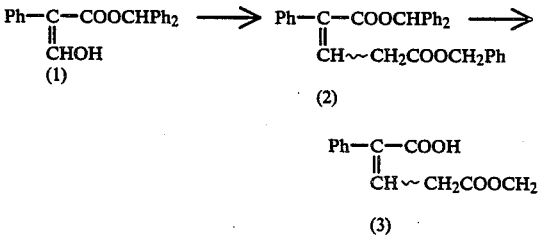

(1) To a solution of 2-formylphenylacetic acid diphenylmethyl ester (1) (1.94 g) in dioxane (20 ml) is added benzyloxycarbonylmethylidenetriphenylphosphorane (3.16 g) at room temperature. After stirring at 60° to 65° C. for 50 minutes, the mixture is concentrated and purified by silica gel chromatography (eluting with dichloromethane) to give diester (2) (1.81 g). Yield: 61%.

NMR (CDCl$_3$) δ: 3.18, 3.58 (2×d, J=8 Hz, 2H), 5.12, 5.24 (2×s, 2H), 6.93 (s, 1H) ppm.

(2) To a solution of diester (2) (1.79 g) in dichloromethane (40 ml) are added anisole (4 ml) and trifluoroacetic acid (4 ml) at 0° C. After 2.5 hours' stirring, the mixture is concentrated and triturated in hexane to give monoester (3) (0.84 g). Yield: 73%. This is a mixture of cis and trans (17.83) geometric isomers.

IR (CHCl$_3$) $\nu$: 1730, 1690 cm$^{-1}$.

Preparation A-17

2-(2-Thienyl)-4-benzyloxycarbonyl-2-butenoic acid (2)

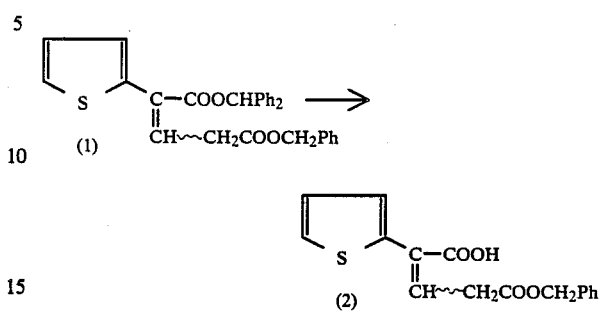

Diester (1) (3.3 g) prepared in a manner similar to Preparation A-16 is dissolved in dichloromethane (60 ml), mixed with anisole (7 ml) and trifluoroacetic acid (7 ml) at 0° C., stirred for 2.5 hours, concentrated, and triturated in hexane. Resulting solid is purified by hexane-ether giving monoester (2) (1.19 g). Yield: 56%.

Diester (1): IR (CHCl$_3$) $\nu$: 1730sh, 1722, 1165 cm$^{-1}$.
Monoester (2): IR (CHCl$_3$) $\nu$: 1730, 1695 cm$^{-1}$.

PREPARATION B

(INTRODUCTION OF 3-SUBSTITUENTS)

Preparation B-1

7beta-Amino-3-(2,2,2-trifluoroethylthio)-3-cephem-4-carboxylic acid p-nitrobenzyl ester (3)

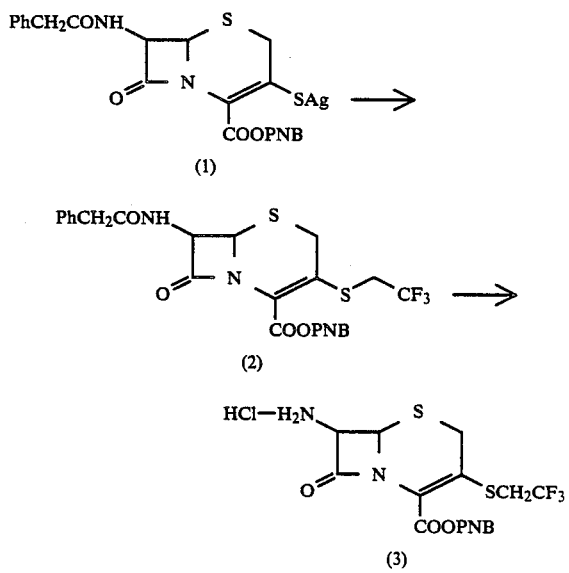

(1) To a suspension of silver mercaptide (1) (1.86 g) in hexamethylphosphorotriamide (45 ml) is added sodium iodide 0.96 g). After stirring at room temperature for 50 minutes under nitrogen, the mixture is mixed with trifluoromethanesulfonic acid trifluoroethyl ester (2.95 g). After stirring at room temperature for 1 hour, the reaction mixture is poured into ice water and extracted with ethyl acetate. The extract is washed with water, dried, and concentrated. The residue is purified by silica gel chromatography (eluting with benzeneethyl acetate (2:1) mixture) to give sulfide (2) (1.03 g). mp. 159°–160° C.

(2) To an ice cold solution of sulfide (2) (690 mg) in dichloromethane (22 ml) are added phosphorus pentachloride (675 mg) and pyridine (0.288 ml). After stirring at room temperature for 2 hours, the mixture is cooled to −40° C., diluted with methanol (22 ml), stirred at 0° C. for 2 hours, mixed with water (0.5 ml), and concentrated. The residue is triturated in ether to separate solid, which is suspended in dichloromethane, washed with aqueous sodium hydrogen carbonate and water, and concentrated to give amine (3) (562 mg).

IR (CHCl$_3$) ν: 3300br, 1775, 1735 cm$^{-1}$.

Preparation B-2

7beta-Amino-3-(2-fluoroethylthio)-3-cephem-4-carboxylic acid p-nitrobenzyl ester (4)

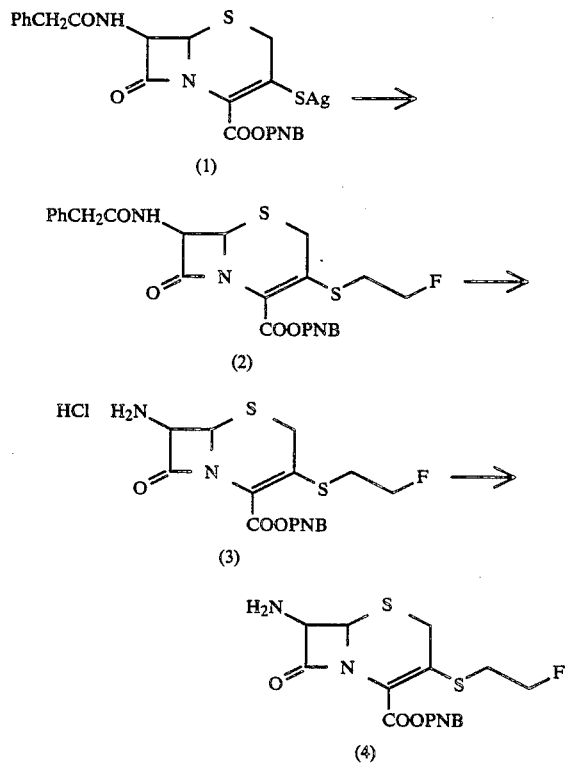

(1) To a suspension of silver mercaptide (1) (2 g) in hexamethylphosphorotriamide (60 ml) are added p-toluenesulfonic acid 2-fluoroethyl ester (2.95 g) and sodium iodide (2.02 g). After keeping at room temperature for 4.5 hours, the mixture is poured into ice water (100 ml) and extracted with ethyl acetate. The extract is washed with water, dried, concentrated, dissolved in dichloromethane, and diluted with ether to separate thioether (2). mp. 144°–149° C.

Yield: 87.8%.

IR (CHCl$_3$) ν: 3400, 1780, 1720, 1680, 1630 cm$^{-1}$.

(2) To a solution of thioether (2) (1.54 g) in dichloromethane (38.5 ml) are added pyridine (0.52 ml) and phosphorus pentachloride (1.207 g). After keeping at room temperature for 2.5 hours, the reaction mixture is cooled at −40° C., diluted with isobutanol (38.5 ml), kept at 0° C. for 3 hours, and filtered to collect separated crystals of amine hydrochloride (3 ). Yield: 91%

IR (Nujol) ν: 3140, 2645, 2585, 1773, 1604, 1600, 1512, 1492, 1460 cm$^{-1}$.

(3) A mixture os amine hydrochloride (3) (1.186 g), ethyl acetate (50 ml), sodium hydrogen carbonate (1.107 g), and water (30 ml) is stirred at 0° C. The organic layer is washed with aqueous sodium hydrogen carbonate and water, dried, and concentrated to give amine (4). Yield: 94.2%.

IR (CHCl$_3$) ν: 3400, 1772, 1726, 1602, 1513 cm$^{-1}$.

Preparation B-3

7beta-Amino-3-vinylthio-3-cephem-4-carboxylic acid p-nitrobenzyl ester (4)

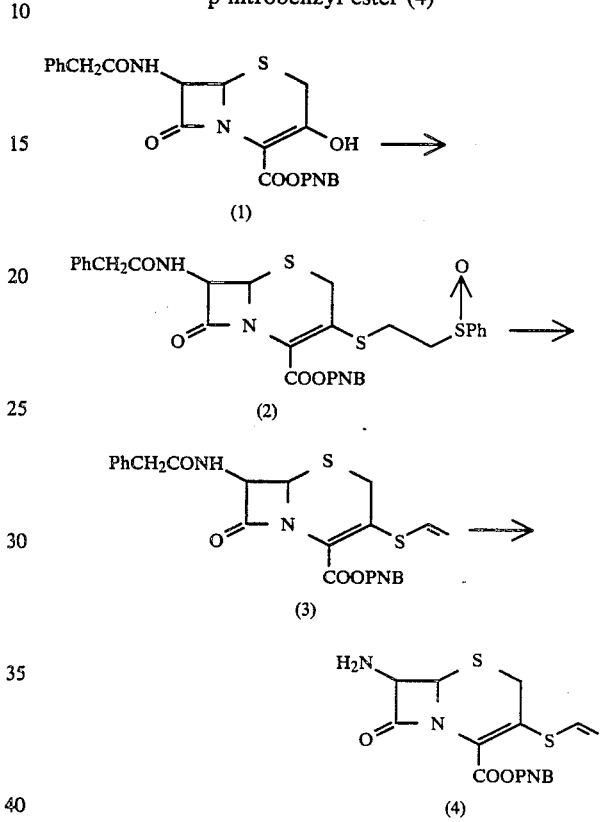

(1) To a solution of 3-enol (1) (9.38 g) in acetonitrile (120 ml) are added diphenyl chlorophosphinate (6.57 g) and diisopropylaminoethane (2.97 g). After stirring for 2 hours, this is mixed with 2-(benzenesulfinyl)ethanethiol (3.16 g), diisopropylaminoethane (2.19 g), and acetonitrile (6 ml), and stirred at −40° C. to −25° C. for 2.5 hours. The mixture is poured into iced hydrochloric acid and extracted with dichloromethane. The extract is washed with water, dried, and concentrated. The residue is crystallized from ethyl acetate-ether to give sulfoxide (2) (6.84 g). mp. 174°–176° C.

(2) A solution of sulfoxide (2) (2 g) in 1,1,2-trichloroethane (40 ml) is refluxed for 11 hours under nitrogen. The reaction mixture is concentrated, and crystallized from ether to give vinyl thioether (3) (1.38 g). mp. 193°–194° C.

(3) To a stirred and ice cold solution of vinyl thioether (3) (440 mg) in dichloromethane (15 ml) are added phosphorus pentachloride (358 mg) and pyridine (149 mg) under nitrogen. After stirring at room temperature for 2 hours, the reaction mixture is cooled to −40° C., diluted with methanol (15 ml), and stirred for 2 hours at 0° C. The mixture is mixed with water (1 ml), concentrated, washed with ether, suspended in dichloromethane, and washed with aqueous 10% sodium hydrogen carbonate and water, dried, and concentrated. The resi-

Preparation B-4

7beta-[2-(2-Aminothiazol-4-yl)-4-carboxy-2-butenamide]-3-cyanomethylthiomethyl-3-cephem-4-carboxylic acid (5)

Preparation B-5

7beta-Amino-3-(3,3,3-trifluoro-1-propenyl)-3-cephem-4-carboxylic acid diphenylmethyl ester (3)

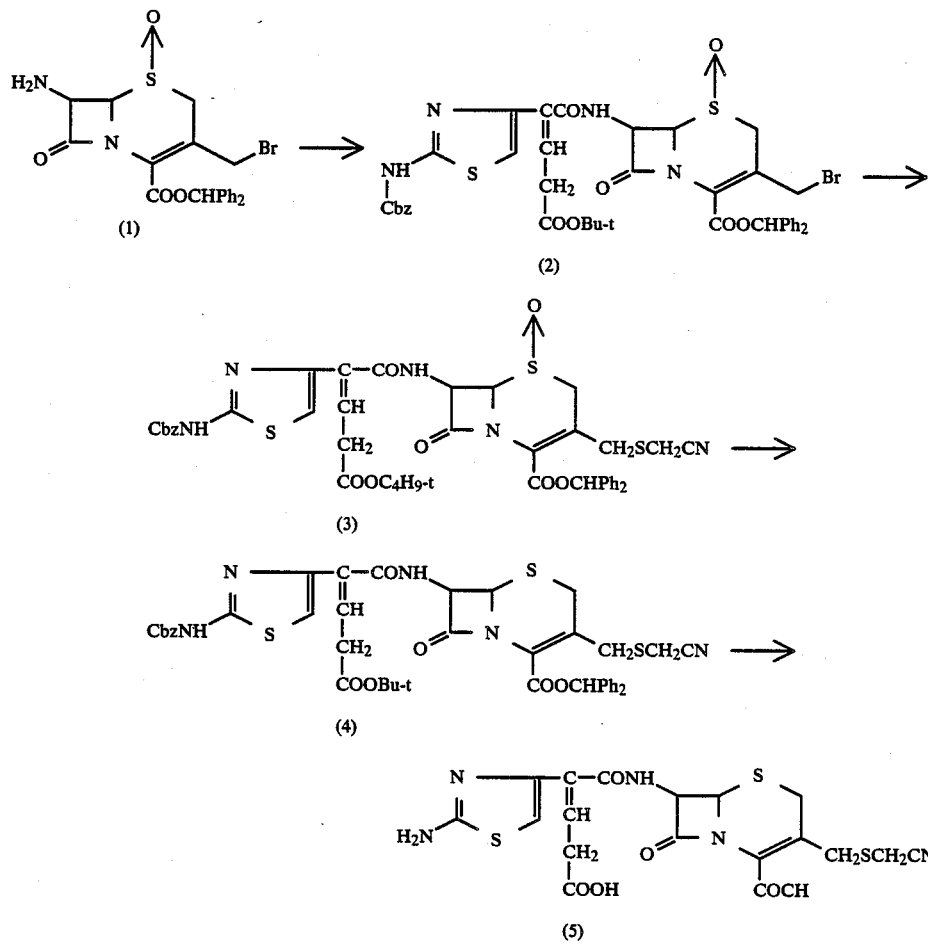

(1) To a solution of bromomethyl compound (2) (340 mg) (prepared by amidating Amine (1) in a manner similar to Example 2) in N,N-dimethylformamide (3 ml) is added at −70° C. an ethanol solution of sodium cyanomethylmercaptide (prepared from cyanomethyl thiolacetate (71 mg) and sodium ethylate in ethanol). Afer 2 hours' stirring at −65° C. to −70° C., the mixture is poured into ethyl acetate, washed with water, dried and concentrated. The residue is purified by silica gel chromatography (eluting with a mixture of benzene and ethyl acetate (3:1) to give oxide (3). Yield: 57.2%.

(2) To a solution of oxide (3) (690 mg) in acetone (10 ml) are added potassium iodide (883 mg) and acetyl chloride (0.339 ml) at −35° C. After 90 minutes' stirring at −20° C. to −25° C., the mixture is diluted with ethyl acetate, washed with diluted sodium thiosulfate, and aqueous sodium hydrogen carbonate, dried, and concentrated to give sulfide (4). Yield: 85.6%.

(3) To a solution of sulfide (4) (550 mg) in anisole (10 ml) is added a solution of aluminium chloride (1.24 g) in anisole (5 ml) at −30° C. After 3 hours' stirring, the mixture is diluted with hydrochloric acid and washed with ethyl acetate. The aqueous layer is purified with synthetic adsorbent HP 20 (Mitsubishi Chemical K.K.) and eluted to give aminocarboxylic acid (5).
Yield: 74.4%.

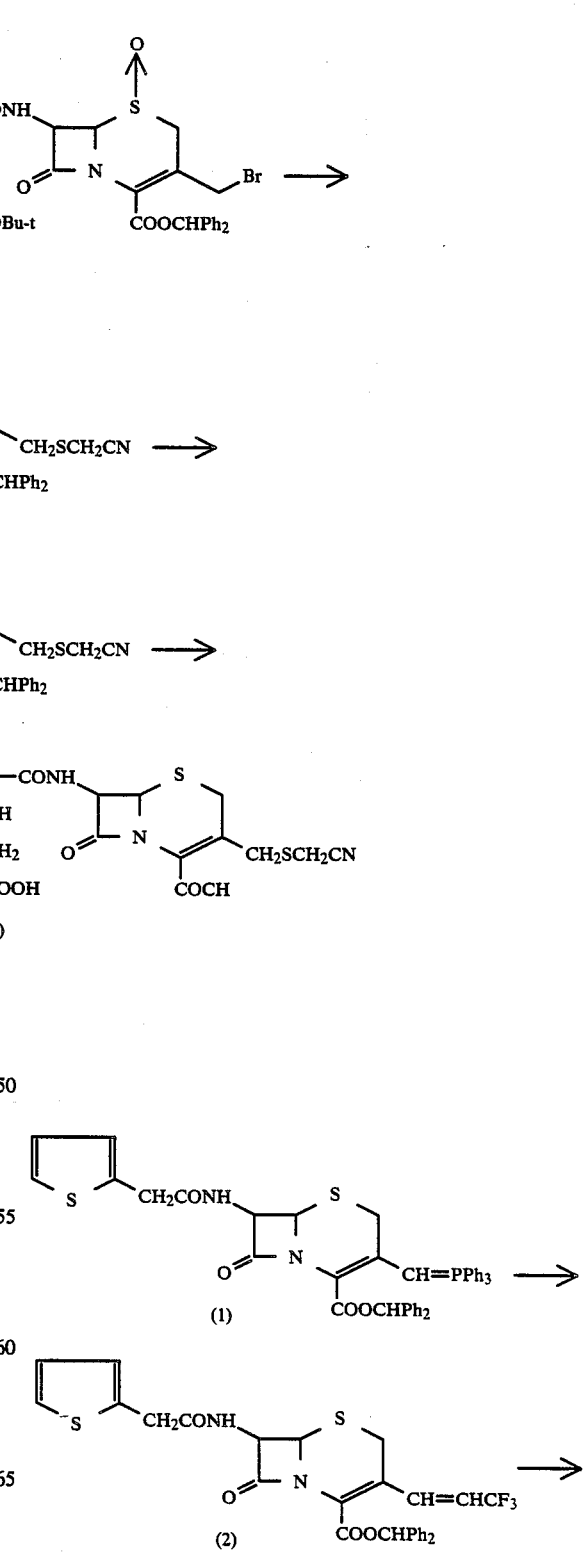

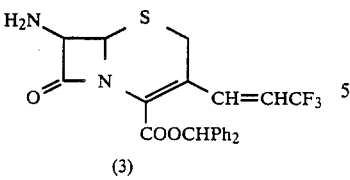

(3)

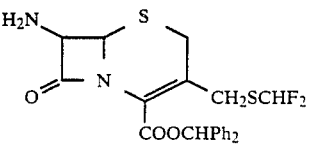

(7)

(1) Trifluoroacetaldehyde ethyl hemi ketal (4ml) is added dropwise to phosphoric acid heating at 165° C. Evolving trifluoroacetaldehyde is condensed at −78° C. and dissolved in ethyl acetate (6 ml).

(2) To a suspension of phosphorane (1) (1.38 g) in a mixture (60 ml) of dichloromethane and ethyl acetate (5:1) cooled at −70° C. is added the solution prepared as in above (1). After stirring at −70° C. for 10 minutes and 30 minutes at room temperature, the mixture is concentrated. The residue is purified by silica gel chromatography (eluting with a mixture (9:1) of benzene and ethyl acetate) to give trifluoropropene (2). Yield: 91%.

IR (CHCl$_3$) ν: 3380, 1787, 1722, 1682 cm$^{-1}$.

(3) To a solution of trifluoropropene (2) (292 mg) in benzene (5 ml) are added pyridine (89 microliter) and phosphorus pentachoride (208 mg). After 2 hours' stirring at room temperature, the mixture is diluted with methanol (5 ml). After 15 minutes' stirring, the reaction mixture is diluted with ice-water, neutralized, and extracted with ethyl acetate. The extract is washed with water, dried, and concentrated to give amine (3). Yield: 65%.

Preparation B-6

7beta-Amino-3-difluoromethylthio-3-cephem-4-carboxylic acid diphenylmethyl ester (7)

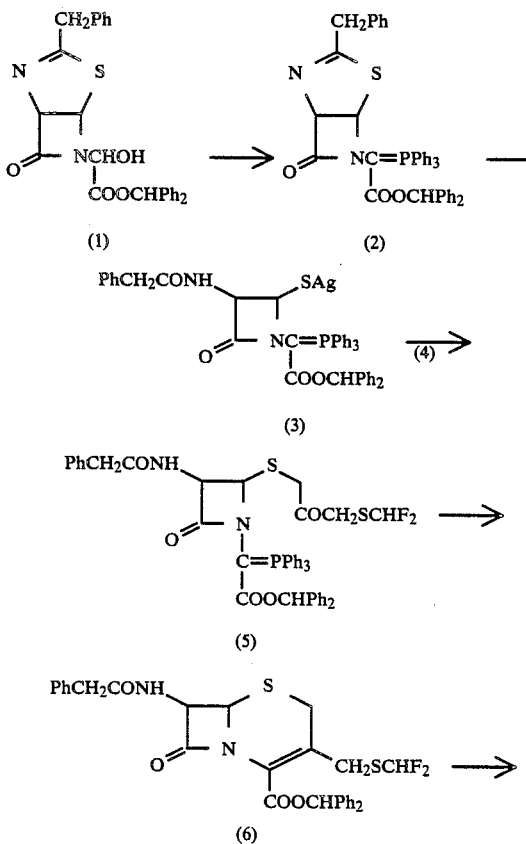

(1) To a suspension of glycolate (1) (22.8 g) in dichloromethane (300 ml) are added pyridine (4.63 ml) and thionyl chloride (4 ml) at −20° C. to −23° C. over a 24 minutes period. After stirring for 10 minutes at −20° C. and for 30 minutes at 0° C., the reaction mixture is washed with ice water and dried over magnesium sulfate. To the solution are added pyridine (4.63 ml) and triphenylphosphine (13 g). After stirring at room temperature for 2 hours and refluxing for 2 hours, the mixture is washed with water, and purified by silica gel chromatography (eluting with benzene-ethyl acetate (2:1) mixture) to give phosphoranilidene ester (2) (20.13 g).

(2) To a solution of phosphoranilidene ester (2) (16.65 g) in dioxane (80 ml) are added a solution of 99% silver perchlorate monohydrate (5.87 g) in water (19 ml) and aqueous 60% perchloric acid (7.96 ml) at room temperature. After stirring for 1 hour, the mixture is diluted with dichloromethane and iced water. The organic layer is taken, washed with water, dried, and concentrated to give silver mercaptide (3).

(3) To a solution of silver mercaptide (3) in hexamethylphosphorotriamide (100 ml) are added 1-(difluoromethylthio)-3-chloroacetone (4) (3.95 g) and sodium iodide (3.55 g). After 2 hour stirring at room temperature, the reaction mixture is diluted with ethyl acetate and water. The organic layer is taken, washed with water, dried, and evaporated. The residue is purified by silica gel chromatography (eluting with benzene-ethyl acetate (1:1) mixture) to give ketone (5).

Above 1-(difluoromethylthio)-3-chloroacetone (4) can be prepared as follows:

$$CHF_2SCH_2COCl \rightarrow CHF_2SCH_2COCH_2Cl \qquad (4)$$

To a solution of diazomethane in ether (200 ml) prepared from N-nitrosomethylurea (20.6 g) is added dropwise a solution of difluoromethylthioacetyl chloride (10 g) in ether (20 ml) under ice cooling over 20 minutes period. After stirring at 0° C. for 20 minutes and at room temperature for 2 hours, the mixture is saturated with hydrogen chloride under ice cooling over 30 minutes. The reaction mixture is diluted with ice water, ether layer is taken, washed with water, dried, concentrated, and distilled to give (4) from fractions evaporating at bp (1 mmHg) 52°–53° C. as colorless liquid.

(4) To a solution of ketone (5) (8.388 g) in toluene (200 ml) is added hydroquinone (180 mg) and refluxed for 14 hours. After evaporating toluene, the mixture is purified by silica gel chromatography (eluting with benzene-ethyl acetate (2:1) mixture) to give cephem (6) (4.42 g).

NMR (CDCl$_3$) δ: 3.58 (s, 2H), 3.73 (s, 2H).

(5) To an ice cold solution of cephem (6) (4.42 g) in dichloromethane (80 ml) are added pyridine (1.35 ml) and phosphorus pentachloride (3.17 g). After stirring at 0° C. for 10 minutes and at room temperature for 90 minutes, the mixture is cooled at −45° C. to −55° C., mixed with cold methanol (110 ml), stirred at 0° C. for 30 minutes, diluted with ice water, and neutralized. The organic layer is taken, washed with water, dried, and concentrated. The residue is purified by silica gel chromatography (eluting with benzene-ethyl acetate (2:1) mixture to give amine (7) (2.686 g).

NMR (CDCl$_3$) δ: 1.73 (brs, 2H) ppm.

TABLE 1
Esters

Structure: R⁰NH—[β-lactam with S]—C(=O)—CONH—CH(CH₂COOR³)—[thiazoline with S, N, O]—C(R⁵)=C(R⁶)—COOR⁸

| No | cis:trans | R⁰ | R³ | R⁵ | R⁶ | IR(CHCl₃) ν: cm⁻¹ | NMR(CDCl₃) δ: ppm | Example No. |
|---|---|---|---|---|---|---|---|---|
| 1 | cis | H | Me | H | H | nd | 3.70~4.30(m, 4H), 4.13, 4.16(2×s, 3H), 5.56, 5.62(2×d, J=5Hz, 1H), 6.20, 6.26(2×d, J=5Hz, 1H), 6.66~6.83(m, 1H), 6.90, 7.26(2×t, J=9Hz, 1H), 7.06, 7.13(2×s, 1H) [D₂O]. | (3-1) |
| 2 | cis | H | Me | H | BH | 1787, 1731, 1680, 1280. | 3.35~3.47(m, 2H), 3.58(d, J=8Hz, 2H), 3.70(s, 3H), 4.98(d, J=5Hz, 1H), 5.44(brs, 2H), 5.95, 6.04(dd, J₁=5Hz, J₂=9Hz, 1H), 6.47(s, 1H), 6.61(t, J=8Hz, 1H), 6.56~6.66(m, 1H), 6.95(s, 1H), 7.24~7.48(m), 8.56(d, J=9Hz, 1H). | (4-4) |
| 3 | trans | H | Me | H | BH | 1785, 1730, 1678, 1280. | 3.40(d, J=8Hz, 2H), 3.35~3.47(m, 2H), 3.68(s, 3H), 4.92(d, J=5Hz, 1H), 5.59(brs, 2H), 5.94, 6.03(dd, J₁=5Hz, J₂=9Hz, 1H), 6.48(s, 1H), 6.53~6.63(m, 1H), 6.90(s, 1H), 7.14(t, J=8Hz, 1H), 7.23~7.45(m, 10H), 8.65(d, J=9Hz, 1H). | (4-4) |
| 4 | cis | H | Bzl | H CF₃COOH salt | H | 3270, 1770, 1735, 1722 [Nujol]. | 3.44(d, J=7.5Hz, 2H), 3.54~3.67(m, 2H), 5.10(d, J=5Hz, 1H), 5.17(s, 2H), 5.80, 5.89(dd, J₁=5Hz, J₂=8Hz, 1H), 6.40(s, 1H), 6.42~6.59(m, 2H), 7.41 (s, 5H), 9.39(d, J=8Hz, 1H) [CD₃SOCD₃]. | (3-1) |
| 5 | trans | H | Bzl | H CF₃COOH salt | H | 3280, 1772, 1735, 1725 [Nujol]. | 3.54~3.69(m, 4H), 5.15(d, J=5Hz, 1H), 5.15(s, 2H), 5.78, 5.88(dd, J₁=5 Hz, J₂=8Hz, 1H), 6.45~6.53(m, 1H), 6.66(s, 1H), 6.78(t, J=7.5Hz, 1H), 7.40(s, 5H), 9.25(d, J=8Hz, 1H) [CD₃SOCD₃]. | (3-1) |
| 6 | cis H | Bzl | H | BH | | 1782, 1722, 1670, 1278. | 3.32~3.46(m, 2H), 3.62(d, J=8Hz, 2H), 4.95(d, J=5Hz, 1H), 5.13(s, 2H), (4-3) 5.31(brs, 2H), 5.92, 6.02(dd, J₁=5Hz, J₂=8Hz, 1H), 6.46(s, 1H), 6.53~6.61(m, 1H), 6.63(t, J=8Hz, 1H), 6.94(s, 1H), 7.21~7.47(m), 8.67(d, J=8Hz, 1H). | |
| 7 | trans | H | Bzl | H | BH | 1780, 1721, 1670, 1280. | 3.30~3.45(m, 4H), 4.88(d, J=5Hz, 1H), 5.11(s,2H), 5.52(brs, 2H), 5.92, 6.02(dd, J₁=5Hz, J₂=8Hz, 1H), 6.41(s, 1H), 6.50~6.65(m, 1H), 6.88(s, 1H), 7.15(t, J=7.5Hz, 1H), 7.16~7.48(m), 8.61(d, J=8Hz, 1H). | (4-3) |
| 8 | cis | Cbz | H | H | BH | 1782, 1725, 1675, 1555 [Nujol]. | 3.56(d, J=8Hz, 2H), 3.4~3.8(m, 2H), 5.04(d, J=5Hz, 1H), 5.26(s, 2H), 5.90(d, J=5Hz, 1H), 6.70(t, J=8Hz, 1H), 6.60~6.75(m, 1H), 6.95(s, 1H), 6.95(s, 1H), 7.25~7.55(m, 15H) [CDCl₃—CD₃OD]. | (3-9) |
| 9 | trans | Cbz | t-Bu | H | BH | 3330, 1775, 1725, 1670, 1630, mp. 162~164° C. | 1.34(s, 9H), 2.58~3.26(m, 4H), 5.68, 5.76(dd, J=5Hz, J=8Hz, 1H), 5.07, 5.51(ABq, J=13H z, 2H), 4.70(d, J=5Hz, 1H), 6.30~6.39(m, 1H), 6.61(s, 1H), 6.75(s, 1H), 7.10~7.57(m, 15H), 7.67(d, J=8Hz, 1H). | (2-1),(15 (5-1), (6-1), (3). |
| 10 | 15:85 | Cbz | CH₂—CH=CH₂ | H | BH | 3359, 1779, 1732, 1675, 1281, 1091. | nd | (2-17) |

TABLE 1-continued

Esters $$R^0NH-\overset{N}{\underset{O}{\bigsqcup}}\overset{S}{\underset{}{\bigsqcup}}-C(=CH-R^3)-CONH-\overset{S}{\underset{N}{\bigsqcup}}\overset{R^5}{\underset{CH_2COOR^3}{\bigsqcup}}COOR^8$$

| No | cis:trans | R⁰ | R³ | R⁵ | R⁶ | IR(CHCl₃) ν: cm⁻¹ | NMR(CDCl₃) δ: ppm | Example No. |
|---|---|---|---|---|---|---|---|---|
| 11 | 1:1 | Cbz | CHMe–CH=CH₂ | H | BH | 3358, 1779, 1730, 1675, 1283, 1092, mp. 150~151° C. | 1.06(d, J=7Hz, 1.5H), 1.18(d, J=7Hz, 1.5H), 2.63~3.32(m, 4H), 4.66(d, J=4.5Hz, 1H), 4.85~5.76(m, 6H), 6.31(m, 1H), 6.56(s, 1H), 6.68(s, 1/2H), 6.71(s, 1/2H). | (2-18) |
| 12 | | Cbz | CH₂–CMe=CH₂ | H | BH | 3345, 1780, 1735, 1679, 1287, 1092. | nd | (2-21) |
| 13 | 2:3 | Cbz | CH₂–CH=CHMe | H | BH | 3358, 1780, 1729, 1676, 1282, 1240, 1092. mp. 138~140° C. | 1.58(d, J=6Hz, 9/5H), 1.64(d, J=6Hz, 6/5H), 2.65~3.36(m, 4H), 4.38(d, J=6Hz, 2H), 4.69(d, J=5Hz, 1H), 5.06, 5.53(ABq, J=12Hz, 2H), 5.40~5.79(m, 3H), 6.28~6.39(m, 1H). | (2-18) |
| 14 | trans | Cbz | CH₂–CH=CMe₂ | H | BH | 3455, 1779, 1728, 1676, 1282, 1240, 1093. mp. 133~135° C. | 1.55(s, 3H), 1.61(s, 3H), 2.62~3.32(m, 4H), 4.52(d, J=8Hz, 2H), 4.64(d, J=4.5Hz, 1H), 5.18(m, 1H), 5.02, 5.50(ABq, J=12Hz, 2H), 5.67(dd, J=4.5 Hz, 8Hz, 1H), 6.29(m, 1H), 6.58(s, 1H), 6.68(s, 1H). | (2-20) |
| 15 | trans | Cbz | CH₂–CH=CMe₂ | H | BH | 3345, 1780, 1735, 1675, 1635. mp. 132~135° C. | 1.56(s, 3H), 1.62(s, 3H), 2.64~3.30(m, 4H), 4.45(brd, J=8Hz, 2H), 4.67(d, J=5Hz, 1H), 5.16(brt, J=8Hz, 1H), 5.03, 5.50(ABq, J=12Hz, 2H), 5.65, 5.74(dd, J=5Hz, J=8Hz, 1H), 6.27~6.36(m, 1H), 6.58(s, 1H), 6.69(s, 1H), 7.13~7.43(m, 16H), 7.60(d, J=8Hz, 1H). | |
| 16 | mixt. | Cbz | CH₂–CH=CHPh | H | BH | 3340, 1778, 1730, 1677, 1283, 1088. | nd | (2-17) |
| 17 | | Cbz | Bzl | H | H | nd | 3.00~3.90(m,4H), 4.96, 5.00(2×d,J=5Hz,1H), 5.13(s,2H), 5.23(s,2H), 5.73~5.88(m,1H), 5.76, 5.86(dd,J₁=5Hz, J₂=9Hz,1H), 6.50~6.60(m,1H), 6.93(s,1H), 7.11(t,J=8Hz,1H), 7.33(s,5H), 7.36(s,5H) [CDCl₃–CD₃OD]. | (2-7),(14) (3-1) |
| 18 | 1:4 | Cbz | Bzl | H | H | 3160, 1775, 1720, 1670, 1630. | 3.34~3.50(m, 4H), 4.95(d, J=5Hz, 1H), 5.13(s, 2H), 5.23(s, 2H), 5.80(d, J=5Hz, 1H), 6.48~6.60(m,1H), 6.94(m, 1H), 7.03~7.40(m, 11H). | (2-7),(14) (3-1) |
| 19 | 1:4 | Cbz | Bzl | H | BH | 3340, 1775, 1725, 1670. | 3.04(s, 2H), 3.6~4.1(m, 2H), 4.58(d, J=5Hz, 1H), 4.8~5.6(m, 4H), 5.68(d, J=5Hz, 1H), 6.25(m, 1H), 6.59, 6.67(2×s, 1H), 6.63(s, 1H), 7.0~7.9(m, 22H). | (2-1),(15) (21), (6-1). |

TABLE 1-continued

Esters

[Structure: R⁰NH-[β-lactam with S]-C(=O)-CONH-...-CH=C(R⁵)(COOR⁸), CH₂COOR³]

| No | cis: trans | R⁰ | R³ | R⁵ | R⁶ | IR(CHCl₃) ν: cm⁻¹ | NMR(CDCl₃) δ: ppm | Example No. |
|---|---|---|---|---|---|---|---|---|
| 20 | trans | Cbz | Bzl | H | BH | 3830, 1780, 1725, 1675, 1630. | 2.68~3.36(m, 4H), 4.69(d, J=5Hz, 1H), 4.98(s, 2H), 5.03, 5.46(ABq, J=12Hz, 2H), 5.65, 5.74(dd, J=5Hz, J=8Hz, 1H), 6.29~6.40(m, 1H), 6.64(s, 1H), 7.10~7.47(m, 15H), 7.63(d, J=8Hz, 1H). | (2-5),(21) (6-2), 7. |
| 21 | | Cbz | MeBzl | H | BH | mp. 131~133° C. 3340, 1775, 1725, 1670, 1630, 1560. | 2.30(s, 3H), 2.70~3.37(m, 4H), 4.71(d, J=5Hz, 1H), 4.95(d, 2H), 5.04, 5.49(ABq, J=12Hz, 2H), 5.67, 5.76(dd, J₁=5Hz, J₂=8Hz, 1H), 6.30~6.40(m, 1H), 6.62(s, 1H), 6.69(s, 1H), 7.05~7.47(m, 20H), 7.66(d, J=8Hz, 1H). | (2-7) |
| 22 | | Cbz | PMB | H | BH | 3325, 1770, 1720, 1665, 1625, 1605, 1505, 1400. | 2.60~3.65(m, 4H), 3.74(s, 3H), 4.67, 4.75(2×d, J=5Hz, 1H), 4.86~5.53(m, 4H), 5.65, 5.73; 5.82(2×dd, J₁=5Hz,J₂=7Hz, 1H), 6.25~6.50(m, 1H), 6.59~6.95(m, 4.5H), 7.05~7.50(m, 18.5H), 7.65, 7.90(2×d, J=7Hz, 1H). | (2-15), (18). |
| 23 | trans | BOC | Bzl | H | BH | 3400, 3330, 1773, 1720, 1668, 1278, 1152. | 1.50(s, 9H), 3.16(d, J=4.5Hz, 2H), 3.29(d, J=8Hz, 2H), 4.73(d, J=5Hz, 1H), 5.04(s, 2H), 5.68, 5.77(dd, J₁=5Hz, J₂=7.5Hz, 1H), 6.35(t, J=4.5Hz, 1H), 6.64(s, 1H), 6.71(s, 1H), 7.17~7.48(m), 7.79(d, J=7.5Hz, 1H). | (2-23) |
| 24 | cis | BOC | Bzl | H | BH | 3410, 3340, 1780, 1725, 1675, 1282, 1152. | 1.53(s, 9H), 3.15~3.37(m, 2H), 3.86(d, J=5Hz, 2H), 4.85(d, J=5Hz, 1H), 5.17(s, 2H), 5.82, 5.91(dd, J₁=5Hz, J₂=8Hz, 1H), 6.43~6.54(m, 1H), 6.70(t, J=7Hz, 1H), 6.79(s, 1H), 6.83(s, 1H), 7.15~7.49(m), 8.14(d, 1H). | (2-23) |
| 25 | | HCO | H | H | H | nd | 5.02(d, J=5Hz, 1H), 5.86(d, J=5Hz, 1H), 6.54~6.64(m, 1H), 7.04(t, J=8Hz, 1H), 7.16(s, 1H), 8.51(s, 1H) [CDCl₃—CD₃OD]. | (3-1),(2), (3). |
| 26 | trans | HCO | t-Bu | H | BH | 3420, 1770, 1715, 1665, 1625. | 1.39(s, 9H), 3.12(brd, 2H), 3.27(d, J=7Hz, 2H), 4.67(d, J=5Hz, 1H), 5.74, 5.83(dd, J₁=5Hz, J₂=8Hz, 1H), 6.29~6.38(m, 1H), 6.62(s, 1H), 6.83 (s, 1H), 7.20~7.47(m, 11H), 7.68(d, J=8Hz, 1H), 8.51(s, 1H). | (2-18) |
| 27 | 1:2 | HCO | BH | H | BH | 1775, 1772, 1672, 1280, 1152. | 3.60~3.16(m, 2H), 3.46, 3.87(2×d, J=8Hz, 2H), 4.65, 4.70(2×d, J=5Hz, 1H), 5.72, 5.81; 5.77, 5.86(2×dd, J₁=5Hz, J₂=8Hz, 1H), 6.26~6.45(m,1H), 6.61, 6.76(2×s, 1H), 6.66(s, 1H), 6.87, 6.95(2×s, 1H), 7.10~7.47(m), 7.64, 7.86(2×d, J=2Hz, 1H), 8.40, 8.43(2×s, 1H), 11.27, 11.51(2×brs, 1H). | (5-1) |
| 28 | 1:2 | Cl—CH₂CO | H | H | H | 1761, 1720, 1700 [Nujol] | 4.61, 4.75(2×s, 2H), 5.45, 5.51(2×d, J=5Hz, 1H), 6.08, 6.19(2×dd, J₁=5Hz, J₂=8Hz, 1H), 7.01, 7.30(2×t, J=8Hz, 1H), 7.60, 7.72(2×s, 1H), 8.26 8.74(2×d, J=8Hz, 1H) [CD₃SOCD₃]. | (3-2) |
| 29 | | Cl—CH₂CO | Bzl | H | H | 3150, 1770, 1718, 1680, 1278, 1152 [Nujol]. | 3.38~3.70(m, 4H), 4.38(s, 2H), 5.06(d, H=5Hz, 2H), 5.13(s, 2H), 5.73, 5.82(dd, J₁=5Hz, J₂=8Hz, 1H), 6.41~6.52(m,1H), 6.62(t, J=7.5Hz, 1H), 7.24(s, 1H), 7.38(s, 5H), 9.00(d, J=8Hz, 1H), 12.57(brs, 1H) [CD₃SOCD₃] | |
| 30 | 5:6 | Cl—CH₂CO | Bzl | H | BH | 3320, 1780, 1732, 1727, 1680. | 3.13, 3.26(m, 2H), 3.36, 3.76(2×d, J=8Hz, 2H), 4.16, 4.32(2× ABq, J=17Hz, 2H), 4.70, 4.79(2×d, J=5.0Hz, 1H), 5.06, 5.17(2×s, 2H), 5.69, 5.78; 5.78, 5.87(2×dd, J₁=5.0Hz, J₂=9.0Hz, 1H), 6.31~6.48(m, 1H), 6.66, 6.75(2×s, 1H), 6.72, 6.83(2×s, 1H), 6.67(t, 8Hz, 5H/11), 7.18~7.49 (m, 2H), 7.57(d, J=7.5Hz, 2H), 9.11, 9.16(2×d, J=7.5Hz, 2H) | (2-18) |
| 31 | trans | tBuSi=Me₂ | Bzl | H | BH | 3400, 1785, 1725, 1670, 1630. | 0.28, 0.78(s, 6H), 0.92(s, 9H), 3.47(d, J=7.5Hz, 2H), 4.79 (s, 1H), 4.98(d, H=5Hz, 1H), 5.16(s, 2H), 6.00, (dd, J₁=5Hz, J=9Hz, 1H), 6.48(s, 1H), 6.57~6.67(m, 1H), 6.98(s, 1H), 7.17(t, J=7.5Hz, 1H), 7.2~7.6(m, 15H), 8.65(d, J=9Hz, 1H). | (2-1) |

TABLE 1-continued

Esters

| No | cis:trans | R⁰ | R³ | R⁵ | R⁶ | IR(CHCl₃) ν: cm⁻¹ | NMR(CDCl₃) δ: ppm | Example No. |
|---|---|---|---|---|---|---|---|---|
| 32 | cis | tBuSi(=)Me₂ | Bzl | H | BH | 3390, 1780, 1720, 1670, 1630. | 0.28(s, 6H), 0.94(s, 9H), 3.17~3.75(m, 2H), 3.66(d, J=5Hz, 2H), 4.68 (s, 1H), 4.99(d, J=5Hz, 1H), 5.16(s, 2H), 6.00(dd, J₁=5Hz, J₂=9Hz, 1H), 6.50(s, 1H), 6.61, 6.66(2×s, 1H), 6.57~6.65(m, 1H), 6.68(t, J=7.5Hz, 1H), 6.97(s,1H), 7.1~7.6 (m, 15H), 8.35(d, J=9Hz, 1H). | (2-1) |
| 33 | cis | Cbz | Bzl | Me | BH | 3320, 1765, 1725, 1675. | 2.00(s, 3H), 2.27, 2.77(ABq, J=17Hz, 2H), 3.03, (AB part of ABX, J=16Hz, 3/2H), 3.63(AB part. of ABX, J=16Hz, 1/2H), 4.77(d, J=4Hz, 1H), 4.9~5.6 (m, 5H), 6.61, 6.66(2×s, 1H), 6.69, 6.75(2×s, 1H), 6.9~7.5(m, 21H), 7.70 7.89(2×d, J=7Hz, 1H). | (2-5) |
| 34 | 1:3 | Cbz | Bzl | CH=CH₂ | BH | 3330, 1770, 1725, 1675, 1620. | 2.70~3.94(m, 4H), 4.73, 4.79(2×d, J=4Hz, 1H), 4.90~5.30(m, 7H), 6.56~ 6.64(m,2H), 6.90~7.50(m, 22H), 7.74, 7.92(2×d, J=7Hz, 1H). | (2-15) |
| 35 | 2:1 | Cbz | Bzl | CH=CHCN(Z) | BH | 3407, 3345, 2210, 1783, 1728, 1679, 1631. | 2.7~4.2(m, 4H), 4.85, 4.92(2×d, J=4.5Hz, 1H), 5.07(s, 1H), 5.13(s, 2H), 5.20, 5.39(2×d, J=12Hz, 1H), 5.70(m, 1H), 6.49, 6.76(2×s, 1H), 6.63, 6.67(2×s, 1H), 6.5~8.1(m, 23H). | (2-3) |
| 36 | 2:1 | Cbz | Bzl | CH=CHCN(Z) | H | 3168, 2193, 1785, 1726, 1672 [Nujol]. | 3.50(m, 2H), 4.02(m, 2H), 5.13(d, J=4.5Hz, 1H), 5.17(s, 2H), 5.28(s, 2H), 5.45(d, J=12.5Hz, 1H), 5.90(d, J=4.5Hz, 1H), 6.95, 7.07(2×m, 1H), 6.98(s, 1H), 7.1~7.7(m, 11H) [CDCl₃-CD₃OD]. | (3-1) |
| 37 |  | Cbz | Bzl | CH=CHCOOt-Bu (E) | BH | 3391, 1779, 1728, 1618. | 1.41(s, 9H), 2.3~4.2(m, 4H), 5.04, 5.08(2×d, J=4.5Hz, 1H), 5.10(s, 2H), 5.17(s, 2H), 5.67(2×m, 1H), 5.94(d, J=16Hz, 1H), 6.63, 6.89(2×s, 1H), 6.72, 6.76(2×s, 1H), 6.4~7.7(m, 17H), 7.86(d, J=16Hz, 1H). | (2-7) |
| 38 |  | Cbz | Bzl | CH=CHCOOt-Bu (E) | H | 3170, 1780, 1730, 1613, 1302, 1229 [Nujol]. | 1.49(s, 9H), 3.3~4.2(m, 4H), 5.03, 5.07(2×d, J=4.5Hz, 1H), 5.14(s, 2H), 5.23(s, 2H), 5.82(2×m, 1H), 5.96(d, J=16Hz, 1H), 6.65(m, 0.5H), 6.91(s, 1H), 7.0~7.5(m, 10.5H), 7.86(d, J=16Hz, 1H). | (3-1) |
| 39 |  | Cbz | Bzl | CH=CHCF₃ (5E:2Z) | BH | 3330, 1775, 1725, 1675, 1620. | 2.7~3.6(m, 4H), 4.75~4.95(m, 1H), 4.95~6.0(m, 6H), 6.4~6.8(m, 2H), 7.05~ 7.85(m, 23H). | (2-16) |
| 40 |  | Cbz | Bzl | CH=CHCF₃ (Z) | H | 3325, 3390, 1775, 1725, 1672, 1625. | 2.7~3.8(m, 4H), 4.8~5.9(m, 7H), 6.55~6.85(m, 3H), 7.07~7.7(m, 22H). | (2-16) |
| 41 | 1:2 | Cbz | Bzl | CH₂N⊕C₅H₅Cl⊖ | BH | nd | 3.16, 3.68(ABq, J=18Hz, 2H), 3.51(d, J=8Hz, 2H), 5.12(s,2H), 5.28(s,2H), 5.20(d, J=5Hz, 1H), 5.82(d, J=5Hz, 1H), 5.37, 5.76(ABq, J=20Hz, 2H), 7.0, 7.15(2×s, 1H), 7.35(s, 5H), 7.42(s, 5H), 6.8~7.5(m, 1H), 8.0~9.3 (m, 5H) [CD₃OD—CD₃COCD₃—D₂O]. | (2.30) |
| 42 | cis | Cbz | Bzl | CH₂OMe | BH | 3390, 1780, 1728, 1675, 1304, 1092. | 3.16(s, 3H), 3.25(s, 2H), 3.54, 3.68(AB parts of ABX, J₁=19.2Hz, J₂= 7Hz, 2H), 4.14, 4.28(ABq, J=15.5Hz, 2H), 4.91(d, J=4.5Hz, 1H), 5.12(s, 2H), 5.16, 5.34(ABq, J=18Hz, 2H), 5.65(dd, J₁=4.5Hz, J₂=8.5Hz, 1H), 6.62 (t, J=7Hz, 1H), 6.75(s, 1H), 6.79(s, 1H), 7.23~7.40(m, 21H), 8.10(d, J= 8.5Hz, 1H). | (2-9) |
| 43 | trans | Cbz | Bzl | CH₂OMe | BH | 3425, 1778, 1726, 1675, 1302, 1090. | 2.95, 3.19(AB parts of ABX, J₁=17Hz, J₂=8.1Hz, 2H), 3.14(s, 3H), 3.18(s, 2H), 4.09, 4.27(ABq, J=13.5Hz, 1H), 4.80(d, J=4.5Hz, 1H), 5.02(s, 2H), 5.09, 5.37(ABq, J=12.6Hz, 2H), 5.50(dd, J₁=4.5Hz, J₂=7Hz, 1H), 6.57(s, 1H), 6.63(s, 1H), 7.10(t, J=8.1Hz, 1H), 7.20~7.42(m, 21H), 7.74(d, J= 7Hz, 1H). | (2-9) |

TABLE 1-continued

Esters $$R^0NH-\underset{\underset{O}{\|}}{C}-CONH-CH-\underset{\underset{CH_2COOR^3}{|}}{\overset{S}{\underset{|}{\bigcirc}}}\overset{R^5}{\underset{COOR^8}{=}}$$

| No | cis: trans | $R^0$ | $R^3$ | $R^5$ | $R^6$ | IR(CHCl$_3$) $\nu$ cm$^{-1}$ | NMR(CDCl$_3$) $\delta$: ppm | Example No. |
|---|---|---|---|---|---|---|---|---|
| 44 | | Cbz | Bzl | CH$_2$OCOMe | BH | 3400, 3330, 1775, 1725, 1670, 1625. | 1.96(s, 3H), 2.82~3.70(m, 4H), 4.56~5.73(m, 8H), 6.60~6.77, 7.04~7.50 (2×m, 23H). | (2-11) |
| 45 | 1:10 | Cbz | Bzl | CH$_2$OCONH$_2$ | BH | 3320, 1775, 1720, 1710 [Nujol]. | 3.49, 3.64(ABq, J=18Hz, 2H), 3.57(d, J=8Hz, 2H), 4.75, 4.97(ABq, J=12Hz, 2H), 5.15(s, 2H), 5.20(d, J=4Hz, 1H), 5.28(s, 3H), 5.75~6.30(m, 3H), 6.93(s, 1H), 7.10(t, J=8Hz, 1H), 7.20(s, 1H), 7.2~7.7(m, 20H) [CD$_3$COCD$_3$] | (2-1) |
| 46 | | Cbz | Bzl | CH$_2$SMe | BH | 1770, 1750, 1720, 1670. | 1.82(s, 3H), 3.3~3.7(m, 6H), 5.03(d, J=5Hz, 1H), 5.12(s, 2H), 5.25(s, 2H), 5.6~5.75(m, 1H), 6.89(s, 1H), 6.90(s, 1H), 6.66, 7.11(2×t, J=8Hz, 1H), 7.2~7.5(m, 20H) [CDCl$_3$—CD$_3$OD]. | (2-18) |
| 47 | | Cbz | Bzl | CH$_2$SCH$_2$CN | BH | 3230, 2245, 1785, 1730, 1680, 1620. | 2.7~3.4(m, 6H), 3.57, 3.77(ABq, J=14Hz, 2H), 4.93(d, J=4Hz, 1H), 5.06(s, 2H), 5.18, 5.27(2×s, 2H), 5.48(dd, J$_1$=4Hz, J$_2$=9Hz, 1H), 6.69(s, 1H), 6.76(s, 1H), 7.1~7.5(m, 20H), 8.46(d, J=9Hz, 1H). | (6-4) |
| 48 | | Cbz | Bzl | CH$_2$SCHF$_2$ | BH | 3400, 3330, 1735, 1725, 1675, 1630. | 3.14(t, J=9Hz, 2H), 4.87(d, J=5Hz, 1H), 5.05(s, 2H), 5.44 (dd, J$_1$=5Hz, J$_2$=8Hz, 2H), 6.60(t, J=56Hz, 1H), 6.15(s, 1H), 6.18(s, 1H), 7.10(t, J=9Hz, 1H), 7.2~7.4(m, 20H), 7.74(d, J=8Hz, 1H) | (2-27) |
| 49 | 2:3 | Cbz | Bzl | ![structure with HN-N, O-S ring, CH$_2$S] | BH | 3380, 3160br 1775, 1723, 1675, 1220. | 3.16~4.20(m, 6H), 4.81~5.26(m, 6H), 5.39~6.19(m, 1H), 6.63~6.85, 7.05~7.36(m, 24H), 7.47(s, 1H), 8.18, 8.48(2×d, J=8Hz, 2H). | (2-7) |
| 50 | 3:5 | MeCbz | MeBzl | ![structure with N-N, O-S ring, CH$_2$S] | BH | 1780, 1722, 1672. | 2.30(s, 6H), 2.77~3.27, 3.90~3.60, 4.17~4.57(3×m, 6H), 4.35(d, J=5Hz, 1H), 4.90~5.50(m, 5H), 6.60(s, 1H), 6.73(s, 1H), 7.00~7.50(m, 13H), 8.37 (s, 1H). | (2-10) |
| 51 | 1:1 | Cbz | Bzl | ![structure with N-N, O-S ring, CH$_2$S] | BH | 3403, 3175, 1775, 1721, 1670, 1542. | 3.36(d, J=8Hz, 2H), 3.59(brs, 2H), 4.36(Abq, J=14Hz, 2H), 4.98, 5.01(2× d, J=4Hz, 1H), 5.10(s, 2H), 5.22(s, 2H), 5.68, 5.78(2×d, J=4Hz, 1H), 6.87, 6.89, 6.91(3×s, 2H), 7.1~7.6(m, 21H), 8.93, 8.94(2×s, 1H) [CDCl$_3$—CD$_3$OD(10:1)]. | (2-8),(18) |
| 52 | | Cbz | Bzl | ![structure with N-N-Me, O-S ring, CH$_2$S] | BH | 3385, 3160, 1773, 1720, 1668, 1541. | 2.61(s, 3H), 3.36(d, J=8Hz, 2H), 3.54(brs, 2H), 4.30(ABq, J=14Hz, 2H), 4.96, 5.00(2×d, J=4Hz, 1H), 5.11(s, 2H), 5.23(s, 2H), 5.68, 5.77(2×d, J=4Hz, 1H), 6.88(s, 2H), 7.00~7.55(m, 22H) [CDCl$_3$—CD$_3$OD(10:1)]. | (2-28),(18) |
| 53 | 1:1 | Cbz | Bzl | ![structure with N-N-NH-BOC, O-S ring, CH$_2$S] | BH | 3380, 3170, 1780, 1725, 1675, 1603, 1564. | 3.47(d, J=8Hz, 2H), 3.52(brs, 2H), 4.09(brs, 2H), 4.97, 5.01(2×d, J=4Hz, 1H), 5.11, 5.13(2×s, 2H), 5.23(s, 2H), 5.72, 5.78(2×d, J=4Hz, 2H), 6.86, 6.89, 6.90(3×s, 2H), 7.00~7.60(m, 20H), 6.65, 7.12(2×t, J=8Hz, 1H) [CDCl$_3$—CD$_3$OD(10:1)]. | (2-25) |

TABLE 1-continued

Esters

| No | cis: trans | R⁰ | R³ | R⁵ | R⁶ | IR(CHCl₃) ν: cm⁻¹ | NMR(CDCl₃) δ: ppm | Example No. |
|---|---|---|---|---|---|---|---|---|
| 54 | 1:1 | Cbz | Bzl | BOC-NH-CH₂ / N-N / CH₂S- (thiadiazole) | BH | 3385, 3170, 1779, 1723, 1673, 1620, 1560. | 3.38(d, J=8Hz, 2H), 3.51(brs, 2H), 4.06(brs, 2H), 4.98, 5.01(2×d, J=4Hz, 1H), 5.11(s, 2H), 5.20(s, 2H), 5.78(d, J=4Hz, 1H), 6.87 (s, 1H), 6.90(s, 1H), 7.00~7.60(m, 22H) [CDCl₃—CD₃OD(10:1)]. | (2-15) |
| 55 | cis | Cbz | Bzl | Cl-CH₂CO- | BH | 3400, 1785, 1725, 1670. | 3.40(s, 2H), 3.61(d, J=Hz, 2H), 3.73(s, 3H), 4.11 4.43(ABq, J=14Hz, 2H) 4.91(d, J=5Hz, 2H), 5.11(s, 2H), 5.14, 5.24(ABq, J=12Hz, 2H), 5.65(dd, J₁=8Hz, J₂=5Hz, 1H), 6.62(t, J=7Hz, 1H), 6.78(s, 1H), 6.81(s,1H), 7.1~7.6(m, 20H), 8.27(d, J=8Hz, 1H). | (2-29) |
| 56 | trans | Cbz | Bzl | MeN—N / CH₃S-N | BH | 1785, 1730, 1675. | 2.98(d, J=8Hz, 2H), 3.23(s, 2H), 3.76(s, 3H), 3.98, 4.52(ABq, J=14Hz, 2H), 4.80(d, J=5Hz, 1H), 5.06(s, 2H), 5.10(s, 2H), 5.40(dd, J₁=5Hz, J₂=6Hz, 1H), 6.52(s, 1H), 6.77(s, 1H), 7.08(t, J=8Hz 1H), 6.81 (s, 1H), 7.1~7.6(m, 20H), 7.77(d, J=6Hz, 1H). | (2-29) |
| 57 | | Cbz | Bzl | Ome | BH | 3325, 1760, 1715, 1670, 1625. | 1.98 2.69(ABq, J=16Hz, 2H), 2.76~4.01(m, 2H), 3.52(s, 3H), 4.92~5.54(m, 6H), 6.66(s, 1H), 6.88(s, 1H), 7.01~7.50(m, 2H). | (2-15) |
| 58 | | Cbz | Bzl | OSO₂Me | BH | 3340, 1785, 1675, 1630. | 2.65~3.75(m, 2H), 2.94(s, 3H), 3.51(brs, 2H), 4.86(d, J=5Hz, 1H), 5.03 (s, 2H), 5.02, 5.49(ABq, J=13Hz, 2H), 5.61, 5.70(s, 2H), 5.02 5.49(ABq, J=13Hz, 2H), 5.61, 5.70(dd, J₁=5Hz, J₂=8Hz, 1H), 6.50, 6.53 (6.60(3×s, 2H). | (2-12) |
| 59 | 1:2 | Cbz | Bzl | Cl | BH | 3350, 1785, 1740, 1685, 1635. | 2.64~3.95(m, 2H), 3.37(brs, 2H), 4.78, 4.80(2×d, J=6Hz, 1H), 4.94~5.13 (m, 2H), 5.00, 5.10(2×s, 2H), 5.58(dd, J₁=8Hz, J₂=8Hz, 1H), 6.55~6.67; 6.95~7.50(2×m 23H). | (2-28) |
| 60 | | BOC | Bzl 2-Cephem isomer | Cl | PNB | 1778, 1745, 1727, 1675, 1350, 1150, 2H). | 1.52(s, 9H), 3.38(d, J=8Hz, 2H), 4.89(d, J=2Hz, 1H), 5.13(s, 2H), 5.28 (d, J=4Hz, 1H), 5.31(s, 2H), 5.43, 5.51(dd, J₁=4Hz, J₂=7Hz, 1H), 6.35(d, J=2Hz, 1H), 6.93(s, 1H), 7.18(t, J=8Hz, 1H), 7.33(s, 5H), 7.52(d, J=8Hz, 2H), 8.20(d, J=7Hz, 1H), 8.23(d, J=8Hz, 2H), 8.99(brs, 1H). | (2-24) |
| 61 | | MeCbz | MeBzl | SCH₂CH₂F | PNB | 3340, 1780, 1732, 1676, 1620, 1606, 1528. | 2.32(s, 6H), 2.7~3.3(m, 4H), 3.39(s, 2H), 4.49(dt, J₁=47Hz, J₂=6Hz, 2H), 4.82(d, J=4Hz, 1H), 5.02(s, 2H), 4.68, 5.48(ABq, J=19Hz, 2H), 5.21(s, 2H), 6.83(s, 1H), 7.0~7.3(m, 9H), 7.46(d, J=9Hz, 1H), 7.67(d, 8Hz, 1H), 8.14(d, J=9Hz, 2H). | (2-17) |
| 62 | | MeCbz | MeBzl | SCH₂CH₂F | BH | 3345, 1757, 1730, 1672, 1630, 1557, 1528. | 2.26(s, 6H), 2.1~2.7(m, 2H), 2.7~3.3(m, 4H), 4.31(dt, J₁=6Hz, J₂=46Hz, 2H), 4.8~4.5(m, 6H), 6.65(s, 1H), 6.80(s, 1H), 7.0~7.7(m, 2H). | (2-5) |
| 63 | 1:1 | Cbz | Bzl | SCH₂CF₃ | PNB | 3330, 1775, 1725, 1665. | 2.8~3.7(m, 6H), 4.75~5.75(m, 8H), 6.82(s, 1H), 7.0~7.7(m, 12H), 7.45, 8.15(ABq, J=9Hz, 4H). | (2-22) |
| 64 | | Cbz | Bzl | SCH₂CF₃ | H | 3170br 1775, 1725, 1670. | nd | (3-1) |

TABLE 1-continued

Esters $R^0NH$—[β-lactam structure with S]—CONH—CH(CH$_2$COOR$^3$)—[fused bicyclic β-lactam with S]—C(COOR$^8$)=R$^5$

| No | cis:trans | R$^0$ | R$^3$ | R$^5$ | R$^6$ | IR(CHCl$_3$) $\nu$: cm$^{-1}$ | NMR(CDCl$_3$) $\delta$: ppm | Example No. |
|---|---|---|---|---|---|---|---|---|
| 65 | | Cbz | Bzl | SCH=CH$_2$ | BH | 3320, 1770, 1750, 1720, 1670. | 2.5~3.8(m 4H), 4.7~5.8(m, 8H), 5.9~8.0(m, 26H). | (2-17) |
| 66 | | Cbz | Bzl | SCH=CH$_2$ | PNB | 3325, 1775, 1720, 1670. | 2.7~3.8(m, 2H), 3.43(s, 2H), 4.75~5.70(m, 10H), 6.25~8.3(m, 19H), | (2-17) |

TABLE 1 (2)

Esters

| No. | cis: trans | $R^0$ | $R^1$ | $R^2$ | $R^3$ | $R^5$ | $R^8$ | IR(CHCl$_3$)$\nu$: cm$^{-1}$ | NMR(CDCl$_3$)$\delta$: ppm | Example No. |
|---|---|---|---|---|---|---|---|---|---|---|
| 1 | cis | Cbz | H | — | Bzl | Me | BH | 3400, 1765, 1720, 1680. | 1.96(s, 3H), 2.60. 3.68(ABq, J=18Hz, 2H), 4.88(d, J=4.5Hz. 1H). 5.07(s, 2H), 5.13, 5.27(ABq, J=12Hz, 2H), 5.88(dd, J$_1$=4.5Hz, J$_2$=7Hz, 1H), 6.59(s, 1H), 6.86(s, 1H), 7.01(s, 1H), 7.0~7.6(m, 20H), 8.21(d, J=7Hz, 1H). | (2-28) |
| 2 | cis | Cbz | H | 13 | Bzl | CH=CH$_2$ | BH | 3400, 1770, 1725, 1685. | 3.06 3.18(ABq, J=18Hz, 2H), 4.95(d, J=5Hz, 1H), 4.9~5.4(m, 6H), 5.93(dd, J$_1$=5Hz, J$_2$=7.5Hz, 1H), 6.60(s, 1H), 6.89 (s, 1H), 7.00 (s, 1H), 6.85~7.6(m, 21H), 8.21(d, J=7.5Hz, 1H), 10.09(brs, 1H). | (2-23) |
| 3 | cis | Cbz | H | — | Bzl | CH$_2$OCOMe | BH | 1770, 1725, 1680. | 1.98(s, 3H), 2.88, 3.28(ABq, J=19Hz, 2H), 4.52~5.22(m, 7H), 5.93 (dd, J$_1$=8Hz, 1H), 6.60(s, 1H), 6.88(s, 1H), 7.02(s, 1H), 7.0~7.6(m, 20H), 8.00(d, J=8Hz, 1H). | (2-17) |
| 4 | trans | Cbz | H | — | Bzl | CH$_2$OCOMe | BH | 1780, 1735, 1675. | 1.97(s, 3H), 3.18(brs, 1H), 4.85(d, J=5Hz, 1H), 4.52~5.57(m, 7H), 6.70(s, 1H), 6.98(s, 1H), 7.1~7.6(m, 20H), 7.90(d, J=7.5Hz. 1H). | (2-17) |
| 5 | cis | Cbz | H | CH$_2$CH$_2$ | Bzl | H | BH | 3350, 1770, 1720, 1660, 1620, 1520, 1390, 1270. | 2.55(m, 4H), 3.30(m, 2H), 4.85(d, J=6.0Hz, 1H), 5.06(s, 4H), 5.90(m, 1H), 6.40(m, 1H), 6.63(s, 1H), 6.81(s, 1H), 7.30(m, 21H). | (2-20) |
| 6 | trans | Cbz | H | CH$_2$CH$_2$ | Bzl | H | BH | 3350, 1770, 1720, 1660, 1620, 1520, 1390, 1270. | 2.30(m, 4H), 3.08(m, 2H), 4.63(d, J=6.0Hz, 1H), 5.00(s, 4H), 5.70(m, 1H), 6.29(m, 1H), 6.53(s, 1H), 6.56(m, 1H), 6.98(m, 1H), 7.30(m, 21H). | (2-20) |
| 7 |  | Cbz | H | >CHMe | Bzl | H | BH | 3330, 1770, 1725 1670. | 0.9~1.5(2×d, 3H), 3.0~3.3(m, 2H), 3.4~4.5(m, 1H). | (2-21) |
| 8 | exo | Cbz | H | >CHMe | Bzl | H | BH | 3390, 1785, 1735 1690sh. | 1.74, 1.79, 1.90 2.00(4×s, 3H), 3.1~3.4(m, 2H) | (2-21) |
| 9 | cis | Cbz | H | (CH$_2$)$_2$ | Bzl | H | BH | 3325, 2900, 1770, 1720, 1660, 1620, 1520, 1400, 1286. | 1.75(m, 2H), 2.30(m, 4H), 3.25(m, 2H), 4.80(d, J=6.0Hz, 1H), 5.08(s, 4H), 5.75(m, 1H), 6.32(m, 1H), 6.61(s, 1H), 6.78(s, 1H), 6.90(m, 1H), 7.30(m, 21H). | (2-21) |
| 10 | trans | Cbz | H | (CH$_2$)$_2$ | Bzl | H | BH | 3325, 2910, 1770, 1720, 1660, 1620, 1530, 1400, 1280. | 1.70(m, 4H), 2.22(m, 4H), 3.11(m, 2H), 4.65(d, J=6Hz, 1H), 5.02 (s, 4H), 5.70(m, 1H), 6.30(m, 1H), 6.48(s, 1H), 6.60(s, 1H), 7.00(m, 1H), 7.30(m, 21H). | (2-21) |
| 11 | cis | BOC | H | >CMe$_2$ | Bzl | H | BH | 3390, 1780, 1720, 1665. | 1.52(s, 15H), 3.1~3.7(m, 2H), 4.91(d, J=5Hz, 1H), 5.13(s, 2H), 5.87(dd, J$_1$=5Hz, J$_2$=8Hz, 1H), 6.45(s, 1H), 6.54~6.64(m, 1H), 6.82(s, 1H), 6.94(s, 1H), 7.1~7.5(m, 15H). | (2-6) |

TABLE 1 (2)-continued

Esters $R^0NH$-(N-O-S)-C(=CR^1)-CONH-(structure with S, N, O)-CR^5=C(COOR^6), R^2COOR^3

| No. | cis: trans | $R^0$ | $R^1$ | $R^2$ | $R^3$ | $R^5$ | $R^8$ | IR(CHCl$_3$)ν: cm$^{-1}$ | NMR(CDCl$_3$)δ: ppm | Example No. |
|---|---|---|---|---|---|---|---|---|---|---|
| 12 | trans | BOC | H | $\diagup$CMe$_2$ | Bzl | H | BH | 3400, 3340, 1780, 1720, 1665. | 1.34(s, 3H), 1.36(s, 3H), 1.52(s, 9H), 3.09(d, J=4Hz, 2H), 4.50, 4.78(ABq, J=12 Hz, 2H), 4.67(d, J=5Hz, 1H), 5.62(dd, J$_1$=5Hz, J$_2$=8Hz, 1H), 6.32(t, J=4Hz, 1H), 6.51(s, 1H), 6.61(s, 1H), 7.11(s, 1H), 7.1~7.5(m, 15H). | (2-6) |
| 13 | 3:2 | Cbz | Cl | — | Bzl | H | BH | 3400, 1780, 1720. | nd | (2-1) |
| 14 | 1:1 | Cbz N—MEM | Cl | CH$_2$CH$_2$ | Bzl | H | BH | 3390, 1785, 1715, 1670 | 2.6~3.0(m, 2H), 3.25(s, 3H), 3.0~3.6(m, 4H), 3.55~3.85(m, 2H), 4.97, 5.02(d×d, J=4.5Hz, 1H), 5.09, 5.11(2×s, 2H), 5.33(s, 2H), 5.55 5.67(2×s, 2H), 5.8~6.2(m, 1H), 6.55~6.75(m, 1H), 6.95(s, 1H), 7.03(2×s, 1H), 6.95(s, 1H), 7.15~7.6(m, 21H). | (2-16) |
| 15 |  | Cbz | Cl | (CH$_2$)$_3$ | Bzl | H | BH | 1785, 1725. | 1.70~2.90(m, 6H), 3.25~3.50(m, 2H), 4.87(d, J=5Hz, 1H), 5.00(s, 2H), 5.23(s, 2H), 5.95(dd, J$_1$=5Hz, J$_2$=9Hz, 1H), 6.53(t, J=4Hz, 1H), 6.71(s, 1H), 6.82(s, 1H), 7.0~7.5(m, 20H). | (2-21) |
| 16 |  | Cbz | Cl | SCH$_2$ | Bzl | H | BH | nd | 3.23(brs, 2H), 3.60(s, 2H), 4.80(d, J=5Hz, 1H), 5.03(s, 2H), 5.07, 5.50(ABq, J=12Hz, 2H), 5.83(dd, J$_1$=5Hz, J$_2$=9Hz, 1H), 6.35(t, J=4Hz, 1H), 6.77(s, 1H), 6.90(s, 1H), 7.0~7.6(m, 20H). | (2-21) |

TABLE 1 (3)

Esters

| No | cis: trans | X | R¹ | R² | R⁴ | R⁵ | IR(CHCl₃) ν: cm⁻¹ | NMR(CDCl₃) δ: ppm | Example No. |
|---|---|---|---|---|---|---|---|---|---|
| 1 | cis | SO α | H | CH₂ | H | H | 1795, 1725, 1670. | 3.1~4.12(m, 2H), 3.57(d, J=7Hz, 2H), 4.54(d, J=5Hz, 1H), 5.07(s, 2H), 5.18(s, 2H), 5.61(dd, J₁=5Hz, J₂=7Hz, 1H), 6.3~6.4(m, 1H), 6.60(t, J=7Hz, 1H), 6.85(s, 1H), 6.88(s, 1H), 7.1~7.5(m, 20H), 8.53(d, J=7Hz, 1H). | (2-20) |
| 2 | trans | SO α | H | CH₂ | H | H | nd | 2.9~4.15(m, 4H), 4.45(d, J=5Hz, 1H), 5.06(s, 2H), 5.10, 5.30(ABq, J=12Hz, 2H), 5.47(dd, J₁=5Hz, J₂=7Hz, 1H), 6.2~6.4(m, 1H), 6.77(s, 1H), 6.82(s, 1H), 7.11(t, J=8Hz, 1H), 7.1~7.5(m, 20H), 8.03(d, J=7Hz, 1H). | (2-20) |
| 3 | trans | SO β | H | CH₂ | H | H | 1800, 1720, 1670. | 3.0~3.9(m, 2H), 3.37(d, J=7Hz, 2H), 4.36(d, J=5Hz, 1H), 5.10(s, 2H), 5.18(s, 2H), 6.16(dd, J₁=5Hz, J₂=9Hz, 1H), 6.3~6.4(m, 1H), 6.84(s, 1H), 6.92(s, 1H), 7.1~7.5(m, 21H), 9.56(d, J=9Hz, 1H). | (2-20) |
| 4 | trans | SO | H | CH₂ | H | CH₂SCH₂CN | 3200, 2245, 1800, 1720, 1672, 1615, 1550. | 2.81(s, 2H), 3.34(d, J=7Hz, 2H), 3.60(s, 2H), 3.24, 3.79(ABq, J=17Hz, 2H), 4.52(d, J=5Hz, 1H), 5.08(s, 2H), 5.14(s, 2H), 6.15(dd, J₁=5Hz, J₂=10Hz, 1H), 6.78(s, 1H), 6.94(s, 1H), 7.1~7.5(m, 20H), 9.54(d, J=10Hz, 1H), 9.67(brs, 1H). | (2-11) B-4 |
| 5 | 1:1 | SO | H | CH₂ | H | [thiazoline with CH₃S] | 1800, 1722, 1668. | 2.29(s, 3H), 2.30(s, 3H), 3.27, 3.80(ABq, J=18Hz, 2H), 3.31, 3.40(2×d, J=8Hz, 2H), 4.00(brs, 2H), 4.50(d, J=5Hz, 1H), 5.07, 5.11(2×s, 4H), 6.08, 6.19(dd, J₁=10Hz, J₂=5Hz, 1H), 6.81(s, 1H), 6.83(s, 1H), 6.97~7.43(m, 19H), 8.33(s, 1H), 9.43(brs, 1H), 9.71(d, J=10Hz, 1H). | (2-11) |
| 6 | 1:1 | SO | H | CH₂ | H | OH | 1800, 1730, 1640, 1615. | 3.30~3.80(m, 4H), 4.66(d, J=5Hz, 1H), 5.14(s, 2H), 5.23(s, 2H), 5.93(d, J=5Hz, 1H), 6.84(s, 1H), 6.88(s, 1H), 7.10~7.70(m) [CDCl₃—CD₃OD]. | (2-10) |
| 7 | 1:1 | O β | H | CH₂ | OMe | CH=CH₂ | 3380, 3150, 1765, 1710, 1675. | 2.80~3.90(m, 2H), 3.30, 3.47(2×s, 3H), 4.0~5.5(m, 9H), 6.4~6.85(m, 3H), 7.1~7.7(m), 8.13, 8.36(2×s, 1H). | (2-15) |
| 8 | 1:1 | O | H | CH₂ | OMe | [thiazoline with MeN, CH₃S] | 1770, 1720, 1685. | 2.1~4.0(m, 2H), 3.30, 3.40(2×s, 3H), 3.74, 3.78(2×s, 3H), 4.1~5.2(m, 9H), 6.18, 6.46(2×s, 1H), 6.61(t, J=7Hz, 0.5H), 6.80, 6.83(2×s, 1H), 7.0~7.6(m, 20.5H), 7.89, 8.24(2×s, 1H). | (2-15) |

TABLE 1 (4)

Esters $$R-\underset{\underset{CH}{\parallel}}{C}-CONH-\underset{\underset{R^2-COOBzl}{|}}{\overset{S}{\underset{N}{\bigcup}}}\overset{R^5}{\underset{O}{\bigcup}}COOBH$$

| No | cis: trans | R | R² | R⁵ | IR (CHCl₃)ν: cm⁻¹ | NMR(CDCl₃)δ: ppm | Example No. |
|---|---|---|---|---|---|---|---|
| 1 | 1:3 | Ph | CH₂ | H | 3390, 1790, 1730, 1680, 1630. | 3.06, 3.37(2×d, J=8Hz, 2H), 3.20~3.70(m, 2H), 4.92(d, J=5Hz, 1H), 5.10, 5.14 (2×s, 2H), 5.96(d, J=5Hz, 1H), 6.50~6.63(m, 1H), 6.92(s, 1H), 7.10~7.45(m). | (2-26) |
| 2 | trans |  | CH₂ | H | 3390, 1785, 1725, 1675, 1630, 1495. | 3.23(d, J=8Hz, 2H), 3.15~3.75(m, 2H), 4.94(d, J=5Hz, 1H), 5.12(s, 2H), 5.88, 5.98(dd, J₁=5Hz, J₂=10Hz, 1H), 6.36(d, J=10Hz, 1H), 6.52~6.63(m, 1H), 6.92~7.50(m, 20H). | (2-28) |
| 3 | 1:4 |  | CH₂ | MeN–N=⫿(CH₂S) | 3380, 1785, 1720, 1675, 1620. | 3.21, 3.54(2×d, J=8Hz, 2H), 3.68(s, 2H), 3.80(s, 3H), 4.22, 4.35(ABq, J=15Hz, 2H), 4.96(d, J=5Hz, 1H), 5.11, 5.13(2×s, 2H), 5.86, 5.96(dd, J₁=5Hz, J₂=9Hz, 1H), 6.34(d, J=9Hz, 1H), 6.90~7.46(m, 20H). | (2-28) |
| 4 | 5:4 | BOCNH––N–O | CH₂ | H | 3405, 1785, 1682, 1635. | 1.49(s, 9H), 3.10~3.75(m, 2H), 4.95, 4.97(2×d, J=4.5Hz, 1H), 5.93(dd, J₁=9Hz, J₂=4.5Hz, 1H), 5.14(s, 2H), 6.50~6.75(m, 1H), 6.85, 6.97(2×s, 1H), 6.95(s, 1H), 7.10~7.80(m, 17H). | (2-10) |
| 5 | 1:1 | N– | CH₂ | H | 1790, 1725, 1680, 1630. | 3.37, 3.72(2×d, J=8Hz, 2H), 3.05~3.80(m, 2H), 4.96(d, J=5Hz, 1H), 5.13(s, 2H), 5.95, 6.04(dd, J₁=5Hz, J₂=9Hz, 1H), 6.55~6.66(m, 1H), 6.83(t, J=8Hz, 0.5H), 6.95(s, 1H), 7.20~7.50(m, 16.5H), 8.52(d, J=9Hz, 1H), 8.75, 8.84(d, J=2Hz, 1H). | (2-7) |
| 6 | trans | NO₂-p PhCH=N– | CH₂ | H | 1780, 1720, 1670, 1620, 1515, 1340. | 3.13~3.73(m, 2H), 3.50(d, J=7.5Hz, 2H), 5.02(d, J=5Hz, 1H), 5.17(s, 2H), 5.99 (dd, J₁=5Hz, J₂=8Hz, 1H), 6.57~6.68(m, 1H), 6.99(s, 1H), 7.2~7.6(m, 17H), 8.07, 8.21(ABq, J=9Hz, 4H), 8.71(d, J=8Hz, 1H), 9.20(s, 1H). | (2-27) |
| 7 | cis | NO₂-p PhCH=N– | CH₂ | H | 1780, 1720, 1665, 1625, 1515, 1340. | 3.13~3.75(m, 2H), 3.77(d, J=7Hz, 2H), 5.03(d, J=5Hz, 1H), 5.18(s, 2H), 5.98 (dd, J₁=5Hz, J₂=8Hz, 1H), 6.60~6.70(m, 1H), 6.92(t, J=7Hz, 1H), 7.01(s, 1H), 7.2~7.6(m, 16H), 8.09, 8.23(ABq, J=8Hz, 4H), 8.83(d, J=8Hz, 1H), 9.21(s, 1H). | (2-27) |
| 8 | 1:1 | CbzNH– | CH₂ | H | 1780, 1730, 1540, 1280. | 3.91~3.31(m, 1H), 3.64, 3.50(ABq, J=10Hz, 1H), 3.67, 3.81(2×d, J=7Hz, 2H), 4.71, 4.84(2×d, J=5Hz, 1H), 5.04, 5.11(2×s, 1H), 5.22, 5.29(ABq, J=12Hz, 1H), 5.22(m, 1H), 5.6~6.1(m, 0.5H), 6.3~6.7(m, 1H), 6.22, 6.87(2×s, 1H), 7.2~7.7(m, 23H), 8.33, 9.07(2×s, 1H). | (2-1) |
| 9 | cis | CbzNH– | — | H | 3200, 1770, 1730, 1690, 1550, 1290. | 2.78~3.24(m, 2H), 4.88(d, J=5Hz, 1H), 5.11(s, 2H), 5.17, 5.32(ABq, J=13Hz, 2H), 6.09, 6.19(dd, J₁=8Hz, J₂=5Hz, 1H), 6.52(m, 1H), 6.86(s, 1H), 7.01(s, 1H), 7.27(m, 20H), 8.46(d, J=8Hz, 1H). | (2-1) |

TABLE 2(1)

Carboxylic acids

| No. | cis/trans | R³ | R⁵ | R⁸ | IR ν : cm⁻¹ | NMR δ : ppm | Example No. |
|---|---|---|---|---|---|---|---|
| 1 | 1:1 | H | H | H | 1763, 1705, 1630 [KBr]. | 3.22(d, J=7Hz, 1H), 3.42(d, J=7Hz, 1H), 3.60(s, 2H), 5.07, 5.11(2×d, J=5Hz, 1H), 5.81(d, J=5Hz, 1H), 6.31, 6.57(2×s, 1H). | 3-(1), 4-(1). |
| 2 | cis | H | H (HCl salt) | H | 3425, 3300, 3260, 1760, 1715, 1657, 1620, 1548 [Nujol] | 3.31(d, J=7Hz, 2H), 3.54∼3.63(brs, 2H), 5.21(d, J=5Hz, 1H), 5.79(d, J=5Hz, 1H), 6.54∼6.83(m, 2H), 6.63(s, 1H) [CD₃COCD₃—CD₃OD—D₂O]. | 3-(1)(2), 4-(1)(2), 9. |
| 3 | cis | H | H | H | 3580, 3260, 1770, 1700, 1650, 1572, 1546, 1362 [Nujol] | 3.68(d, J=8Hz, 2H), 3.9(A part of ABX, J₁=3.5Hz, J₂=20Hz, 1H), 4.13(B part of ABX, J₁=5.5Hz, J₂=20Hz, 1H), 5.65(d, J=5Hz, 1H), 6.30(d, J=5Hz, 1H), 6.78(X part of ABX, J₁=3.5Hz, J₂=5.5Hz, 1H), 6.95(t, J=8Hz, 2H), 7.05(s, 1H) [CD₃SOCD₃—CD₃OD]. | (3-(1), 4-(1)), 8. |
| 4 | 1:1 | H | Me | H | 1760, 1710, 1630 [KBr]. | 2.13(s, 3H), 3.39(d, J=7Hz, 2H), 5.03(d, J=4.5Hz, 1H), 5.08(d, J=4Hz, ½H), 5.73(d, J=4.5Hz), 5.76(d, J=4Hz, ½H), 6.43, 6.54(2×s, 1H), 6.61, 6.94(2×t, J=7Hz, 1H) [CD₃SOCD₃—CD₃OD—CDCl₃]. | 1-(4), 3-(2). |
| 5 | 1:1 | H | CH=CH₂ | H | 3280, 1760, 1630 [Nujol]. | 3.66(d, J=8Hz, 2H), 4.10(brs, 2H), 5.62∼5.96(m, 3H), 6.16, 6.22(2×d, J=4Hz, 1H), 6.85∼7.46(m, 3H) [D₂O]. | 1-(4), 4-(2). |
| 6 | 1:1 | H | CH=CHCN | H | 3195, 2205, 1764, 1611 [Nujol]. | 3.3∼4.2(m, 4H), 5.08, 5.15(2×d, J=4.5Hz, 1H), 5.26(d, J=12Hz, 1H), 5.63, 5.71(2×d, J=4.5Hz, 1H), 6.35, 6.43(2×s, 1H), 5.90(d, J=16Hz, 1H), 6.36, 6.76(2×m, 1H), 6.45, 6.53(2×s, 1H), 6.98(m, 1H) [NaHCO₃—D₂O]. | 1-(1), 3-(2). |
| 7 | 1:1 | H | CH=CHCOOH (E) | H | 3267, 1770, 1612 [Nujol]. | 2.8∼3.4(m, 2H), 3.42, 3.72(ABq, J=14.5Hz, 2H), 5.10 5.15(2×d, J=4.5Hz, 1H), 5.63, 5.69(2×d, J=4.5Hz, 1H), 5.90(d, J=16Hz, 1H), 6.36, 6.76(2×m, 1H), 6.45, 6.53(2×s, 1H), 7.23(d, J=16Hz, 1H)[NaHCO₃—D₂O] | 1-(4), 3-(2). |
| 8 | 1:1 | H | CH=CHCF₃(1Z.2E) | H | 3340, 1770, 1640, 1530 [KBr]. | 3.67(d, J=7.8Hz, 2H), 3.75∼4.30(m, 2H), 5.67, 5.73(2×d, J=4.5Hz, 1H), 6.15∼6.70(m, 2H), 6.96, 7.24(2×t, 7.8Hz, 1H), 7.05, 7.13(2×s, 1H), 7.20, 7.68(2×d, J=10Hz, J=16.5Hz, 1H)[NaHCO₃—D₂O] | 1-(4), 4-(2). |
| 9 | 1:1 | H | CH=CHCF₃ (Z) | H | 3360, 1772, 1708, 1655, 1628, 1532 [KBr]. | 3.68(d, J=7.8Hz, 2H), 3.99, 4.19(ABq, J=18Hz, 2H), 5.18 5.73(2×d, J=4.5Hz, 1H), 6.17, 6.27(2×d, J=4.5Hz, 1H), 6.1∼6.7(m, 1H), 7.05, 7.34(2×t, 7.8Hz, 1H), 7.07, 7.15 (2×s, 1H), 7.23(d, J=12.8Hz, 1H) [NaHCO₃—D₂O]. | 4-(2). |
| 10 | 1:2 | H | CH₂N ⊕ C₅H₅ | H | 3380, 1770, 1620, 1525 [KBr]. | 3.66, 4.08(ABq, J=18Hz, 2H), 3.78(d, J=8Hz, 2H), 5.66, 5.71(2×d, J=5Hz, 1H), 5.80 6.00(ABq, J=15Hz, 2H), 6.20, 6.26(2×d, J=5Hz, 1H), 7.11, 7.24(2×s, 1H), 6.8∼7.5(m, 1H), 8.4∼9.5(m, 5H) [D₂O] | 3-(7), 4-(2) |
| 11 | 2:3 | H | CH₂OMe | H | 3170br, 1760, 1622 [Nujol] | nd | |
| 12 | 3:5 | H | CH₂OCOMe | H | 3275, 1770, 1630 [Nujol]. | 2.75(s, 3H), 3.70(d, J=8Hz, 2H), 3.86, 4.13(ABq, J=18Hz, 2H), 5.60, 5.70(2×d, J=6Hz, 1H), 6.22, 6.28(2×d, J=6Hz, 1H), 6.98, 7.38(2×t, J=8Hz, 1H), 7.07, 7.16(2×s, 1H) [NaHCO₃—D₂O]. | 1-(4), 3-(2). |
| 13 | 2:3 | H | CH₂OCONH₂ | H | 3250, 1760, 1700 [Nujol]. | 3.66(d, J=8Hz, 2H), 3.83, 4.08(ABq, J=18Hz, 2H), 5.12, 5.31(ABq, J=12Hz, 2H), 5.61, 5.67(2×d, J=4Hz, 1H), 6.19, 6.24(2×d, J=4Hz, 1H), 7.00, 7.14(2×s, 1H), 6.95, 7.36 (2×t, J=8Hz, 1H), [NaHCO₃—D₂O]. | 1-(4), 4-(2) |
| 14 | 1:1 | Na | CH₂SMe | Na | 3370, 1755, 1590, 1525 [KBr]. | 2.46(s, 3H), 3.67(d, J=8Hz, 2H), 3.7∼4.3(m, 4H), 5.62(d, J=5Hz, ½H), 5.66(d, J=4Hz, ½H), 6.12(d, J=5Hz, ½H), 6.17(d, J=4Hz, ½H), 6.94, 7.35(2×t, J=8Hz, 1H), 7.05, 7.14(2×s, 1H)[D₂O]. | 1-(4), 3-(2). |
| 15 | 1:1 | H | CH₂SCH₂CN | H | 3300, 2240, 1765, 1625. 1530 [Nujol]. | 3.68(d, J=8Hz, 2H), 3.91, 4.20(ABq, J=13Hz, 2H), 4.01(s, 2H), 5.65, 5.71(2×d, J=5Hz, 1H), 6.19, 6.23(2×d, J=5Hz, 1H), 6.97, 7.38(2×t, J=8Hz, 1H), 7.07, | 4-(2), 1-(4), 3-(2), |

TABLE 2(1)-continued

Carboxylic acids

| No. | cis:trans | R³ | R⁵ | R⁸ | IR ν: cm⁻¹ | NMR δ: ppm | Example No. |
|---|---|---|---|---|---|---|---|
| 16 | | H | CH₂SCHF₂ | H | 3275br, 1765, 1660 sh, 1625 [Nujol]. | 7.15(2×s, 1H) [NaHCO₃—D₂O]. nd | 4-(2), 1-(4), 3-(2), 4-(2). |
| 17 | 2:3 | Na | 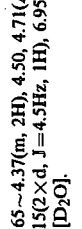 | Na | 1748 [Nujol]. | 3.67(d, J=8Hz, 2H), 3.65~4.37(m, 2H), 4.50, 4.71(ABq, J=21Hz, 1H), 5.54, 5.59(2×d J=4.5Hz, 1H), 6.09, 6.15(2×d, J=4.5Hz, 1H), 6.95, 7.35(2×t, J=8Hz, 1H), 7.04, 7.14 (2×s, 1H), 8.41(s, 1H) [D₂O]. | 1-(1), 3-(2), 4-(2). |
| 18 | 3:5 | Na |  | Na | 1770, 1662, 1630 [KBr]. | 3.60, 3.69(2×d, J=7Hz, 2H), 3.91~4.10(m, 2H), 4.17~4.41(m, 2H), 5.04, 5.61(2×d, J=5 Hz, 1H), 6.10, 6.17(2×d, J=5Hz, 1H), 6.93, 7.33(2×t, J=7Hz, 1H), 7.03, 7.12(2×s, 1H), 9.15(s, 1H) [Na-salt-D₂O]. | 1-(1), 3-(2), 4-(2). |
| 19 | 1:1 | H |  | H | 3300, 1764, 1627, 1529, 1367 [KBr]. | 3.69(d, J=8Hz, 2H), 4.07(ABq, J=17Hz, 2H), 4.75(ABq, J=12Hz, 2H), 5.58, 5.62(2×d, J= 4Hz, 1H), 6.18, 6.20(d, J=4Hz, 1H), 6.98, 7.40(2×t, J=8Hz, 1H), 7.03, 7.13(2×s, 1H), 9.88(s, 1H) [NaHCO₃—D₂O]. | 1-(4), 3-(2), 4-(2). |
| 20 | 1:1 | H |  | H | 3390, 1763, 1622, 1523, 1376 [KBr]. | 3.18(s, 3H), 3.68(d, J=8Hz, 2H), 4.03(ABq, J=17Hz, 2H), 4.67(ABq, J=14Hz, 2H), 5.57, 5.61(2×d, J=4Hz, 1H), 6.14, 6.17(2×d, J=4Hz, 1H), 6.94, 7.37(2×t, J=8Hz, 1H), 7.01, 7.11(2×s, 1H) [NaHCO₃—D₂O]. | 1-(4), 3-(2), 4-(2). |
| 21 | 1:1 | H |  | H | 3300, 1763, 1621, 1511, 1382, 1355 [KBr]. | 3.69(d, J=8Hz, 2H), 4.16(ABq, J=ABq, J=18Hz, 2H), 4.53(ABq, J=13.5Hz, 2H), 5.58, 5.62(2×d J=4Hz, 1H), 6.14, 6.19(2×d, J=4Hz, 1H), 6.97, 7.38(2×t, J=8Hz, 1H), 7.04, 7.13(2×s, 1H) [NaHCO₃—D₂O]. | 1-(4), 3-(2), 4-(2). |
| 22 | 1:1 | H |  | H | 3410, 1762, 1615, 1528, 1361 [KBr]. | 3.68(d, J=9Hz, 2H), 4.06(ABq, J=18Hz, 2H), 4.65(ABq, J=14Hz, 2H), 4.87, 5.01(2×s, 2H), 5.58, 5.62(2×d, J=4Hz, 1H), 6.14, 6.19(2×d, J=4Hz, 1H), 6.70~7.50(m, 1H), 7.04, 7.13(2×s, 1H) [NaHCO₃—D₂O]. | 1-(4), 3-(2), 4-(2). |
| 23 | 1:1 | H | MeN-N see R⁵ (CH₂S) | H | 1765, 1710, 1630, [KBr]. | 3.37(d, J=5Hz, 2H), 3.69(s, 2H), 3.95(s, 3H), 4.35(s, 3H), 5.03, 5.07(2×d, J=5Hz, 1H), 5.82(d, J=5Hz, 1H), 6.41, 6.53(2×s, 1H), 6.61, 6.93(2×t, J=8Hz, 1H)[CD₃SOCD₃—CD₃OD—CDCl₃]. | 1-(4) 3-(6). |
| 24 | 3:5 | H | OMe | H | 3275, 1760, 1620 | 3.68, 3.72(2×d, J=8Hz, 2H), 3.73~4.25(m, 2H), 4.21, 4.23(2×s, 3H), 5.64, 5.70(2×d, | 1-(4), |

TABLE 2(1)-continued

Carboxylic acids

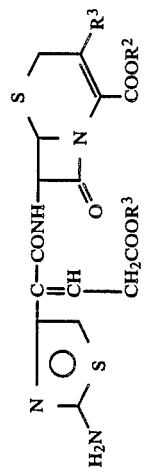

| No. | cis:trans | $R^3$ | $R^5$ | $R^8$ | IR $\nu$ : cm$^{-1}$ | NMR $\delta$: ppm | Example No. |
|---|---|---|---|---|---|---|---|
| 25 | 3:5 | H | Cl | H | [Nujol]. | $J=6Hz, 1H$), 6.00, 6.05(2×d, $J=6Hz$, 1H), 6.97, 7.37(2×t, $J=8Hz$, 1H), 7.10, 7.16(2×s, 1H)[NaHCO$_3$—D$_2$O]. | 3-(2), 4-(2). |
|  |  |  |  |  | 3275, 1760, 1625 [Nujol]. | 3.64, 3.65(2×d, $J=8Hz$, 1H), 3.97, 4.34:4.00, 4.37(2×ABq, $J=18Hz$, 2H), 5.68, 5.71(2× d, $J=6Hz$, 1H), 6.17, 6.22(2×d, $J=6Hz$, 1H), 6.94, 7.33(2×t, $J=8Hz$, 1H), 7.03, 7.13(2× s, 1H)[NaHCO$_3$—D$_2$O]. | 1-(4), 3-(2), 4-(2). |
| 26 | 1:2 | H | SCH$_2$CH$_2$F | H | 3300, 1763, 1660, 1629, 1531 [KBr]. | 3.52(dt, $J_1=22.5Hz$, $J_2=6Hz$, 2H), 3.67(d, $J=7.5Hz$, 2H), 3.83, 4.41(ABq, $J=17.1Hz$, 2H), 5.07(dt, $J_1=47.7Hz$, $J_2=6Hz$, 2H), 5.63, 5.69(2×d, $J=5Hz$, 1H), 6.15, 6.21(2×d, $J=$ 5Hz, 1H), 6.96, 7.36(2×t, $J=7.5Hz$, 1H), 7.06, 7.15(2×s, 1H) [NaHCO$_3$—D$_2$O]. | 1-(4), 3-(4), 3-(5). |
| 27 | 3:7 | Na | SCH$_2$CF$_3$ | Na | nd | 3.70(d, $J=7Hz$, 2H), 3.6~4.4(m, 2H), 4.30, 4.85(ABq, $J=15Hz$, 2H), 5.67, 5.74(2×d, $J=$ 4Hz, 1H), 6.20, 6.27(2×d, $J=4Hz$, 1H), 7.00, 7.38(2×t, $J=7Hz$, 1H), 7.07, 7.17(2×s, 1H) [D$_2$O]. | 3-(2),(4), 1-(2). |
| 28 | 4:5 | H | SCH=CH$_2$ | H | 3150, 1760, 1705 [Nujol]. | 3.68(d, $J=7Hz$, 2H), 4.15(brs, 2H), 5.6~6.2(m, 1H), 6.35(q, $J_1=16Hz$, $J_2=8Hz$, 1H), 6.8~7.6(m, 2H) [NaHCO$_3$—D$_2$O]. | 1-(4), 3-(4). |

TABLE 2(2)

Carboxylic acids $$\text{H}_2\text{N}-\underset{\text{S}}{\boxed{\phantom{X}}}-\text{C}-\text{CONH}-\underset{\text{CR}^1}{\boxed{\phantom{X}}}\underset{\text{R}^2\text{COOR}^3}{\underset{\text{O}}{\boxed{\phantom{X}}}}\underset{\text{COOR}^2}{\overset{\text{R}^3}{=}}$$

| No. | cis:trans | $R^1$ | $R^2$ | $R^3$ | $R^5$ | $R^6$ | IR (KBr)ν: cm$^{-1}$ | NMR δ: ppm | Example No. |
|---|---|---|---|---|---|---|---|---|---|
| 1 | cis | H | — | H | Me | H | nd | 2.17(s, 3H), 5.08(d, J=4.5Hz, 1H), 5.78(d, J=4.5Hz, 1H), 6.50(s, 1H), 6.86 (s, 1H) [CDCl$_3$—CD$_3$OD]. | 1-(4), 3-(2), 4-(2) |
| 2 | cis | H | — | h | CH=CH$_2$ | H | 1765, 1700sh, 1650 1615. | 3.60, 3.74(ABq, J=17Hz, 2H), 5.17(d, J=5Hz, 1H), 5.32(d, J=11Hz, 1H), 5.53 (d, J=17Hz, 1H), 5.83(d, 5Hz, 1H), 6.50(s, 1H), 6.81(s, 1H), 7.12(dd, J$_1$=11Hz, J$_2$=17Hz, 1H) [CDCl$_3$—CD$_3$SOCD$_3$—CD$_3$OD]. | 1-(4), 3-(2), 4-(2) |
| 3 | cis | H | — | H | CH$_2$OCOMe | H | 1779, 1717, 1615. | 2.10(s, 3H), 6.55(s, 1H), 6.87(s, 1H) [CDCl$_3$—CD$_3$OD]. | 1-(4), 3-(2), 4-(2) |
| 4 | trans | H | — | H | CH$_2$OCOMe | H | 1780, 1730, 1650. | 2.10(s, 3H), 5.73(d, J=5Hz, 1H), 6.17(s, 1H), 6.97(s, 1H) [CDCl$_3$—CD$_3$OD]. | 1-(4), 3-(2), 4-(2) |
| 5 | cis | H | CH$_2$CH$_2$ | Na | H | Na | 3300, 3200, 2900, 1755, 1650, 1600, 1550, 1410, 1360. | 2.88(m, 4H), 4.05(m, 2H), 5.65(d, J=6.0Hz, 1H), 6.28(d, J=6.0Hz, 1H), 6.75 (m, 1H), 7.00(m, 1H), 7.22(m, 1H) [D$_2$O]. | 1-(4), 3-(2), 4-(2) |
| 6 | trans | H | CH$_2$CH$_2$ | Na | H | Na | 3300, 3200, 2900, 1755, 1650, 1600, 1550, 1410, 1360. | 2.89(m, 4H), 4.00(m, 2H), 5.56(d, J=6.0Hz, 1H), 6.20(d, J=6.0Hz, 1H), 6.75 (m, 1H), 7.18(s, 1H), 7.25(m, 1H) [D$_2$O]. | 1-(1), 3-(2), 4-(2) |
| 7 | 1:1 | H | >CHMe | Na | H | Na | 3380, 1758, 1640, 1580. | 1.70, 173(2×d, J=7Hz, 3H), 3.5~4.5(m, 3H), 5.57, 5.63(2×d, J=5Hz, 1H), 6.16~6.32(m, 1H), 6.67~6.83(m, 1H), 6.83, 7.24(2×d, J=11Hz, 1H), 7.01, 7.11(2×s, 1H) [D$_2$O]. | 1-(2), 3-(2), 4-(2) |
| 8 | exo | H | >CHMe | Na | H | Na | 3380, 1758, 1645, 1595. | 2.31(brs, 3H), 3.7~4.3(m, 2H), 5.51(d, J=5Hz, 1H), 6.12(d, J=5Hz, 1H), 6.68~6.77(m, 1H), 6.89~7.05(m, 2H) [D$_2$O]. | 1-(2), 3-(2), 4-(2) |
| 9 | trans | H | (CH$_2$)$_3$ | Na | H | Na | 3300, 3200, 2900, 1760, 1655, 1600, 1550, 1410, 1360. | 2.15(m, 2H), 2.64(m, 4H), 4.00(m, 2H), 5.55(d, J=6.0Hz, 1H), 6.20(d, J=6.0 Hz, 1H), 6.75(m, 1H)7.10(s, 1H), 7.29(m, 1H) [D$_2$O]. | 1-(1), 3-(2), 4-(2) |
| 10 | cis | H | (CH$_2$)$_3$ | Na | H | Na | 3300, 3200, 2900, 1760, 1655, 1600, 1550, 1410, 1360. | 2.15(m, 2H), 2.70(m, 4H), 4.01(m, 2H), 5.63(d, J=5Hz, 1H), 6.26(d, J=6.0 Hz, 1H), 6.75(m, 1H), 6.97(s, 1H), 7.29(m, 1H) [D$_2$O]. | 1-(1), 3-(2), 4-(2) |
| 11 | cis | H | >CMe$_2$ | Na | H | Na | 3400, 1760, 1690, 1570. | 1.83(s, 6H), 3.7~4.3(m, 2H), 5.63(d, J=5Hz, 1H), 6.28(d, J=5Hz, 1H), 6.7~6.8 (m, 1H), 6.99(s, 2H) [D$_2$O]. | 1-(1), 3-(2), 4-(2) |
| 12 | trans | H | >CMe$_2$ | Na | H | Na | 3400, 1758, 1600sh 1600. | 1.63(s, 3H), 1.06(s, 3H), 3.74~4.30(m, 2H), 5.60(d, J=5Hz, 1H), 6.23(d, J=5 Hz, 1H), 6.73~6.83(m, 1H), 7.08(s, 1H), 7.47(s, 1H) [D$_2$O]. | 1-(2), 3-(2), 4-(2) |
| 13 | cis | H | CD$_2$ | Na | H | Na | 3580, 3260, 1770, 1700, 1650, 1620, 1570, 1545 [Nujol] | 3.70~4.35(m, 2H), 5.65(d, J=5Hz, 1H), 6.29(d, J=5Hz, 1H), 6.73~6.83(m, 1H), 6.95(s, 1H), 7.06(s, 1H) [D$_2$O]. | 1-(1), 3-(2), 4-(2) |
| 14 | 1:1 | Cl | — | H | H | H | nd | 3.40~3.70(m, 2H), 5.13(d, J=5Hz, 1H), 5.91(d, J=5Hz, 1H), 6.5~6.7(m, 1H), 6.50, 6.83(2×s, 1H) [CD$_3$OD]. | 1-(4), 3-(2), 4-(2) |
| 15 | 1:1 | Cl | (CH$_2$)$_2$ | H | H | H | 3300, 1765, 1720, 1627, 1530. | 2.8~3.15(m, 2H), 3.2~3.55(m, 2H), 3.75~4.3(m, 2H), 5.62(d, J=4.5Hz, 1H), 6.16, 6.23(2×d, J=4.5Hz, 1H), 7.65~7.9(m, 1H), 7.19, 7.49(2×s, 1H) [D$_2$O—NaHCO$_3$]. | 1-(4), 3-(2), 4-(2) |
| 16 | 10:1 | Cl | (CH$_2$)$_3$ | Na | H | Na | nd | 2.20~3.30(m, 6H), 3.85~4.15(m, 2H), 5.62(d, J=3Hz, 1H), 6.23(d, J=3Hz, 1H), 6.75(brs, 1H), 7.15, 7.55(2×s, 1H) [D$_2$O]. | 1-(2), 3-(2), 4-(2) |
| 17 | cis | Cl | SCH$_2$ | H | H | H | nd | 3.8~4.3(m, 2H), 4.14(s, 2H), 5.61(d, J=4.5Hz, 1H), 6.24(d, J=4.5Hz, 1H), 6.74(t, J=3Hz, 1H), 7.44(s, 1H) [D$_2$O—NaHCO$_3$]. | 1-(4), 3-(2), 4-(2) |

TABLE 2

Carboxylic acids $$\text{H}_2\text{N}-\underset{\text{W}}{\overset{}{\text{C}}}-\underset{\text{S}}{\overset{}{\text{O}}}-\underset{\text{CR}^1}{\overset{}{\text{C}=}}-\text{CONH}-\overset{\text{R}^4}{\underset{}{\text{C}}}-\underset{\text{N}}{\overset{\text{A}}{\text{C}}}\underset{\text{COOR}^6}{\overset{\text{R}^5}{=}}$$
$$\text{R}^2\text{COOR}^3$$

| No. | cis: trans | X | R¹ | R² | R³ | R⁴ | R⁵ | R⁸ | IR(KBr)ν: cm⁻¹ | NMR δ(D₂O): ppm | Example No. |
|---|---|---|---|---|---|---|---|---|---|---|---|
| 18 | 1:2 | SO α | H | CH₂ | Na | H | H | Na | 3400, 1775, 1600, 1525, 1410, 1360. | 3.65(brd, J=8Hz, 2H), 3.85~4.15(m, 1H), 4.65~5.0(m, 1H), 5.34, 5.43 (2×d, J=5Hz, 1H), 6.11, 6.23(2×d, J=5Hz, 1H), 6.49~6.62(m, 1H), 6.99, 7.37(2×t, J=8Hz, 1H), 7.03, 7.13(2×s, 1H). | 1-(1), 3-(2), 4-(2) |
| 19 | 1:1 | SO β | H | CH₂ | Na | H | H | Na | 3400, 1770, 1600, 1525, 1410, 1360. | 3.65, 3.67(2×d, J=8Hz, 2H), 5.42, 5.46(2×d, J=4Hz, 1H), 6.47, 6.53(2× d, J=4Hz 1H), 6.55~6.62(m, 1H), 6.97, 7.52(2×t, J=8Hz, 1H), 7.06, 7.14(2×s, 1H). | 1-(2), 3-(2), 4-(2) |
| 20 | 2:3 | O | H | CH₂ | Na | OMe | CH—CH₂ | Na | nd | 3.70(d, J=8Hz, 2H), 4.00, 4.08(2×s, 3H), 5.0~5.3(m, 2H), 5.55~5.90(m, 3H), 6.94, 7.40(2×t, J=8Hz, 1H), 7.07, 7.14(2×s, 1H), 7.0~7.50(m, 1H). | 1-(2), 3-(2), 4-(2) |
| 21 | 1:1 | O | H | CH₂ | H | OMe | MeN—N<br>‖<br>CH₂S—N | H | 1773, 1670, 1630. | nd | 1-(4), 3-(2), 4-(2) |
| 22 | 1:1 | O | H | CH₂ | Na | OMe | MeN—N<br>‖<br>CH₂S—N | Na | nd | 3.70(d, J=8Hz, 2H), 3.99, 4.07(2×s, 3H), 4.50(s, 3H), 5.63, 5.68(2×s, 1H), 6.95, 7.43(2×t, J=8Hz, 1H), 7.05, 7.13(2×s, 1H). | 1-(2), 3-(2), 4-(2) |

TABLE 2

Carboxylic acids $$R-\underset{\underset{R^2COOR^3}{|}}{\underset{CH}{C}}-CONH-\left[\begin{array}{c}S\\\hline\\O\end{array}\right]\underset{COOR^6}{\overset{R^5}{\diagup}}$$

| No. | cis: trans | R | R² | R³ | R⁵ | R⁸ | IR (KBr)ν: cm⁻¹ | NMR δ: ppm | Example No. |
|---|---|---|---|---|---|---|---|---|---|
| 1 | trans | Ph | CH₂ | Na | H | | Na | 3400, 1760, 1650, 1585, 1510, 1410, 1365. | 3.47(d, J=8Hz, 2H), 3.65~4.25(m, 2H), 5.55(d, J=5Hz, 1H), 6.15(d, J=5Hz, 1H), 6.66~6.76(m, 1H), 7.30(t, J=8Hz, 1H), 7.66~8.05(m, 5H) [D₂O]. | 1-(2), 3-(2). |
| 2 | trans | ⟨thiophene⟩ | CH₂ | Na | H | | Na | 3395, 1760, 1650, 1585, 1510, 1410, 1365. | 3.70(d, J=8Hz, 2H), 3.60~4.26(m, 2H), 5.56(d, J=5Hz, 1H), 6.16(d, J=5Hz, 1H), 6.70~6.80(m, 1H), 7.25(t, J=8Hz, 1H), 7.45~7.65(m, 2H), 7.96~8.05(m, 1H) [D₂O]. | 1-(2), 3-(2). |
| 3 | 2:8 | ⟨thiophene⟩ | CH₂ | Na | MeN—⟨N⟩—CH₂S | | Na | 3400, 1760, 1660, 1590, 1385. | 3.66, 3.72(2×d, J=8Hz, 2H), 3.90, 4.22(ABq, J=18Hz, 2H), 4.47(s, 3H) 4.43, 4.81(ABq, J=14Hz, 2H), 5.56, 5.62(2×d, J=5Hz, 1H), 6.08, 6.20, (2×d, J=5Hz, 1H), 6.80, 7.26(2×t, J=8Hz, 1H), 7.5~8.05(m, 3H). | 1-(2), 3-(2). |
| 4 | 2:1 | N⟨pyridine⟩ | CH₂ | Na | H | | Na | 3420, 1760, 1655, 1585, 1413, 1365. | 3.63, 3.76(2×d, J=8Hz, 2H), 3.73~4.33(m, 2H), 5.66(d, J=5Hz, 1H), 6.22, 6.32(2×dd, J₁=5Hz, J₂=9Hz, 1H), 6.7~6.83(m, 1H), 7.18, 7.43(2×t, J=8Hz, 1H), 8.02 8.11(2×d, J=2Hz, 1H), 9.43, 9.51(2×d, J=2Hz, 1H) [D₂O]. | 1-(2), 3-(2). |
| 5 | 5:4 | H₂N-⟨N-O⟩ | CH₂ | H | H | | H | 3450, 3360, 1772, 1717, 1670, 1630, 1520. | 3.45, 3.57(2×d, J=7.5Hz, 2H), 5.80, 5.86(2×d, J=4.5, 1H), 6.55~6.75(m, 1H), 6.65, J=4.5Hz, 1H), 3.3~3.8(m, 2H), 5.10, 5.13(2×d, 6.80(2×s, 1H), 6.67, 6.78(2×t, J=7.5Hz, 1H) [CD₃OD]. | 1-(4), 3-(2), 4-(2). |
| 6 | | H₂N-⟨N-S⟩ | CH₂ | Na | H | | Na | 3400, 1758, 1655, 1590, 1365. | 3.76, 3.81(2×d, J=7Hz, 2H), 4.02(m, 2H), 5.63, 5.58(2×d, J=5Hz, 1H), 6.23, 6.32(2×d, J=5Hz, 1H), 6.76(m, 1H), 7.50, 7.56(2×t, J=7Hz, 1H) [D₂O]. | 1-(2), 3-(2), 4-(2). |
| 7 | | H₂N-⟨N-S⟩ | — | H | H | | H | 3352, 1773, 1716. | nd | 1-(4), 3-(2), 4-(2). |

TABLE 3

Pharmaceutical esters

Structure: R⁰NH-[thiazole ring]-CONH-CH(CH₂COOR³)-C(=...)- with β-lactam fused to S-containing ring bearing COOR⁸

| No. | cis:trans | R⁰ | R³ | R⁸ | IR(CHCl₃) ν: cm⁻¹ | NMR(CDCl₃) δ: ppm | Example No. |
|---|---|---|---|---|---|---|---|
| 1 | cis | H | H | POM | 3420, 2980, 1780, 1750, 1660, 1630, 1530, 1480, 1390[KBr]. | 1.20(s, 9H), 3.15~3.75(m, 4H), 5.04(d, J=5Hz, 1H), 5.81, 5.92(ABq, J=6Hz, 2H), 5.90(d, J=5Hz, 1H), 6.40~6.70(m, 2H), 7.35(s, 1H). | 3-(2), 4-(2), 5-(2). |
| 2 | 1:1 | H | H | POM | 3420, 2980, 1780, 1750, 1660, 1630, 1530, 1480, 1390[KBr]. | 1.20(s, 9H), 3.15~3.75(m, 4H), 5.04, 5.06(2×d, J=5Hz, 1H), 5.81, 5.92(ABq, J=6Hz, 2H), 5.85~5.95(m, 1H), 6.40~6.70; 6.83~7.03(2×m, 2H), 7.37(s, 1H) [CDCl₃—CD₃OD]. | 3-(2), 4-(2), 5-(2). |
| 3 | 1:1 | H | POM | POM | 3395, 3320, 1790, 1753, 1685, 1110, 988. | nd | 4-(3), 5-(2). |
| 4 | 1:1 | H | AOM | AOM | 3380, 3310, 1790, 1741, 1687, 1150, 985. | nd | 4-(2), 5-(5). |
| 5 | 1:1 | Cbz | Bzl | POM | nd | 1.20(s, 9H), 3.00~3.90(m, 4H), 5.13(s, 2H), 5.10, 5.15, 5.33; 5.15, 5.37(2×ABq, J=12Hz, 2H), 5.55~6.00(m, 3H), 5.85, 5.92(2×d, J=5Hz, 1H), 6.36~6.53(m, 1H), 6.65, 7.07(2×t, J=8Hz, 1H), 6.94, 6.96(2×s, 1H), 7.20~7.50(m, 10H), 7.66, 8.05(2×d, J=8Hz, 1H). | 4-(2). |

TABLE 4

Side chain fragment acids and derivatives $$\text{RNH-C(=N)-S-CH=C(COOR}^1\text{)-CH}_2\text{-CH}_2\text{COOR}^2$$

| | R | R¹ | R² | IR(Nujol)ν:cm⁻¹ | NMR δ: ppm |
|---|---|---|---|---|---|
| 1 | BOC (cis) | H | H | 3120, 1700, 1675. dp 153~154° C. | 1.50(s, 9H), 3.45(d, J=7.5Hz, 2H), 7.00(t, J=7.5 Hz, 1H), 7.13(s, 1H) [CD₃SOCD₃]. |
| 2 | BOC (trans) | H | H | 3150, 1700, 1630, 1600. dp 165~167° C. | 1.49(s, 9H), 3.41(d, J=7.5Hz, 2H), 6.89(t, J=7.5 Hz, 1H), 7.08(s, 1H) [CD₃SOCD₃] |
| 3 | Cbz | H | H | 3200, 1738, 1715, 1690. dp 169~172° C. | 3.44, 3.50, (2×d, J=8Hz, 2H), 5.25(s, 2H), 7.07, 7.35(2×t, J=8Hz, 1H), 7.12(s, 1H), 7.38(brs, 5H) [CDCl₃—CD₃OD] |
| 4 | HCO | H | H | 3400, 1718, 1690, 1630, 1550. dp 168° C. | 3.45, 3.63(2×d, J=7.5Hz, 2H), 7.14, 7.32(2×t, J=7.5Hz, 1H), 7.23, 7.25(2×s, 1H), 8.51(s, 1H) [CDCl₃—CD₃OD]. |
| 5 | ClCH₂CO | H | H | 3100, 1720, 1685, 1620. dp 153–155° C. | 3.45(d, J=8Hz, 2H), 4.37(s, 2H), 6.97, 7.05(2×t, J=8Hz, 1H), 7.23, 7.27(2×s, 1H) [CD₃SOCD₃]. |
| 6 | BOC | H | Bzl | 3160, 1740, 1724, 1700, 1678, 1255, 1168. | 3.95(d, J=7.5Hz, 2H), 5.50(s, 2H), 7.26(t, J=7.5 Hz, 1H), 7.30(brs, 1H), 7.49(s, 1H), 7.75(s, 5H), 11.86(brs, 1H) [CD₃SOCD₃]. |
| 7 | HCO (1 cis: 2 trans) | H | t-Bu | 3150, 3100, 1720, 1690, 1635. mp. 185~188° C. | 1.40(s, 9H), 3.43(d, J=7Hz, 2H), 6.89, 7.00(2×t, J=7Hz, 1H), 7.20, 7.26(2×s, 1H), 8.48(s, 1H) [CD₃SOCD₃]. |
| 8 | HCO | H | Bzl | 1735, 1680, 1620. dp 153~155° C. | 3.69(d, J=7Hz, 2H), 5.12(s, 2H), 7.17(t, J=7Hz, 1H), 7.21(s, 1H), 7.32(s, 5H), 8.46(s, 1H) [CD₃SOCD₃]. |
| 9 | ClCH₂CO | H | Me | nd | 3.39(d, J=7.5Hz, 2H), 3.70(s, 3H), 4.24(s, 2H), 7.11(s, 1H), 7.23(t, J=7.5Hz, 1H), 9.37(brs, 2H) [CDCl₃]. |
| 10 | ClCH₂CO | H | Bzl | 1726, 1685, 1160. dp 155° C. | 3.95, 4.01(2×d, J=7.5Hz, 2H), 4.71(s, 2H), 5.45, 5.47(2×s, 2H), 7.28, 7.40(2×t, J=7.5Hz, 1H), 7.58, 7.65(2×s, 1H), 7.70(s, 5H), 12.9(brs, 1H) [CD₃SOCD₃]. |
| 11 | Cbz | H | Me | 3400~2300, 1740, 1550. | 3.58~3.73(m, 2H), 3.63(s, 3H), 5.27(s, 2H), 7.03 ~7.46(m, 7H) [CD₃SOCD₃]. |
| 12 | Cbz (trans) | H | t-Bu | 3160~2200, 1720, 1680, 1635. mp. 169~171° C. | 1.42(s, 9H), 3.53(d, J=7Hz, 2H), 5.29(s, 1H), 7.27(t, J=7Hz, 1H), 7.35(s, 1H), 7.30~7.50(m, 5H) [CD₃COCD₃]. |
| 13 | Cbz (cis) | H | t-Bu | nd | 1.44(s, 9H), 3.53(d, J=7Hz, 2H), 5.27(s, 2Hz, 7.13(t, J=7Hz, 1H), 7.24(s, 1H), 7.30~7.47(m, 5H) [CDCl₃]. |
| 14 | Cbz (2 cis: 1 trans) | H | Me— Bzl | 3150~2050, 1720, 1670, 1620, 1570. mp. 160~163° C. | 2.33(s, 3H), 2.53, 2.70(2×d, J=8Hz, 2H), 5.11(s, 2H), 5.26(s, 2H), 6.99~7.40(m, 10H) [CDCl₃—CD₃OD]. |
| 15 | Cbz (2 cis: 3 trans) | H | Bzl | 1725, 1675, 1620, 1575. mp. 164~166° C. | 3.51, 3.73(2×d, J=7Hz, 2H), 5.13(s, 2H), 5.26 (s, 2H), 7.06, 7.10(2×s, 1H), 7.0~7.5(m, 11H) [CDCl₃—CD₃OD]. |
| 16 | Cbz | H | PMB | 1720, 1575, 1515. mp. 145~148° C. | 3.80(d, J=8Hz, 2H), 3.90(s, 3H), 5.20(s, 2H), 5.33(s, 2H), 7.00(s, 1H), 6.85~7.60(m, 10H) [CDCl₃—CD₃OD]. |
| 17 | H (HCl salt) | Me | H | 3330~2450, 1720, 1680, 1630. | 3.39(d, J=7Hz, 2H), 3.73(s, 3H), 6.88(s, 1H), 7.25(t, J=7Hz, 1H) [CD₃SOCD₃]. |
| 18 | Cbz (1 cis: 2 trans) | H | CH₂ CH CH₂ | 3515, 2480(br), 1736, 1549, 1305, 1086 (CHCl₃). mp. 122~130° C. | 3.35(d, J=8Hz, 4/3H), 3.68(d, J=8Hz, 2/3H), 4.56 (d, J=6Hz, 2H), 5.11~5.37(m, 4H), 5.65~6.15(m, 1H), 6.90~7.41(m, 7H), 9.82(bs, 2H), [CDCl₃]. |
| 19 | Cbz (1 cis: 5 trans) | H | CHMe CH ‖ CH₂ | 3420, 2500(br), 1732, 1549, 1302, 1087 (CHCl₃). mp. 127~131° C. | 1.16(d, J=7Hz, 1/2H), 1.29(d, J=7Hz, 5/2H), 3.46 (d, J=8Hz, 5/3H), 3.68(d, J=8Hz, 1/3H), 5.05~ 5.49(m, 3H), 5.16(s, 2H), 5.66~6.02(m, 1H), 7.08 ~7.57(m, 7H) [CDCl₃—CD₃OD]. |
| 20 | Cbz (9 cis: 11 trans) | H | CH₂ CMe ‖ CH₂ | 3420, 1736, 1548, 1307, 1085 (CHCl₃). mp. 120~123° C. | 1.73(s, 3H), 3.52(d, J=8.5Hz, 11/10H), 3.73 (d, J=8.5Hz, 9/10H), 4.54(s, 2H), 4.95(brs, 2H), 5.26(s, 2H), 6.99~7.46(m, 7H) [CDCl₃—CD₃OD]. |
| 21 | Cbz (1 cis: 4 trans) | H | CH₂ CH ‖ CHMe | 3415, 1732, 1548, 1304, 1076 (CHCl₃). mp. 139~142° C. (decomp.). | 1.67(d, J=6Hz, 3H), 3.44(d, J=8Hz, 8/5H), 3.64 (d, J=8Hz, 2/5H), 4.49(d, J=6Hz, 2H), 5.23(s, 2H), 5.35~6.05(m, 2H), 7.05~7.41(m, 7H) [CDCl₃—CDCl₃]. |

TABLE 4-continued

Side chain fragment acids and derivatives

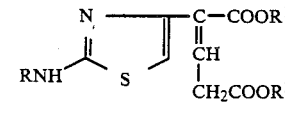

| | R | R¹ | R² | IR(Nujol)ν:cm⁻¹ | NMR δ: ppm |
|---|---|---|---|---|---|
| 22 | Cbz (1 cis: 2 trans) | H | CMe₂—CH=CH₂ | 3175, 2520(br), 1732, 1659, 1071. mp. 167~168° C. (decomp.). | 1.98(s, 3H), 2.03(s, 3H), 3.82(d, J=8Hz, 4/3H), 3.86(d, J=8Hz, 2/3H), 4.87(d, J=7Hz, 2H), 5.64 (s, 2H), 5.52~5.71(m, 1H), 7.21(t, J=8Hz, 1/3H), 7.65~7.69(m, 5-2/3H) [CD₃SOCD₃—CD₃OD]. |
| 23 | Cbz (1 cis: 2 trans) | H | CH₂—CH=CMe₂ | 3150~2200, 1725, 1675, 1620, 1585. mp. 170~171° C. | 1.67(s, 3H), 1.72(s, 3H), 3.22(d, J=7Hz, 2H), 4.54(brd, J=8Hz, 2H), 5.23(s, 2H), 5.30(brt, J= 8Hz, 1H), 6.38(s, 1H), 6.99(s, 1H), 7.40(m, J= 7Hz, 6H) [CD₃SOCD₃]. |
| 24 | Cbz | H | CH₂—CH—CHPh | nd | TLC[EtOAc/CHCl₃(1:1)]: Rf=0.2 |
| 25 | H (HCl salt) | Me | Me | 3200, 1720, 1625, 1605. [CHCl₃]. | 3.44(d, J=7Hz, 2H), 3.75(s, 3H), 3.85, 3.88(2×s, 3H), 6.70, 6.75(2×s, 1H), 6.97, 7.43(2×t, J=7 Hz, 1H) [CDCl₃—CD₃OD]. |
| 26 | BOC (trans) | Me | Me | 3415, 1720, 1541, 1155 [CHCl₃]. | 1.52(s, 9H), 3.54(d, J=6.5Hz, 2H), 3.64(s, 3H), 3.76(s, 3H), 7.11(s, 1H), 7.18(t, J=6.5Hz, 1H), 9.12(brs, 1H) [CDCl₃]. |
| 27 | BOC (cis) | Me | Me | 3410, 1720, 1541, 1150 [CHCl₃]. | 1.51(s, 9H), 3.54(d, J=6.5Hz, 2H), 3.69(s, 3H), 3.83(s, 3H), 7.03(s, 1H), 7.08(t, J=6.5Hz, 1H), 9.12(brs, 1H) [CDCl₃]. |
| 28 | Cbz | Me | Me | 3390, 1720, 1540 [CHCl₃]. | 3.41, 3.48(2×d, J=8Hz, 2H), 3.65, 3.73, 3.69, 3.83(4×s, 6H), 5.24(s, 2H), 7.00~7.37(m, 7H) [CDCl₃]. |
| 29 | Cbz | Et | Et | 3395, 1720 [CHCl₃]. | 1.19, 1.20, 1.22, 1.30(4×t, J=8Hz, 6H), 3.34, 3.42(2×d, J=8Hz, 2H), 4.08, 4.12, 4.15, 4.24 (4×q, J=8Hz, 4H), 5.21, 5.22, 5.24(3×s, 2H), 7.03, 7.13(2×t, J=8Hz, 1H), 7.03(s, 1H), 7.31(s, 5H), 10.15(brs, 1H)[CDCl₃]. |
| 30 | Cbz | Bzl | Bzl | 3400, 1725 [CHCl₃]. | 3.31, 3.42(2×d, J=7Hz, 2H), 5.01, 5.03, 5.11, 5.17(4×s, 6H), 6.96~7.30(m, 17H), 10.19(brs, 1H) [CDCl₃]. |
| 31 | Cbz | PMB | Bzl | nd | 3.40(d, J=7Hz, 2H), 3.75(s, 3H), 5.10(s, 2H), 5.15(s, 2H), 5.20(s, 2H), 6.8~7.4(m, 16H) [CDCl₃]. |
| 32 | Cbz | BH | Bzl | 3490, 1725 [CDCl₃]. | 3.34, 3.40(2×d, J=7Hz, 2H), 5.02, 5.05, 5.09, 5.17(4×s, 4H), 6.8~7.4(m, 23H), 9.90(brs, 1H) [CDCl₃]. |
| 33 | HCO (trans) | Me | Me | 3380, 3140, 1722, 1705, 1695 [CHCl₃] mp. 100° C. | 3.46(d, J=7.5Hz, 2H), 3.66(s, 3H), 3.78(s, 3H), 7.05(s, 1H), 7.24(t, J=7.5Hz, 1H), 8.49(s, 1H) [CDCl₃]. |
| 34 | HCO (cis) | Me | Me | 3390, 3150, 1715, 1700, 1535 [CHCl₃]. | 3.56(d, J=7.0Hz, 2H), 3.73(s, 3H), 3.84(s, 3H), 7.02(t, J=7Hz, 1H), 7.12(s, 1H), 8.55(s, 1H) [CDCl₃]. |
| 35 | HCO (cis) | Me | t-Bu | 3380, 1710, 1540 [CHCl₃]. mp. 101~104° C. | 1.47(s, 9H), 3.50(d, J=7Hz, 2H), 3.86(s, 3H), 7.07(t, J=7Hz, 1H), 7.13(s, 1H), 8.60(s, 1H) [CDCl₃]. |
| 36 | HCO (trans) | Me | t-Bu | nd | 1.44(s, 9H), 3.27(d, J=7Hz, 2H), 3.80(s, 3H), 7.05(s, 1H), 7.31(t, J=7Hz, 1H), 8.52(s, 1H) [CDCl₃]. |
| 37 | ClCH₂CO (trans) | Me | Me | nd | 3.50(d, J=6.5Hz, 2H), 3.68(s, 3H), 3.79(s, 3H), 4.25(s, 2H), 7.24(s, 1H), 7.24(t, J=6.5Hz, 1H) [CDCl₃]. |
| 38 | ClCH₂CO (cis) | Me | Me | 3470, 1725, 1715, 1680, 1585 [CHCl₃]. | 3.60(d, J=7Hz, 2H), 3.75(s, 3H), 3.87(s, 3H), 4.27(s, 2H), 7.18(s, 1H), 7.18(t, J=7Hz, 1H) [CDCl₃]. |
| 39 | Ph₃C (3 cis: 2 trans) | Me | Me | 3380, 1720, 1703, 1500, 1480, 1425 [CHCl₃]. | 3.43(d, J=6.5Hz, 2H), 3.26, 3.64(2×s, 3H), 3.70, 3.75(2×s, 3H), 6.44, 6.63(2×s, 1H), 6.54, 6.70 (2×s, 1H), 7.01(t, J=6.5Hz, 1H), 7.25(s, 15H) [CDCl₃]. |

What we claim is:

1. A compound of the formula wherein

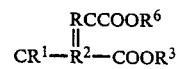

R is aminothiazolyl or aminothiadiazolyl where the amino group of each is protected or unprotected, $R^1$ is hydrogen or halogen, $R^2$ is lower alkylene, $R^3$ is (a) hydrogen, (b) a member selected from the group consisting of lithium, sodium, potassium, magnesium, calcium and magnesium, (c) alkenyl having 2–7 carbon atoms or (d) aralkyl having 7 to 15 carbon atoms, and $R^6$ is (a) hydrogen, (b) a member selected from the group consisting of lithium, sodium, potassium, magnesium, calcium and magnesium, (c) alkyl of 1 to 8 carbon atoms, (d) aralkyl of 7 to 15 carbon atoms, (e) aryl of 6 to 12 carbon atoms, (f) silyl of 3 to 12 carbon atoms or (g) alkenyl of 2 to 7 carbon atoms.

2. A compound claimed in claim 1 wherein R is aminothiazolyl, optionally protected by benzyloxycarbonyl, t-butoxycarbonyl, methylbenzyloxycarbonyl formyl, chloroacetyl, or benzal.

3. A compound as claimed in claim 1 wherein $R^1$ is hydrogen.

4. A compound as claimed in claim 1 wherein $R^2$ is straight or blanched chain alkylene of 1 to 3 carbon atoms.

5. A compound as claimed in claim 4 wherein $R^2$ is methylene.

6. A compound as claimed in claim 1 wherein $R^3$ is hydrogen, benzyl, methylbenzyl, p-methoxybenzyl or p-nitrobenzyl.

7. a compound as claimed in claim 1 wherein $R^6$ is hydrogen, diphenylmethyl or p-methoxybenzyl.

8. A compound according to claim 1, said compound being 2-(2-benzyloxycarbonylamino-thiazol-4-yl)-4-benzyloxycarbonyl-2-butenoic acid.

* * * * *

UNITED STATES PATENT AND TRADEMARK OFFICE
CERTIFICATE OF CORRECTION

PATENT NO. : 4,912,224

DATED : March 27, 1990

INVENTOR(S) : YOSHIO HAMASHIMA

It is certified that error appears in the above-identified patent and that said Letters Patent is hereby corrected as shown below:

Column 80, line 65 (claim 1), change the formula to read:

$$-- \quad \begin{array}{c} RCCOOR^6 \\ \| \\ CR^1-R^2-COOR^3 \end{array} \quad --$$

Signed and Sealed this

Twenty-fifth Day of June, 1991

Attest:

HARRY F. MANBECK, JR.

Attesting Officer

Commissioner of Patents and Trademarks